US005831008A

United States Patent [19]
Huang

[11] Patent Number: 5,831,008
[45] Date of Patent: Nov. 3, 1998

[54] RETINOBLASTOMA PROTEIN-INTERACTING ZINC FINGER PROTEINS

[75] Inventor: Shi Huang, San Diego, Calif.

[73] Assignee: La Jolla Cancer Research Foundation, La Jolla, Calif.

[21] Appl. No.: 399,411

[22] Filed: Mar. 6, 1995

Related U.S. Application Data

[63] Continuation-in-part of Ser. No. 292,683, Aug. 18, 1994, abandoned.

[51] Int. Cl.$^6$ .............................. C07K 14/47; C07K 7/06
[52] U.S. Cl. ......................... 530/350; 530/324; 530/327; 930/10
[58] Field of Search ..................................... 530/324, 327, 530/350, 399; 930/10; 514/2, 12

[56] References Cited

FOREIGN PATENT DOCUMENTS

WO 94/12521  6/1994  WIPO .

OTHER PUBLICATIONS

Huang, Shi "Blimp–1 is the Murine Homolog of the Human Transcriptional Repressor PRDI–BF1." *Cell* 78:9 (1994).
Ogata, Ronald T. and Zepf, Nancy E. "The Murine Slp Gene." *J. Immuno.* 147:2756–2763 (1991).
Steele–Perkins, George et al., "Functional Interaction of RB with a Novel Multidomain Zinc–Finger Protein." *J. Cell. Biochem.* Suppl. 178(N216) (1994).
Buyse, Inge M. et al., "The Retinoblastoma Protein Binds to RIZ, a Zinc–Finger Protein that Shares an Epitope with the Adenovirus E1A Protein." *Proc. Natl. Acad. Sci. USA* 92:4467–4471 (1995).
Kaelin, William G. et al., "Expression Cloning of a cDNA Encoding a Retinoblastoma–Binding Protein with E2F–like Properties." *Cell* 70:351–364 (1992).
Carriga, Gian et al., "Migrations of the *Caenorhabditis elegans* HSNs are Regulated by egl–43, a Gene Encoding Two Zinc Finger Proteins." *Genes & Develop* 7:2097–2109 (1993).
Morishita, Kazuhiro et al., "Retroviral Activation of a Novel Gene Encoding a Zinc Finger Protein in IL–3–Dependent Myeloid Leukemia Cell Lines." *Cell* 54:831–840 (1988).
Bourne et al., "The GTPase superfamily: conserved structure and molecular mechanism." *Nature*, 349:117–127 (1991).
Boyd et al., "A region in the c–terminus of adenovirus 2/5 E1a protein is required for association with a cellular phosphoprotein and important for the negative modulation of T24–ras mediated transformation, tumorigenesis and etastasis." *EMBO. J.* 12:469–478 (1993).
Cherington et al., "Separation of simian virus 40 large T antigen transforming and origin–binding functions from the ability to block differentiation." *Mol. Cell. Biol.*, 8:1380–1384 (1988).
DeCaprio et al., "SV40 large tumor antigen forms a specific complex with the product of the retinoblastoma susceptibility gene." *Cell*, 54:275–283 (1988).

DeFeo–Jones et al., "Cloning of cDNAs for cellular proteins that bind to the retinoblastoma gene product." *Nature*, 352:251–254 (1991).
Dowdy et al., "Physical interaction of the retinoblastoma protein with human D cyclins." *Cell* 73:499–511 (1993).
Durfee et al., "The retinoblastoma protein associates with the protein phosphatase type 1 catalytic subunit." *Genes Dev.*, 7:555–569 (1993).
Dyson et al., "Adenovirus E1A makes two distict contacts with the retinoblastoma protein." *J. Virol.*, 66:4606–4611 (1992).
Ewen et al., "Functional interactions of the retinoblastoma protein with mammalian D–type cyclins." *Cell*, 73:487–497 (1993).
Ford et al., "Nuclear protein with sequence homology to translation initiation factor eIF–4A." *Nature*, 332:736–738 (1988).
Harlow et al., "Association of adenovirus early region 1A proteins with cellular polypeptides." *Mol. Cell. Biol.*, 6:1579–1589 (1986).
Hirling et al., "RNA helicase activity associated with the human p68 protein." *Nature*, 339:562–564 (1989).
Hu et al., "The regions of the retinoblastoma protein needed for binding to adenovirus E1A or SV40 large T antigen are common sites for mutations." *EMBO J.*, 9:1147–1155 (1990).
Huang et al., "Two distinct and frequently mutated regions of retinoblastoma protein are required for binding to SV40 T antigen." *EMBO J.*, 9:1815–1822 (1990).
Huang et al., "A cellular protein that competes with SV40 T antigen for binding to the retinoblastoma gene product." *Nature*, 350:160–162 (1991).
Huang et al., "The retinoblastoma protein region required for interaction with the E2F transcription factor includes the T/E1A binding and carboxy–terminal sequences." *DNA Cell Biol.*, 11:539–548 (1992).
Kaelin, Jr. et al., "Definition of the minimal simian virus 40 large T Antigen and adenovirus E1A–binding domain in the retinoblastoma gene product." *Mol. Cell. Biol.*, 10:3761–3769 (1990).
Keller and Maniatis, "Identification and characterization of a novel repressor of β–interferon gene expression." *Genes Dev.*, 5:868–879 (1991).
Kimelman et al., "E1a regions of the human adenovirus and of the highly oncogenic simian adenovirus 7 are closely related." *J. Virol.*, 53:399–409 (1985).
M. Kozak, "An analysis of 5' noncoding sequences from 699 vertebrate messenger RNAs." *Nucl. Acids Res.* 15:8125–8148 (1987).

(List continued on next page.)

*Primary Examiner*—Stephen Walsh
*Assistant Examiner*—Christine Saoud
*Attorney, Agent, or Firm*—Campbell & Flores LLP

[57] ABSTRACT

The present invention provides a mammalian retinoblastoma protein-interacting zinc finger protein and active fragments thereof, which bind retinoblastoma protein.

6 Claims, 21 Drawing Sheets

OTHER PUBLICATIONS

Krieg and Melton, "Functional messenger RNAs are produced by SP6 in vitro transcription of cloned cDNAs." *Nucl. Acids Res.*, 12:7057–7070 (1984).

Lane and Hoeffler, "SV40 large T shares an antigenic determinant with a cellular protein of molecular weight 68,000." *Nature*, 288:167–170 (1980).

Lillie et al., "Functional domains of adenovirus type 5 Ela proteins." *Cell*, 50:1091–1100 (1987).

Ludlow et al., "SV40 large T antigen binds preferntially to an under phosphorylated member of the retinoblastoma susceptibility gene product family." *Cell*, 56:57–65 (1989).

Mihara et al., "Cell cycle–dependent regulation of phosphorylation of the human retinoblastoma gene product." *Science*, 246:1300–1303 (1989).

E. Moran, "A region of SV40 large T antigen can substitute for a transforming domain of the adenovirus E1A products." *Nature*, 334:168–170 (1988).

Moran and Matthews, "Multiple functional domains in the adenovirus E1A gene." *Cell*, 48:177–178 (1987).

J.R. Nevins, "E2F: a link between the Rb tumor suppressor protein and viral oncoproteins." *Science*, 258:424–429 (1992).

Pawson and Gish, "SH2 and SH3 domains: from structure to function." *Cell* 71:359–362 (1992).

Qin et al., "Identification of a growth suppression domain within the retinoblastoma gene product." *Genes Dev.*, 6:953–964 (1992).

Quinlan et al., "Growth factor induction by the adenovirus type 5 E1A 12S protein is required for immortilization of primary epithelial cells." *Mol. Cell. Biol.*, 8:3191–3203 (1988).

Quinlan and Douglas, "Immortization of primary epithelial cells requires first– and second– exon functions of adenovirus type 5 12S." *J. Virol.*, 66:2020–2030 (1992).

Ren et al., "Identificaiton of a ten–amino acid proline–rich SH3 binding site." *Science*, 259:1157–1161 (1993).

Saraste et al., "The P–loop—a common motif in ATP– and GTP– binding proteins." *Trends. Biochem. Sci.*, 15:430–434 (1990).

Scheffner et al., "RNA unwinding activity of SV40 large T antigen." *Cell* 57:955–963 (1989).

Smith and Ziff, "The amino–terminal region of the adenovirus serotype 5 Ela protein performs two separate functions when expressed in primary baby rat kidney cells." *Mol. Cell. Biol.*, 8:3882–3890 (1988).

Subramanian et al., "Enhanced ras oncogene mediated cell transformation and tumorigenesis by adenovirus 2 mutants lacking the C–terminal region of Ela protein." *Oncogene*, 4:415–420 (1989).

Templeton et al., "Nonfunctional mutants of the retinoblastoma protein are characterized by defects in phosphorylation, viral oncoprotein association, and nuclear tethering." *Proc. Natl. Acad. Sci. USA*, 88:3033–3037 (1991).

Wang et al., "Identification of specific adenovirus E1A N–terminal residues critical to the bindings of cellular proteins and the control of cell growth." *J. Virol.*, 67:476–488 (1993).

R.A. Weinberg, "Tumor suppressor genes." *Science*, 254:1138–1146 (1991).

Welch and Wang, "A C–terminal protein–binding domain in the retinoblastoma protein regulates nuclear c–Abl tyrosine kinase in the cell cycle." *Cell*, 75:779–790 (1993).

Whyte et al., "Association between an oncogene and an anti–oncogene: the adenovirus E1A proteins bind to the retinoblastoma gene product." *Nature* 334:124–129 (1988).

Whyte et al., "Cellular targets for transformation by te adenovirus E1A proteins." *Cell*, 56:67–75 (1989).

Walker et al., "Distantly related sequences in the $\alpha$– and $\beta$– subunits of ATP synthase, myosin, Kinases and other ATP–requiring enzymes and a common nucleotide binding fold." *Embo J.*, 1(8):945–951 (1982).

Chen et al., "Phosphorylation of the retinoblastoma gene product is modulated during the cell cycle and cellular differentiation." *Cell*, 58:1193–1198 (1989).

DeCaprio et al., "The product of the retinoblastoma susceptibility gene has properties of a cell cycle regulatory element." *Cell*, 58:1085–1095 (1989).

S. Huang, "Blimp–1 is the murine homolog of the human transcriptional repressor PRDI–BF1." *Cell*, 78:1 (1994).

Iggo and Lane, "Nuclear protein p68 is an RNA–dependent ATPase." *EMBO J.*, 8(6):1827–1831 (1989).

Moran et al., "Identification of separate domains in the adenovirus E1A gene for immortilization activity and the activation of virus early genes." *Mol. and Cell. Biol.*, 6(10):3470–3480 (1986).

Buchkovich et al., "The retinoblastoma protein is phosphorylated during specific phases of the cell cycle." *Cell*, 58:1097–1105 (1989).

Chen, Phang–Lang et al., "Identification of a Human Homologue of Yeast Nuc2 Which Interacts with the Retinoblastoma Protein in a Specific Manner." *Cell Growth & Differ.* 6:199–210 (1995).

Lewin, R. Science 237: 1570, 1987.

Reeck et al. Cell. vol. 50: 667, 1987.

|  |  |  |  |  |  |  |  |  |  |  |  |  |  |  |
|---|---|---|---|---|---|---|---|---|---|---|---|---|---|---|
| | | | | cr1 | | | | | | cr2 | | | | cel |
| RIZ | 215 | SAPEQP | APLPEVG | NQDAV | P | QV | A | IP | LPACEPQPEVDGKQ | EVT | DCE | VND | - VE 267 | EDLLEE PQS 320 |
| Ad2E1A | 49 | TAPEDP | - - - - - - - | NEEAV | S | QI | - | FP | - - - - - - - - - - - - - - | - - - | - - - | - - - | - - 80 | EDLLNE SGQP 233 |
| Ad5 | | TAPEDP | - - - - - - - | NEEAV | S | QI | - | FP | - - - - - - - - - - - - - - | DSV | MLA | VQE | G ID L | EDLLNE PGQ |
| Ad7 | | DGPEDP | - - - - - - - | NEGAV | N | GF | - | FT | - - - - - - - - - - - - - - | DSV | MLA | VQE | G ID L | EDLLE- GGD |
| Ad12 | | SAGEDN | - - - - - - - | NEQAV | N | EF | - | FP | - - - - - - - - - - - - - - | DSM | LLA | ADE | G LD I | LDLIQE EER |
| SA7 | | TCQEDE | - - - - - - - | NEEAV | D | GV | - | FS | - - - - - - - - - - - - - - | ESL | ILA | ASE | G LF L | HDLIEE VEQ |
| Ad40 | | DGFEED | A - - - - - - | NQEAV | D | GM | - | FP | - - - - - - - - - - - - - - | DAM | LLA | AEE | G IE M | EDLLEE DPT |
| | | | | | | | | | | ERL | LSE | AES | A AE S | |
| | | | | | | | | | 289 | | | | 107 | 312 |

FIG. 2B-1

|  |  |  |  |  |  |  |  |  |  |  |  |  |  |  |  |  |  |  |  |  |
|---|---|---|---|---|---|---|---|---|---|---|---|---|---|---|---|---|---|---|---|---|
| RIZ | 744 | A | L | R | D | F | G | K | P | N | D | G | K | A | A | W | T | - | D | T V L T S K K P - K L E S R - - - - - - - S D S P A W S L S G R D E - R E T G S P P C F D E Y |
| GRB2 N | 5 | | | | | | | | | | | | | | | | | | | | |
| GRB2 C | 163 | A | L | F | D | F | D | P | Q | E | D | G | E | - | - | - | - | - | - | - - - - - - - - - - - - - - - - - - D N S D P N W K G A C H - - G Q T G M F P R N Y V T |
| P85 | 10 | A | L | Y | D | Y | K | K | E | R | E | E | D | I | D | L | H | L | G | D I L T V N K G S L V A L G F S D G Q E A R P E E I G W L N G Y N E T T G E R G D F P G T Y V E |
| v-abl | 68 | A | L | Y | D | F | V | A | S | G | D | N | T | - | - | - | - | - | - | - - - - - - - - - - - - - - - - - - Y N H N G E W C E A Q T K - N G Q - G W V P S N Y I T |
| c-src | 88 | A | L | Y | D | Y | E | S | R | T | E | T | D | - | - | - | - | - | - | - - - - - - - - - - - - - - - - - - M N T E G D W W L A H S L T T G Q T G Y I P S N Y V A |
| GAP | 286 | A | I | L | P | Y | T | K | V | P | D | T | D | E | - | - | - | - | - | - - - - - - - - - - - - - - - - - - N E L E D G W M W V T N L R T D E Q G L I V E D L V E |
| PLC | 798 | A | L | F | D | Y | K | A | Q | R | E | D | E | - | - | - | - | - | - | - - - - - - - - - - - - - - - - - - E K Q E G G W W R G D Y G G K K K Q - L W F P S N Y V E |
| v-crk | 375 | A | L | F | D | F | K | G | N | D | D | E | D | - | - | - | - | - | - | - - - - - - - - - - - - - - - - - - D K P E E Q W W N A E D M D G K R - G M I P V P Y V E |

FIG. 2B-2

| RIZ | 961 | LPPLLTPTE | P | S | S | P | P | P | C | P | P | V | LTVATPPPLLPLSHPSSDASPQQCPSPFSNTTAQSPLPIILSPTVSPSPSPIPPVEPLMSAASEGPPTLS |
|---|---|---|---|---|---|---|---|---|---|---|---|---|---|
| Formin | | | A | P | P | T | P | P | P | L | P | P | LJPPPPLPPGLGPLPP |
| 3BP1 | | | A | P | T | M | P | P | L | P | P | V | PPQPARRQSR |
| 3BP2 | | | P | P | A | Y | P | P | V | P | P | V | PRKPAFSDLPRAHSFTSKSPSPLLPPPP |
| m4 mAChR | | | P | P | A | L | P | P | P | P | R | P | VP |

```
RIZ         1125  CNVCESPFLSIKDLTKHLSVHAEEWPFKCEFCVQLFKVKTDLSEHRFLLHGVGNIFVCSVCKKEFAFLCNLQQHQRDLHPDEVCTH  1210
PRDI-BF1     543  CNVCAKTFGQLSNLKVHLRVHSGERPFKCQTCNKGFTQLAHLQKH-YLVHTGEKPHECQVCHKRFSSTSNLKTHLR-LHSGEKPYQ   626
CONSENSUS         CNVC....F.....L..HL.VH..E.PFKC..C..F....L..H..L.H.......C.VC.K.F....NL..H.R.LH..E....
DNA-CONTACTS                  *          *   *  *                           *  *  *    *  *    *
```

FIG. 2C-1

```
RIZ          39  TRIGVWATKPILKGKKFGPFVGDKKKRSQVRNNV---YMWEVYYPNLGWMCIDATDPEKGNWLRYVNWACSGEEQNLFPL  115
PRDI-BF1     60  EVIGVMSKEYIPKGTRFGPLIGEIYTNDTVPKNANRKYFWRIYSRGELHHFIDGFNEEKSNMMRYVNPAHSPREQNLAAC  139
CONSENSUS        ..IGV......I.KG..FGP..G......V..N.....Y.W..Y.........ID....EK.NW.RYVN.A.S..EQNL...

RIZ         116  EINRAIYYKTLKPIAPGEELLVWYNGEDNP  145
PRDI-BF1    140  QNGMNIYFYTIKPIPANQELLVWYCRDFAE  169
CONSENSUS        .....IY..T.KPI....ELLVWY......
```

FIG. 2C-2

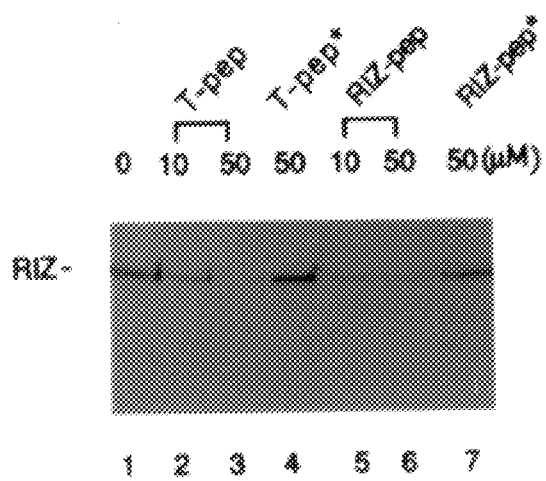
FIG. 4
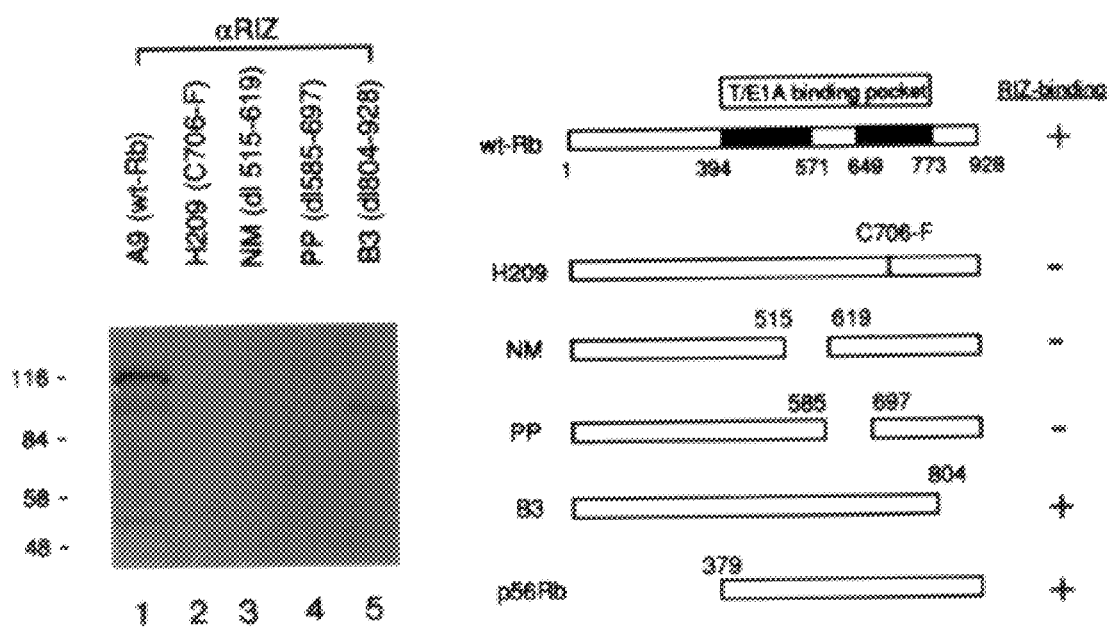
FIG. 5A
FIG. 5B

```
          10        20        30        40        50        60        70        80        90       100       110       120
1234567890123456789012345678901234567890123456789012345678901234567890123456789012345678901234567890123456789012345678901234567890
ACTCCAGTCCAGTGGAATCTGTCTTAGATCTGCAGTGTGCATAAAAAGCATTGTAGTGACTCTGAAGGCAGGAATTCAAAGAAAGTCATTCAGTGCAGCTAGTGCAGCTAGTGCTGTAAAG         2640
 T  P  V  Q  W -E  S  V  L  D  L  S  V  H  K  K  H  C  S  D  S  E  G  K  E  F  K  E  S  H  S  V  Q  P  T  C  S  A  V  K
AAAGGAAACCAACCACCTGCAGAAGGTTCTTCTCAATGAATATAATGGCATCGATTACCTGCCAGTCGAGAAACCCTGCTAGAAAACCCTGCAGATGGACCAGGAGACCAGGAGCCCAAGTCCTTGTAAATCCTA        2760
 K  R  K  P  T  T  C  M  L  Q  K  V  L  L  N  E  Y  N  G  I  D  L  P  V  E  N  P  A  D  G  T  R  S  P  S  P  C  K  S  L
GAAGCTCAGCCAGATCCTGACCTCGGTCCGGGTCCGGACAGATCCTCTTGTTTGCCCTGCCTGATGTTTGTCCTTCATCACCTGACGACACCCTCCCTTTCATCCGGT                      2880
 E  A  Q  P  D  P  D  L  G  G  P  P  S  G  F  F  P  A  P  T  V  E  S  T  P  D  V  C  P  S  S  P  A  L  Q  T  P  S  L  S  S  G
CAGCTGCCTCCTCTGATCCCACCACCATGCCCCTCTCAAATGCCACCGCACAGTCCCCACTTCTGTCCCCAACAGTGTCCCCCATTCTCCCCGTGGAGCCC                               3000
 Q  L  P  P  L  L  I  P  T  T  P  P  C  P  S  P  L  S  N  A  T  A  Q  S  P  L  P  T  V  P  P  L  L  P  T  V  P  L  P  A  P  S
TCCAGTGCATCTCACCACCTGCGCCCTCTCACCCGGGCCTCACCCGGGCCTCTGGTGTTTCCTCTGGTGATAATCTGGAGGCTTCTCTCCCTATCTCTTCCTCTTCGTTTTCTCCCCATCTCCTCTCT   3120
 S  S  A  S  P  H  P  C  P  S  P  L  S  S  S  P  G  P  P  T  L  S  S  S  P  S  P  I  P  P  P  V  E  P
CTGATGTCTGCGCCTCACCCGGGCCTCACCCCGGGCCTCTGGTGTTTCCTCTGGTGATAATCTGGAGGCTTCTCTCCCTATGATATCTTTCAAACAGGAGGAATTAGAGAATGAAGGTCTGAAGAAGCCCAGTCTGCT     3240
 L  M  S  A  A  S  P  G  P  P  T  L  V  F  P  L  V  I  I  W  R  L  L  S  L  M  I  S  F  K  Q  E  E  L  E  N  E  G  L  K  P  R  E  E  P  Q  S  A
GCAATATCATCTGTGTTGTTCAGGAAACATTCAACAAAAACTTTGTTGCAACGTCTGTGAATCACCTTTCTCTTCCATTAAAGATCTAACAAACATTTATCTATTCATGCTGAAGAA               3360
 A  I  S  S  V  V  S  G  D  D  N  L  E  A  S  L  P  M  I  S  F  K  Q  E  E  L  E  N  E  G  L  K  P  R  E  E  P  Q  S  A
GCTGAACAGGATGTTGTTGTTCAGGAAACATTCAACAAAAACTTTGTTGCAACGTCTGTGAATCACCTTTCTCTTCCATTAAAGATCTAACAAACATTTATCTATTCATGCTGAAGAA             3480
 A  E  Q  D  V  V  V  Q  E  T  F  N  K  N  F  V  C  N  V  C  E  S  P  F  L  S  I  K  D  L  T  K  H  L  S  I  H  A  E  E
TGGCCCTTCAAATGTGAATTTTGTGTGCAGCTTTTAAGGATAAACGGACTTGTCAGAAATATCTTGTGTGTTCTGTTTGTAAAAAAGAA                                       3600
 W  P  F  K  C  E  F  C  V  Q  L  F  K  D  K  T  D  L  S  E  H  R  F  L  L  H  G  G  V  G  N  I  F  V  C  S  V  C  K  K  E
TTTGCTTTTGTGCAATTTGCAGAGGCTTGCCAGAGCTTTAGAAACTTCTAAAGAAGAAGAGAAGATCCTTTAGAAACTTCTGAAGACTTTACAGATCCCAGCAAG                         3720
 F  A  F  L  C  N  L  Q  Q  H  Q  R  D  L  H  P  P  D  K  V  C  T  H  H  E  F  E  S  G  T  L  R  R  P  Q  N  F  T  D  D  P  S  K
GCCCATGTAGAGGCATGAGCAGAGCTTGCCAGAAGATCCTTTAGAAACTTCTAAAGAAGAAGAGAAGAGTAAATGATTCCTCTGAAGAGCTTTACACGACTATAAAAATAATGGCTTCTGGA         3840
 A  H  V  E  H  M  Q  S  L  P  E  D  P  L  E  T  S  K  E  E  E  L  N  D  S  S  E  E  L  Y  T  T  T  I  K  I  M  A  S  G
```

```
hRIZ    MAQNITEVA ATETLAEVPE HVLRGLPEEV RLFPSAVDKT RIGVWATKPI LKGKKFGPFV    60
rRIZ    M-QNITESVA ATETLAEVPE HVLRGLPEEV RLFPSAVDKT RIGVWATKPI LKGKKFGPFV    59
Consensus M QN TE VA ATETLAEVPE HVLRGLPEEV RLFPSAVDKT RIGVWATKPI LKGKKFGPFV   60 hRIZ    GDKKKRSQVK NNVYMWEVYY PNLGWMCIDA TDPEKGNWLR YVNWACSGEE QNLFPLEINR   120
rRIZ    GDKKKRSQVR NNVYMWEVYY PNLGWMCIDA TDPEKGNWLR YVNWACSGEE QNLFPLEINR   119
Consensus GDKKKRSQV  NNVYMWEVYY PNLGWMCIDA TDPEKGNWLR YVNWACSGEE QNLFPLEINR   120 hRIZ    AIYYKTLKPI APGEELLVWY NGEDNPEIAA AIEEERASAR SKRSSPKSRK GKKKSENKN    180
rRIZ    AIYYKTLKPI APGEELLVWY NGEDNPEIAA AIEEERASAR SKRSSPKSRR GKKKSENKN    179
Consensus AIYYKTLKPI APGEELLVWY NGEDNPEIAA AIEEERASAR SKRSSPKSR  GKKKS ENKN    180 hRIZ    KGNKIQDIQL KISEHDITSA NMRQSAEGPK EDEENPSASA EQPAILQEV ASQEVIPELA    240
rRIZ    KGIRTHPTQL KRSEIDITFA NMRQSAEGPK EEDIPIASA  FEQPAFLEEV GNQDAVPQVA    239
Consensus KG    QL  K SE D T A NMR SAEGPK E    ASA  EQPA LEV      .          240 hRIZ    TPAPAEPQP EFDERIEBAA CEVNDLQEEE EEEEEEEE EDDDDDELE DEGIEEAMF         300
rRIZ    IPLPAEPQP EVDGKQEVTD CEVNDVEEEE EEEEEE   EEEE----LG EDGVEEADMP        295
Consensus P PAEPQP E D  E D   CEVND EEE  EEEE   EE   E        G EEA MF        300 hRIZ    NESSKEPEI RCDEKPEDLL EEPKTISHET LEDCSEVTPA MQIPRIKEEA NGDVETFMF      360
rRIZ    NESSPKEPEI RCEEKPEDLL EEPDSMSNEA FEDSPLVTPP PHTPRAEEA NGDVETFMF      355
Consensus NE S KEPEI RC EKPEDLL EEP      E    VTP       EEA NGDV ETFMF        360
```

FIG. 10A

```
hRIZ       PCQHCERKF TKQGLERHMH IHIST NHAF KCKYCGK FG TQINRRRHER RHE GLKR P   420
rRIZ       PCQHCERKF TKQGLERHMH IHIST NHAF KCKYCCK FG TQINRRRHER RHE GLKR P   415
Consensus  PCQHCERKF TKQGLERHMH IHIST NHAF KCKYCGK FG TQINRRRHER RHE GLKR P   420 hRIZ       S TLQ SED  ADGKA GENV  SKD SSPP  LG DCLI NS EK SQTINS  S VEENGEVK  480
rRIZ       SVTLQ SEDP DDGK- GENV  SKD SSPPQ LG DCLI NS EK SQEVLNS SF VEENGEVK 473
Consensus  S TLQ SED    DGK  GENV  SKD SSPP  LG DCLI NS EK SQ    NS S VEENGEVK 480 hRIZ       ELHPCKYCKK VFGTHTNMRR HQRRVHERHL IPKGVRRKGG L E PQPPAE QADA QNVYV  539
rRIZ       ELHPCKYCKK VFGTHTNMRR HQRRVHERHL IPKGVRRKGG L E PQPPAE QAPPS QNVYV  533
Consensus  ELHPCKYCKK VFGTHTNMRR HQRRVHERHL IPKGVRRKGG L E PQPPAE QA    QNVYV  540 hRIZ       PSTEPEEEGE DDVYIMDIS SNISENLNYY IDGKIQTN N TSNCDVIEME S SA LYGI N  599
rRIZ       PSTEPEEEGE DDVYIMDIS SNISENLNYY IDGKIQTNSS TSNCDVIEME S SA LYGI D  593
Consensus  PSTEPEEEGE DDVYIMDIS SNISENLNYY IDGKIQTN    TSNCDVIEME S SA LYGI    600 hRIZ       CLLTPVTVEI TQNIK TQVP VTED F KEPL QSTN E KKR RTASPP LPK IK ET SD PM  659
rRIZ       CLLTPVTVEI TQNIK TQVS VTDDL KDSP SSTN D KKR RTASPP LPK IKDET SSDST   653
Consensus  CLLTPVTVEI TQNIK      VT  DL K    STN E KKR RTASPP LPK IK ET SD      660 hRIZ       VPSCSLSLPL SIST E VSF HKEK VYLSS KLKQLLQTQD KLT PAG SA EI PKLGPVC   719
rRIZ       APSCSLSLPL SIST E VSF HKEK VYLSS KLKQLLQTQD KLT PAG SA EI PKLGPVC   713
Consensus   PSCSLSLPL SIST E VSF HKEK VYLSS KLKQLLQTQD KLT PAG SA EI PKLGPVC   720
```

FIG. 10B

```
hRIZ      VSAPASMLPV TSSRFKRRTS SPPSSPQHSP ALRDFGKPLD GKAAWTDAQL TSKKGKLESH   779
rRIZ      ASAPASMLPV TSSRFKRRTS SPPSSPQHSP ALRDFGKPND GKAAWTDTVL TSKKQKLESR   773
Consensus .SAPASMLPV TSSRFKRRTS SPPSSPQHSP ALRDFGKP.D GKAAWTD..L TSKK.KLES.   780 hRIZ      SDSPAWSLSG RDERETMSPP CFDEYKMSKE WIASSIFSSV CNQQPLDLSS GVKQKEEGTG   839
rRIZ      SDSPAWSLSG RDERETLSPP CFDEYKHSKE WNASSIFSSV CNQQPLDLSS GVKQKEEGTG   833
Consensus SDSPAWSLSG RDERET.SPP CFDEYK.SKE W.ASS.FSSV CNQQPLDLSS GVKQK.EGTG   840 hRIZ      KTPVQWESVL DLSVHKKLCS HSVQPTCSAV KKLKPTTCML QKVLLNEYNG               899
rRIZ      KTPVRWESVL DLSVHKKPC. HLAQP---AA KKKKPTTCML QKVLLNEYNG               889
Consensus KTPV.WESVL DLSVHKK.C. H..QP....A KK.KPTTCML QKVLLNEYNG               900 hRIZ      IDLPMENPAD QTRSPSPCKS LEAQPDPHLG PISGFPAPTV ESIRPMCLPS SPPLQTFSLS   958
rRIZ      VSLPHETPEV TRSPSPCKS  PDTQPDPHLG PISSCSVPTA ESIPFWCPS SPPLQTVSLS    949
Consensus ..LP.E.... TRSPSPCKS. .....QPDP.LG P.S....PT. ES..P...PS SP.LQT.SLS   960 hRIZ      SGQLPPLLIP TIPSSPPPPCP PVLTVATPPP PLLPTVPLPA PSSGASPHIC PSPLSNITAQ   1018
rRIZ      SGQLPPLLIP TEPSSPPPPCP PVLTVATPPP PLLPTVPLSH PSSCASPQQC PSPLSNITAQ   1009
Consensus SGQLPPLL.P T.PSSPPPPCP PVLTVATPPP PLLPTVPL.. PSS.ASP..C PSP.SN.TAQ   1020 hRIZ      SPLPILSPTV SPSPSPIPPV EPLMSAASPG PPTLSSSSSS SSSSSSSSES SSSSFSPPPP   1078
rRIZ      SPLPILSPTV SPSPSPIPPV EPLMSAASPG PPTLSSSSSS SSSFSSSSS  SUSFSPP--   1067
Consensus SPLPILSPTV SPSPSPIPPV EPLMSAASPG PPTLSSSSSS SSS.S.S.S. S.S.SP.P..   1080
```

FIG. 10C

```
hRIZ        LSAISSVVSS GDNLEASLPM ISFKQEE EN EGLKP EEPQ SAAEQDVVQ ETFKKNFLCN   1138
rRIZ        LSALSSVVSS GDNLEASLPA VTFKQEE ES EGLKP VEEAP PAGQQS-VVQ ETFEKNFDCN  1126
Consensus   LSA .SSVVSS GDNLEASLP. .FKQEE E. EGLKP E... .A.Q. .VVQ ETF.KNF. CN  1140 hRIZ        VCESPFLSIK DLTKHLS HA EEWPFKCEFC VQLFK KTDL SEHRFLLHGV GNIFVCSVCK   1198
rRIZ        VCESPFLSIK DLTKHLS HA EEWPFKCEFC VQLFK KTDL SEHRFLLHGV GNIFVCSVCK   1186
Consensus   VCESPFLSIK DLTKHLS HA EEWPFKCEFC VQLFK KTDL SEHRFLLHGV GNIFVCSVCK   1200 hRIZ        KEFAFLCNLQ QHQRDLHPDK VCTHHEFESG TLRPQNFTDP SKA VEHM S LPE PLETSK    1258
rRIZ        KEFAFLCNLQ QHQRDLHPDE VCTHHEFESG TLRPQNFTDP SKA VEHM S LPE PLETSR    1246
Consensus   KEFAFLCNLQ QHQRDLHPD. VCTHHEFESG TLRPQNFTDP SKA VEHM S LPE PLETS.    1260 hRIZ        EEE LNDSSE ELYTTIKIMA SGIKTKDPDV RLGLNQHYPS FKPPPFQYHH RNPMGIGVTA   1318
rRIZ        EEE LNDSSE ELYTTIKIMA SGIKTKDPDV RLGLNQHYPS FKPPPFQYHH RNPMGIGVTA   1305
Consensus   EEE LNDSSE ELYTTIKIMA SGIKTKDPDV RLGLNQHYPS FKPPPFQYHH RNPMGIGVTA   1320 hRIZ        TNFTTHNIPQ TFTTAIRCTK CGKGVDNMPE LHKHILACAS ASDKKRYTPK KNPVPLKQTV   1378
rRIZ        TNFTTHNIPQ TFTTAIRCTK CGKGVDNMPE LHKHILACAS ASDKKRYTPK KNPVPLKQTV   1365
Consensus   TNFTTHNIPQ TFTTAIRCTK CGKGVDNMPE LHKHILACAS ASDKKRYTPK KNPVPLKQTV   1380 hRIZ        QPKNGVVVLD NSGKNAFRRM GQPKRU FEV EL KMS NKL KL ALKKKNQ LVQKAILQKN   1438
rRIZ        QPKNGVVVLD NSGKNAFRRM GQPKRU FV EL KMS NKL KL ALKKKNQ LVQKAILQKN    1425
Consensus   QPKNGVVVLD NSGKNAFRRM GQPKRU F.V EL KMS NKL KL ALKKKNQ LVQKAILQKN   1440
```

FIG. 10D

```
hRIZ        KSAKQKADLK  NAQESSHIC PYC REFTYI GSLNKHAAFS CPKKPLSPK  KVSHSSKKG    1498
rRIZ        RAAKQKADLR  DTSEASSHIC PYC REFTYI GSLNKHAAFS CPKKPLSPK  KVSHSSSKG    1485
Consensus              . .AKQKADL. . .E .SSHIC PYC .REFTYI GSLNKHAAFS CPKKPLSP.K . KVSHSSKKG   1500 hRIZ        GHSSPASSDK  NSNSNHRRRT ADMEIKMQSM QTPLGKTRAR SEGPIQV LP SSSFRSQNV    1558
rRIZ        GHASSESSDR  NSSCHRRRT ADTEIKMQST QNPLGKTRAR SIGPQASLP SSSFRSQNV      1545
Consensus   GH . S. .SSD . NS . . . RRRT AD .EIKMQS . Q . PLGKTRAR S . GP .Q . LP SSSFRS . QNV   1560 hRIZ        KFAASVKSKK  PSSSSLRNSS PIRMAKITHV EGKKPKAVAK NHSAQLSSKT  SRELHVRVQK   1618
rRIZ        KFAASVKSKK  PSSSSLRNSS PIRMAKITHV EGKKPKAVAK GHSAQLSSKG  SRELHVRVQK   1605
Consensus   KFAASVKSKK  . SSSSLRNSS PIRMAKITHV EGKKPKAVAK . HSAQLSSK. SR . LHVRVQK    1620 hRIZ        SKAVIQSKGT  LASKKRTDRF NIKSRERSGG PNTRSLQLAA AADLSENRE  DGSAKQELKD   1678
rRIZ        SKAVDQSKTA  LASKFRTDRF IVKSRERSGG PTTRSLQLAA AADLSESFRE DESARHELKD   1665
Consensus   SKAV . QSK . . LASK . RTDRF . . KSRERSGG P . TRSLQLAA AADLSE . . RE  D . SA . . ELKD    1680 hRIZ        FSYSLRLASR  CSPPAAYIT RQ RKVKAHA  ADFQGPFHK E             1719
rRIZ        FSYSLRLASR  CSSTAYIT RQ RKVKANA  ATHFQGPFHK EX            1707
Consensus   FSYSLRLASR  C. . . . . A . YIT RQ .RKVKA . A A . . FQGPF . K . E      1722
```

FIG. 10E

RETINOBLASTOMA PROTEIN-INTERACTING ZINC FINGER PROTEINS

This application is a continuation-in-part of U.S. Ser. No. 08/292,683, filed Aug. 18, 1994, now abandoned, the entire contents of which are incorporated herein by reference.

This invention was made in part with government support, under CA57496, awarded by the National Institutes of Health, and 5T30 CA30199, awarded by the Cancer Center Core. The United States government has certain rights in this invention.

BACKGROUND OF THE INVENTION

1. Field of the Invention

This invention relates to the field of molecular biology and, in particular, to nucleic acid molecules encoding an Rb-interacting zinc finger protein.

2. Background Information

The retinoblastoma Rb protein is known to play a key role in controlling normal cell proliferation and differentiation. The ability of a cell to divide requires the cell to pass through the various phases of the cell cycle. Although Rb is believed to keep normal cells from dividing by maintaining them in a phase of the cell cycle known as $G_1$ or $G_0$, the precise mechanism underlying Rb function is unknown.

The role that Rb plays in controlling cell growth makes it an attractive target for promoting the growth of tissues that normally do not grow because of the action of Rb. For example, cardiac muscle tissue or nerves that have lost function due to cell death are not usually repaired by subsequent proliferation of the remaining live cells. Thus, a method to block the growth controlling function of Rb can be useful for inducing tissue repair in situations of cardiac or neural cell death.

Rb also is known as a tumor suppressor since the abnormal growth of a cancer cell can result from inactivation of Rb protein. Such inactivation can occur either due to a mutation or to inactivation of Rb protein subsequent to binding a viral oncoprotein, a product of an oncogenic tumor virus. A particular region in Rb called the Rb pocket appears to be critical for its growth controlling function since Rb inactivation by mutation or by oncoprotein binding impacts this region.

The importance of the Rb pocket in the functioning of Rb and the understanding that viral oncoproteins can regulate Rb by binding the pocket suggest that there may be normal cellular proteins that can regulate the function of Rb by binding the pocket. The identification of such proteins will provide new approaches to regulate the control of cell proliferation mediated by Rb in diseases such as those that involve loss of cardiac or neural function or in the control of cancer. Thus, a need exists to identify proteins that can bind to and regulate Rb. The present invention satisfies this need and provides related advantages as well.

SUMMARY OF THE INVENTION

The present invention provides substantially purified mammalian Rb-interacting zinc finger proteins (RIZ), including for example, human RIZ and rat RIZ. In addition, the invention provides active fragments of a RIZ such as the sequences EIRCEEKPEDL (SEQ ID NO: 6) and EIRCDEKPEDL (SEQ ID NO: 91), which bind Rb. The invention also provides antibodies that can specifically bind to a RIZ or a mutant RIZ.

The invention further provides nucleic acid molecules encoding mammalian RIZ and active fragments thereof, vectors containing the nucleic acid molecules and host cells containing the vectors. In addition, the invention provides nucleotide sequences that can specifically hybridize to a nucleic acid molecule encoding a RIZ or a mutant nucleic acid molecule encoding a RIZ.

The invention also provides a screening assay useful for identifying agents that can effectively alter the association of a RIZ with a second molecule such as Rb or can effectively alter the activity of a RIZ. By altering the association of a RIZ with a second molecule or altering the activity of a RIZ, an effective agent can modulate a function of a cell such as cell proliferation.

The invention further provides methods for promoting the growth of a cell such as a neural cell or cardiac muscle cell by contacting the cell with an effective agent. For example, cell growth can be promoted by introducing into a cell an effective agent such as an expression vector having an expression control sequence operably linked to a nucleotide sequence encoding an active fragment of a RIZ.

The invention also provides methods of detecting a RIZ in a sample by detecting the presence of the RIZ protein or of a nucleic acid molecule encoding the RIZ. Such methods can be used to diagnose a pathology characterized by an increased or decreased level of expression of a RIZ in a cell or by expression of a mutant RIZ. Such a method also can be used to diagnose a pathology characterized by a mutant nucleic acid molecule encoding a RIZ.

The invention further provides methods useful for isolating Rb tumor suppressor protein or a mutant Rb from a sample. For example, Rb can be isolated from a sample by affinity chromatography using a RIZ or a RIZ active fragment such as the sequences EIRCEEKPEDL (SEQ ID NO: 6) or EIRCDEKPEDL (SEQ ID NO: 79).

BRIEF DESCRIPTION OF THE FIGURES

FIG. 1 shows the cDNA sequence (SEQ ID NO: 1) and the deduced amino acid (a.a.) sequence of full-sized rat RIZ protein (SEQ ID NO: 2). Numbers at right indicate nucleotide position; numbers at left indicate amino acid position. The following features are underlined: an upstream in-frame stop codon (nucleotide position 110-112), a cr2 core motif (304-309), 8 zinc fingers (a.a. positions 357-377, 478-499, 387-407, 1125-1303 (finger 4-6), 1323-1343 and 1445-1466), putative leucine zipper (a.a. position 667-695)) and a putative nuclear localization signal (a.a. positions 867-874). Single letter amino acid symbols are used.

FIGS. 2A to 2C show homologies between rat RIZ and various other proteins. Single letter amino acid symbols are used. Numbers indicate amino acid positions in relation to the complete protein.

FIG. 2A compares RIZ amino acid sequences with various E1A sequences. E1A sequences of the different strains of adenoviruses are from Kimelman et al., *J. Vir.*, 53:399–409 (1985), Moran and Mathews, *Cell*, 48:177–178 (1987), and Ishino et al., *Vir.*, 165:95–102 (1988). Identical or closely related residues are boxed. Single letter amino acid symbols are used. Sequence domains, RIZ cr1 (SEQ ID NO: 79), Ad2E1A cr1 (SEQ ID NO: 44), Ad5 cr1 (SEQ ID NO: 45), Ad7 cr1 (SEQ ID NO: 46), Ad12 cr1 (SEQ ID NO: 47), EA7 cr1 (SEQ ID NO: 48), Ad40 cr1 (SEQ ID NO: 49), RIZ cr2 (SEQ ID NO: 65), Ad2E1A cr2 (SEQ ID NO: 66), Ad5 cr2 (SEQ ID NO: 67), Ad7 cr2 (SEQ ID NO: 68), Ad12 cr2 (SEQ ID NO: 69), EA7 cr2 (SEQ ID NO: 70), Ad40 cr2 (SEQ ID NO: 71), RIZ ce1 (SEQ ID NO: 72), Ad2E1A ce1 (SEQ ID NO: 73), Ad5 ce1 (SEQ ID NO: 74, Ad7 ce1 (SEQ ID NO: 75), Ad12 ce1 (SEQ ID NO: 76), EA7 ce1 (SEQ ID NO: 77) and Ad40 ce1 (SEQ ID NO: 78) are shown.

FIG. 2B shows RIZ putative SH3 and SH3-binding domains. Panel a: Sequence comparison of RIZ with other known SH3 domain-containing proteins (Lowenstein et al., Cell, 70:431–442 (1992)). Identical or closely related residues are boxed and the phosphate-binding loop in RIZ (SEQ ID NO: 80) is underlined. Sequences from GRB2 N-terminus (SEQ ID NO: 50), GRB2 C-terminus (SEQ ID NO: 51), P85 (SEQ ID NO: 52), v-abl (SEQ ID NO: 53), c-src (SEQ ID NO: 54), GAP (SEQ ID NO: 55), PLC (SEQ ID NO: 56) and v-crk (SEQ ID NO: 57) are shown. Panel b: A RIZ putative SH3-binding motif compared with SH3 motifs from known SH3-binding proteins (Ren et al., Science 259: 1157–1161 (1993)). Identical or closely related residues are boxed. Sequences from RIZ (SEQ ID NO: 81) Formin (SEQ ID NO: 58), 3BP1 (SEQ ID NO: 59), 3BP2 (SEQ ID NO: 60) and m4mAChR (SEQ ID NO: 61) are shown.

FIG. 2C shows homology between RIZ and PRDI-BF1 proteins (Keller and Maniatis, Genes Devel., 5: 868–879 (1991)). Panel a: Alignment of RIZ zinc fingers 4 to 6 (SEQ ID NO: 82) with PRDI-BF1 zinc fingers 1 to 3 (SEQ ID NO: 62). A consensus sequence is shown with nonidentical residues indicated by dots. Potential DNA contact residues are marked by stars (Pavletich and Pabo, Science, 252: 809–817 (1991)). Panel b: Amino terminal homology between RIZ (a.a. position 39-115; SEQ ID NO: 83 and a.a. position 116-145: SEQ ID NO: 84) and PRDI-BF1 (a.a. position 60-139: SEQ ID NO: 63 and a.a. position 140-169: SEQ ID NO: 64)). A consensus sequence is shown with nonidentical residues indicated by dots.

FIG. 4 demonstrates that $^{35}$S-labeled RIZ (a.a. position 1–575) specifically binds to Rb in vitro. Binding assays were performed in the absence or presence of peptides derived from RIZ or SV40 large T antigen. T-pep: peptide of large T antigen (a.a. position 101-118); T-pep*: single amino acid residue mutant of T-pep ($107^{Glu}$); RIZ-pep: peptide of RIZ (a.a. position 304-314); RIZ-pep*: single amino acid mutant of RIZ pep ($307^{Gly}$).

FIG. 5A and 5B Use of Rb deletion mutants to map the RIZ binding site of Rb.

FIG. 5A Purified glutationine S-transferase fusion protein containing a C-terminal RIZ fragment (a.a. position 245-573) was tested for binding to $^{35}$S-labeled Rb wild-type (wt-Rb) and to various deletion mutants (lanes 2–5) as shown in FIG. 5B Wild-type (wt) full length Rb (A9), Cys to Phe mutation of full length Rb (H209), Rb deletion mutants from amino acid positions 515-619 (NM), 585-697 (PP) and 804-928 (B3) are shown.

FIG. 5B Schematic map of Rb wild-type (wt-Rb) and Rb deletion mutants. The two sub-domains of the Rb pocket are represented by black boxes. Mutants that bind a glutathionine S-transferase (GST) RIZ (a.a. position 245-573) are indicated by a "+" sign. p56 Rb: 56 kD fragment of Rb from a.a. position 379-928.

FIG. 7A SDS-PAGE (10% acrylamide) and Coomassie blue staining of GST; GSTZ13: GST-RIZ (a.a. position 245-573 containing zinc fingers 1–3); and GSTZ46: GST-RIZ (a.a. position 1114-1260 containing zinc fingers 4 to 6). KD indicates the migration of molecular weight markers.

FIG. 7B Binding of $^{32}$P-labeled rat genomic DNA to GST, GSTZ13 and GSTZ46 in the presence of zinc ions.

FIG. 7C As in FIG. 6B, except zinc ions were not added.

FIG. 8A SDS-PAGE (10% acrylamide) and Coomassie blue staining of purified GST-G: GST-RIZ (760-949: RIZ GTPase domain fused C-terminal to glutathionine S-transferase).

FIG. 8B $^{32}$P-GTP binding by GST (lane 1) and GST-G (lanes 2–6). Binding conducted in the absence or presence (lanes 3–6) of excess unlabeled nucleotides as indicated.

FIG. 9 shows the nucleotide sequence (SEQ ID NO: 3) and deduced amino acid sequence (SEQ ID NO: 4) of full-length human RIZ. Single letter amino acid symbols are used. Numbers at right indicate the nucleotide position.

FIG. 10 compares the complete human RIZ amino acid sequence (indicated as hRIZ; SEQ ID NO: 4) with the complete rat RIZ amino acid sequence (indicated as rRIZ; SEQ ID NO: 2). A consensus sequence is shown. Single letter amino acid symbols are used. Amino acids that are identical in hRIZ and rRIZ are shown as a ".".

FIG. 11A presents a northern blot of adult mRNA probed with $^{32}$P-labeled rat RIZ (1.9 Kb fragment representing a.a. position 245-883). Att-20 is a mouse pituitary cell line.

FIG. 11B presents an RNase protection experiment using RNA from a 16 day fetal rat (E16) and from an adult rat probed with $^{32}$P-labeled rat RIZ (representing a.a. position 463-574).

DETAILED DESCRIPTION OF THE INVENTION

Figure 3:
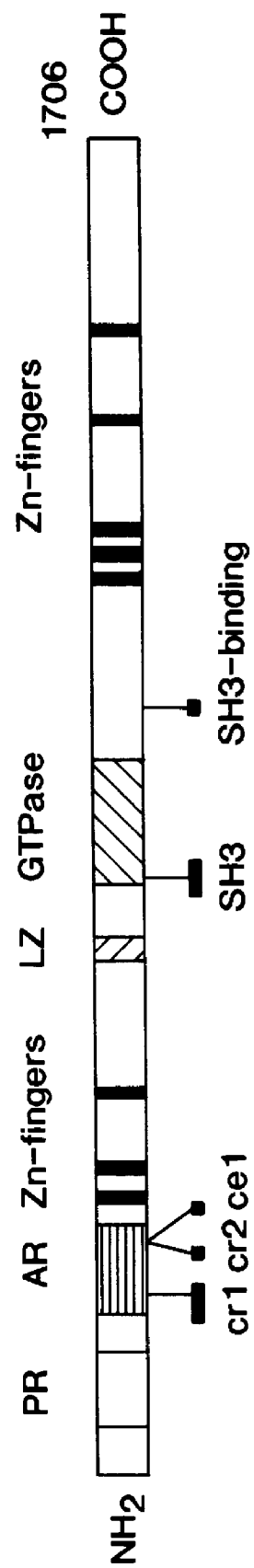
FIG. 3 Schematic representation of RIZ domain structure. PR: domain homologous to PRDI-BF1; AR: acidic region or E1-related region; LZ: leucine-zipper; cr1 and cr2: conserved regions 1 and 2; ce1: common epitope 1. Zinc (Zn—) fingers, GTPase and SH3 and SH3-binding domains also are shown.

The present invention provides a novel mammalian Rb-interacting zinc finger protein, designated RIZ. RIZ is a nuclear phosphoprotein that acts as a cell differentiation factor. RIZ can modulate a function of a cell by binding to retinoblastoma (Rb) protein, which is involved in regulating cell proliferation.

Rb is a nuclear phosphoprotein of 110 kiloDaltons (kD) that can bind DNA and is expressed in all tissue types examined thus far. The complete absence of Rb function is associated with the development of childhood retinoblastoma. In addition, Rb is mutated in a variety of cancer types, including various carcinomas and sarcomas, indicating a role for Rb in oncogenesis. Expression of exogenous Rb in various types of tumor cells suppresses the tumor phenotype (for review, see Lee et. al., *J. Cell Biochem.* 38:213–227 (1988)).

The function of Rb at the biochemical level in a cell is poorly understood. Rb is present in phosphorylated and unphosphorylated forms in the cell. The phosphorylation status of Rb oscillates during the cell cycle with the hypophosphorylated form correlating with the maintenance of the cell in $G_1$ phase of the cell cycle. Thus, the state of phosphorylation plays an important role in Rb function.

Rb protein binds to several DNA tumor viral oncoproteins, including the adenoviral E1A protein, the SV40 large T antigen and the E7 protein of the human papilloma virus (DeCaprio et al., *Cell* 54:275–283 (1988); Whyte et al., *Cell* 56:67–75 (1989); Dyson et al., *Science* 243:934–937 (1989)). The oncoproteins E1A and large T antigen bind to a similar region of Rb protein known as the Rb pocket, which is formed by two non-contiguous amino acid sequences in the protein (Hu et al., *EMBOJ.* 9:1147–1155 (1990); Huang et al., *EMBOJ.* 9:1815–1822 (1990); Kaelin et al., *Mol. Cell. Biol.* 10:3761–3769 (1990), each of which is incorporated herein by reference). The binding to Rb by these viral oncoproteins can alter normal Rb function.

As disclosed herein, RIZ is a normal cellular protein that binds to the Rb pocket. RIZ binding to Rb is unlike that of an oncoprotein since RIZ functions as a differentiation factor that helps to maintain cells in the $G_0$ or $G_1$ phases of the cell cycle. This is based on the fact that RIZ can bind to Rb in the cell, the latter being a known regulator of cell proliferation and differentiation, and that RIZ is structurally related to a known differentiation and transcription factor PRD1-BF1/Blimp-1 (Huang, *Cell*:78, 9 (1994)).

The ability to regulate cell growth has important implications for various human diseases or conditions. Cancer is an example of a disease that results from a breakdown in the ability of a cell to regulate its growth. In contrast, there are examples such as cardiac muscle cells and neural cells where the maintenance of cell growth control contributes to a sustained loss in organ or tissue function following a disease or injury that resulted in cell death. In these situations, the compromised tissue or organ fails to regenerate fully because the remaining live cells are incapable of undergoing proliferation to replace the lost function.

Heart disease provides an example where cardiac muscle cell death due to ischemia or other injury results in a loss of heart function. Generally, proliferation of the remaining live cardiac cells to regenerate the lost cardiac muscle function does not occur in adults. Although myocardial cell proliferation can occur during embryonic and neonatal development, this capacity to proliferate is lost soon after birth. In a similar manner, neural damage resulting from trauma or disease is not usually followed by regeneration of neural function because the remaining neural cells are maintained in the $G_1$ phase of the cell cycle. Transcriptional regulators such as Rb play an important role in controlling whether cells can enter the cell cycle and proliferate. In contrast, inactivation of Rb is involved in the unregulated growth of a cancer cell.

As disclosed herein, RIZ can bind to Rb and can regulate the ability of Rb to maintain cells in the $G_1$ phase of the cell cycle. Methods that affect the ability of Rb and RIZ to associate or that affect the activity of a RIZ can be used to modulate cell proliferation. RIZ can regulate the growth of normal adult cardiac muscle cells by preventing the cells from proliferating following cardiac muscle cell death. RIZ can function to maintain cells in $G_1$ by interacting with Rb through the cr2 domain of RIZ. In addition, the functional differentiation state of a cell, which involves maintenance of a cell in $G_1$, is affected, in part, through the action of other RIZ domains such as the PR domain, GTP binding domain and the zinc finger domains.

Figure 1A-1:
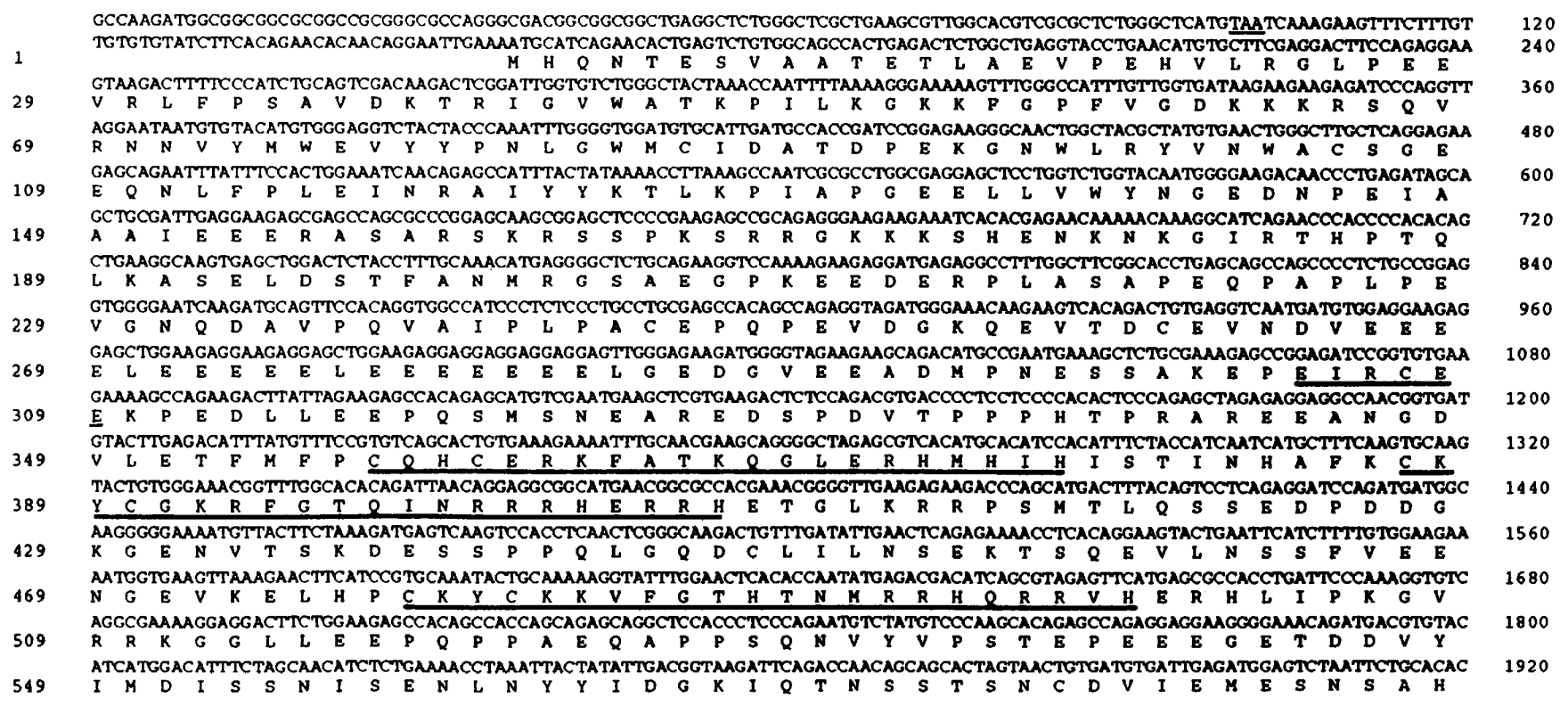

The present invention provides a substantially purified RIZ protein that binds to Rb. The invention provides, for example, human RIZ having substantially the amino acid sequence shown in FIG. 9 (SEQ ID NO: 4) and rat RIZ having substantially the amino acid sequence shown in FIG. 1 (SEQ ID NO: 2).

As used herein, the term "substantially the amino acid sequence" means a sequence that is similar to the disclosed amino acid sequence. For example, an amino acid sequence that is substantially similar to human RIZ (SEQ ID NO: 4) or to rat RIZ (SEQ ID NO: 2) can have one or more amino acid additions, deletions or substitutions that do not substantially alter the ability of the encoded protein to function like a RIZ. In view of this definition, it should be recognized, for example, that the rat RIZ sequence shown in FIG. 1 (SEQ ID NO: 2), which is 84% homologous to the human RIZ sequence has substantially the amino acid sequence of human RIZ (SEQ ID NO: 4). Similarly, the rat RIZ cr2 sequence EIRCEEKPEDL (SEQ ID NO: 6) is substantially the sequence of the human RIZ cr2 motif, EIRCDEKPEDL (SEQ ID NO: 79). The latter two sequences differ by a single conservative substitution of a Glu in the rat for an Asp in the human in the residue following the Cys.

As used herein, the term "substantially purified" means a protein that is in a form that is relatively free from contaminating lipids, proteins, nucleic acids or other cellular material normally associated with a protein in a cell. A substantially purified human RIZ protein can be obtained, for example, using well known biochemical methods of purification or by expressing a recombinant nucleic acid molecule encoding a RIZ such as the nucleic acid molecule shown as SEQ ID NO: 3. In addition, an amino acid sequence consisting of at least a portion of the amino acid sequence of SEQ ID NO: 4 can be chemically synthesized or can be produced by expressing a portion of the nucleotide sequence shown as SEQ ID NO: 3.

As used herein, the terms "protein" or "polypeptide" are used in the broadest sense to mean a sequence of amino acids that can be encoded by a cellular gene or by a recombinant nucleic acid sequence or can be chemically synthesized. In some cases, the term "polypeptide" is used in referring to a portion of an amino acid sequence encoding a full length protein. An active fragment of a RIZ is an example of such a polypeptide. A protein can be a complete, full length gene product, which can be a core protein having no amino acid modifications, or can be a post-translationally modified form of a protein such as a phosphoprotein, glycoprotein, proteoglycan, lipoprotein or nucleoprotein.

Figure 1A-2:
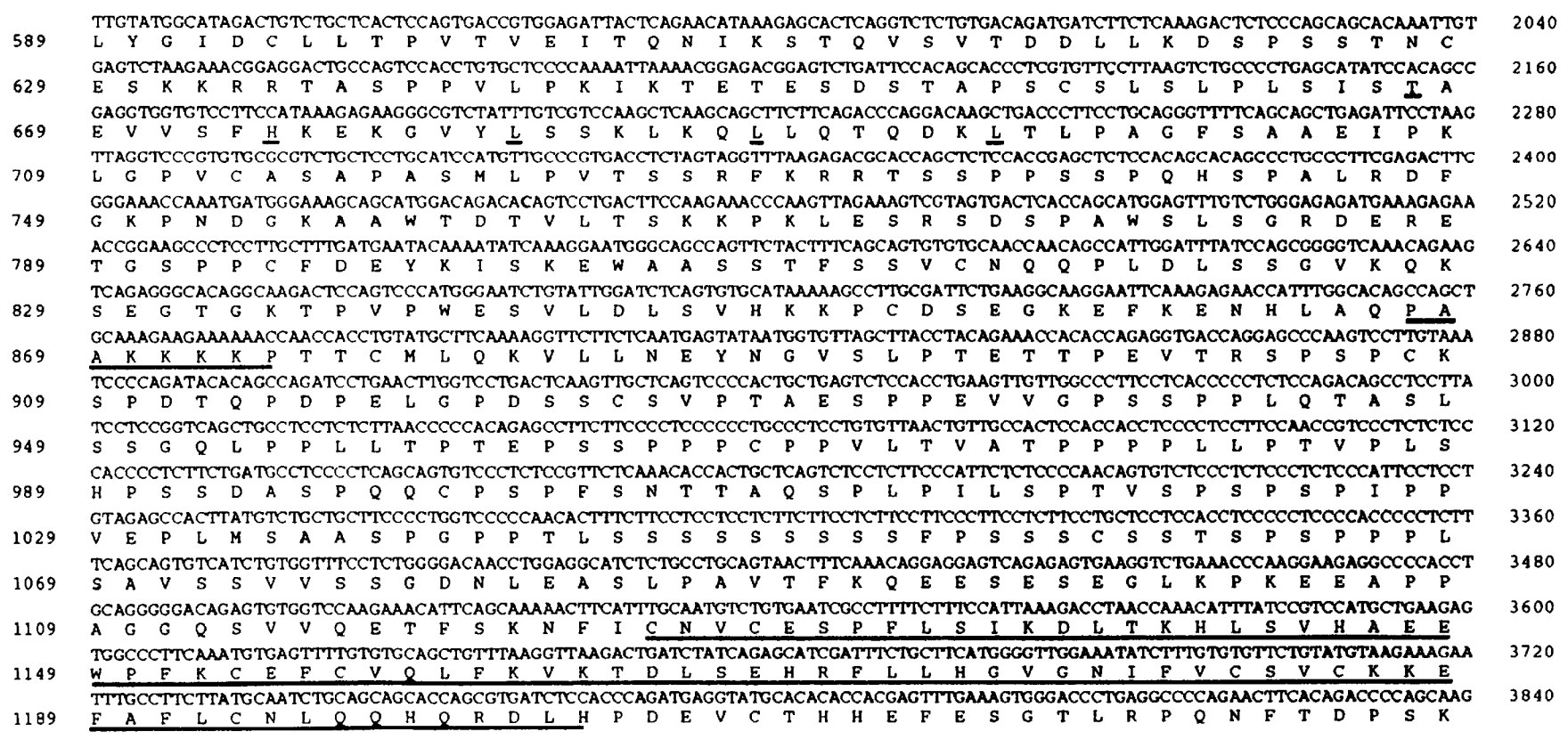
Figure 1A-3:
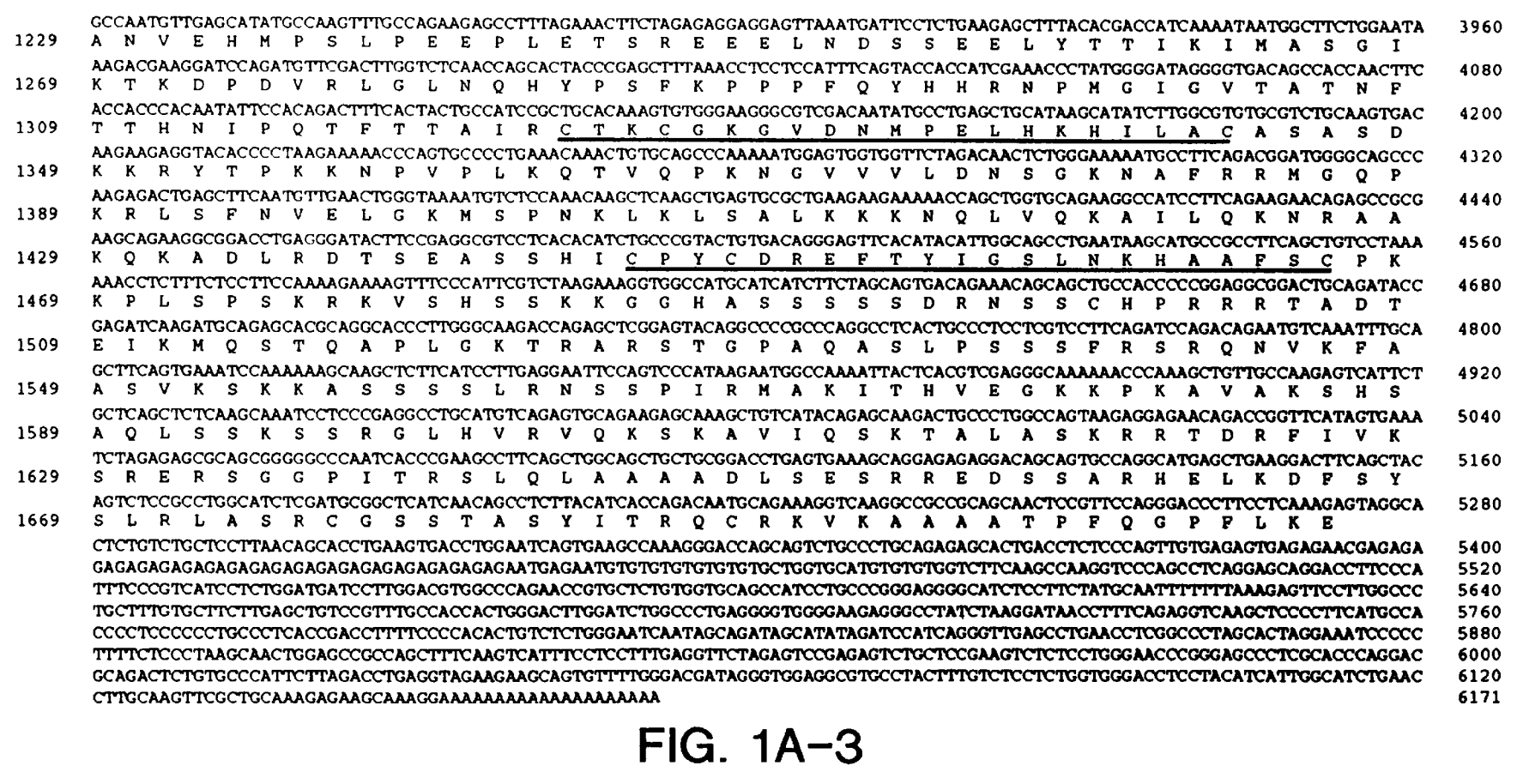

The full length rat RIZ protein contains 1706 amino acids and has a calculated molecular mass of 187,437 Daltons (FIG. 1; SEQ ID NO: 2). The rat RIZ contains a 6 residue E1A related motif (a.a. position 304-309) known as the cr2 core motif, which is related to the LXCXE (SEQ ID NO: 5) core motif of E1A. Additional E1A related motifs in RIZ include the cr1 motif and a C-terminal motif designated "conserved epitope 1" (ce1) because of its antigenic relationship to a homologous motif in the C-terminus of E1A (see Example II). Rat RIZ also contains 8 zinc fingers, a putative GTPase domain, a putative leucine zipper and a putative nuclear localization signal (FIGS. 1 and 3).

All three E1A-related motifs in rat RIZ are located in an acidic region that consists of about 150 residues (AR; FIG. 3) and resembles a highly acidic region in the E1A 12S protein (Moran and Matthews, Cell, 48:177–178 (1987)). In both RIZ and E1A, the related motifs are arranged in the same order and the spacing between cr1 and cr2 is similar. However, the ce1 motif is located much closer to cr2 in RIZ than in E1A (see FIG. 2A).

The rat RIZ protein sequence contains known GTPase motifs (Table 1) organized in an orderly fashion and separated by consensus spacings (Bourne et al., Nature 349:117–127 (1991)). The G1 or Walker type-A motif (GX$_4$GKX$_7$(I/V); SEQ ID NO: 14), which represents the phosphate-binding loop (P-loop), occurs at a.a. position 749 in RIZ and identifies a guanine or adenine nucleotide-binding site (Walker et al., EMBO J. 1: 945–951 (1982); Saraste et al., Trends Biochem. Sci. 15: 430–434. (1990)). The sequence around residue 749 also is similar to the src homology 3 (SH3) domain conserved in many non-receptor tyrosine kinases and other proteins (FIG. 2B panel a); Pawson and Gish, Cell 71:359–362 (1992)). RIZ also contains a proline-rich region that has several potential SH3-binding motifs (FIG. 2B, panel b); Renet al., Science, 259:1157–1161 (1993)).

TABLE 1

Putative GTPase Domain in RIZ

|  | G1 | G2 | G3 | G4 |
|---|---|---|---|---|
| Consensus | GXXXXGK$_T^S$ | D(X)$_n$T | DXXG | $_{TQ}^{NK}$XD |
|  | *(22) |  | (23) | (24) |
| RIZ | $^{749}$GKPNDGKA | $^{785}$DERET | $^{853}$DSEG | $^{912}$TQPD |
|  | (85) | (86) | (89) | (90) |
|  |  | $^{796}$D(X)$_{12}$T |  |  |
|  |  | (87) |  |  |
|  |  | $^{821}$D(X)$_{11}$T |  |  |
|  |  | (88) |  |  |
| FtsZ | $^{106}$GGTGTGAA | $^{122}$DLGILT | $^{180}$DAFG | $^{295}$TSLD |
|  | (25) | (26) | (29) | (31) |
|  |  | $^{158}$DSLIT | $^{253}$DLSG |  |
|  |  | (27) | (30) |  |
|  |  | $^{212}$DVRT |  |  |
|  |  | (28) |  |  |
| CDC42 | $^{10}$GDGAVGKT | $^{32}$YVPT | $^{57}$DTAG | $^{115}$TQID |
|  | (32) | (33) | (34) | (35) |
| DOG-SR2 | $^{419}$GVNGVGKS | $^{455}$DT | $^{516}$DTAG | $^{584}$TKFD |
|  | (36) |  | (34) | (37) |
| EF-Tu | $^{13}$GHVDHGKT | $^{50}$D(X)$_{10}$T | $^{80}$DCPG | $^{135}$NKCD |
|  | (38) | (39) | (40) | (41) |
| Ha-Ras | $^{10}$GAGGVGKS | $^{33}$DPT | $^{57}$DTAG | $^{116}$NKCD |
|  | (42) | (43) | (34) | (41) |

Comparison of the putative G1–G4 GTPase domains in the RIZ protein sequence with the conserved sequence motifs in the GTPase superfamily (single letter code and X is any residue, Bourne et al., 1991). For reference to the listed sequences (except RIZ and FtsZ) see Bourne et al. (1991). For reference to FtsZ, see Ray Chaudhuri and Park (1992).
*Number in parenthesis below each sequence indicates SEQ ID NO:.

Sequence homology shows that a mammalian RIZ protein contains eight zinc-finger motifs organized as two widely separated clusters in the N-terminal (fingers 1 to 3) and C-terminal (fingers 4 to 6) regions (FIG. 3). A search of the National Biomedical Research Foundation protein database revealed that the most significant homology for zinc fingers was for RIZ fingers 4 to 6, which are about 39% (33 out of 85) identical to fingers 1 to 3 of the human transcriptional repressor PRDI-BF1 (see FIG. 2C; Keller and Maniatis, supra, 1991). RIZ also contains a region of about 100 residues near the N-terminus that is designated "PR" because it is 42% homologous with a similar N-terminal region from PRDI-BF1 (see FIG. 2C) and Blimp-1 (Huang, supra, 1994).

Human RIZ was cloned from human cDNA and genomic DNA libraries using the rat RIZ cDNA as a hybridization probe. The human RIZ cDNA (SEQ ID NO: 3) encodes a polypeptide having 1719 amino acid residues (see FIG. 9 for a.a.; SEQ ID NO: 3). The human RIZ gene coding region is encoded by eight exons and is located on chromosome 1p36 (see Example VI).

Allelic variants of the human RIZ gene are disclosed herein. The RIZ E283 allele contains a Glu residue at a.a. position 283, while the RIZ D283 allele contains an Asp residue at a.a. position 283 (SEQ ID NO: 4). The basis for the amino acid difference is a single nucleotide change of T$_{849}$ in the RIZ D283 to an A$_{849}$ in RIZ E283. The RIZ D283 allele is estimated to occur two times more frequently in the human population than the RIZ E283 allele.

The deduced rat and human RIZ amino acid sequences are 84% homologous. Both the rat and human RIZ proteins have similar sequence motifs including cr1, cr2, ce1, zinc finger, SH3, SH2 and a nuclear localization signal. Both rat and human RIZ proteins are similar in size; rat RIZ contains 1706 amino acids and has a calculated molecular weight of 187,437 Daltons while human RIZ contains 1719 amino acids and has a calculated molecular weight of 188,894 Daltons. In addition, a rabbit antiserum produced against rat RIZ (see Example II) crossreacts with human RIZ.

RIZ is expressed primarily in the cell nucleus. RIZ mRNA is expressed primarily in cells of neuroendocrine origin and is expressed in greater amounts in the fetus than in the adult (see FIGS. 10 and 11). RIZ is expressed in rat cells as a 250 kD phosphoprotein.

Figure 9A:
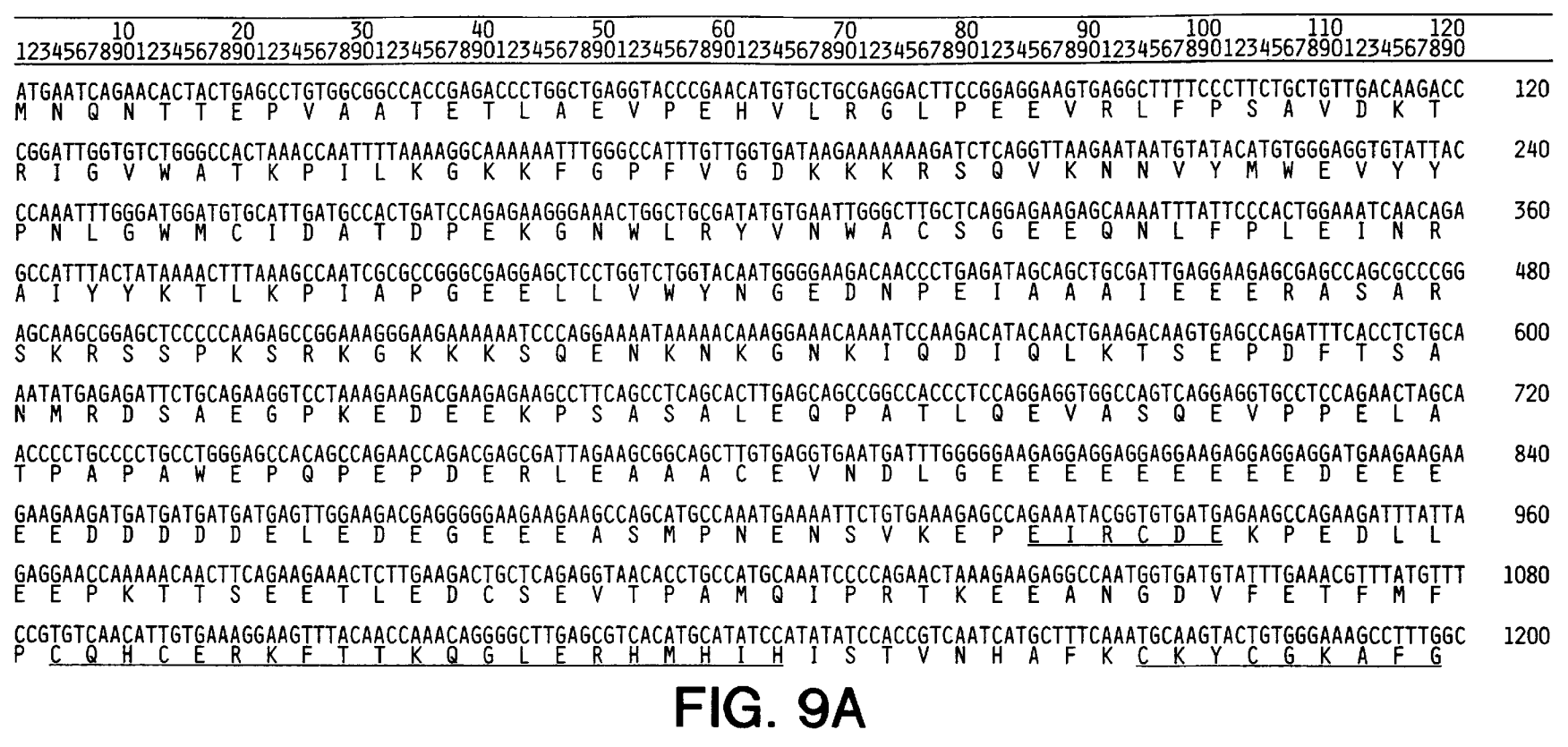
Figure 9B:
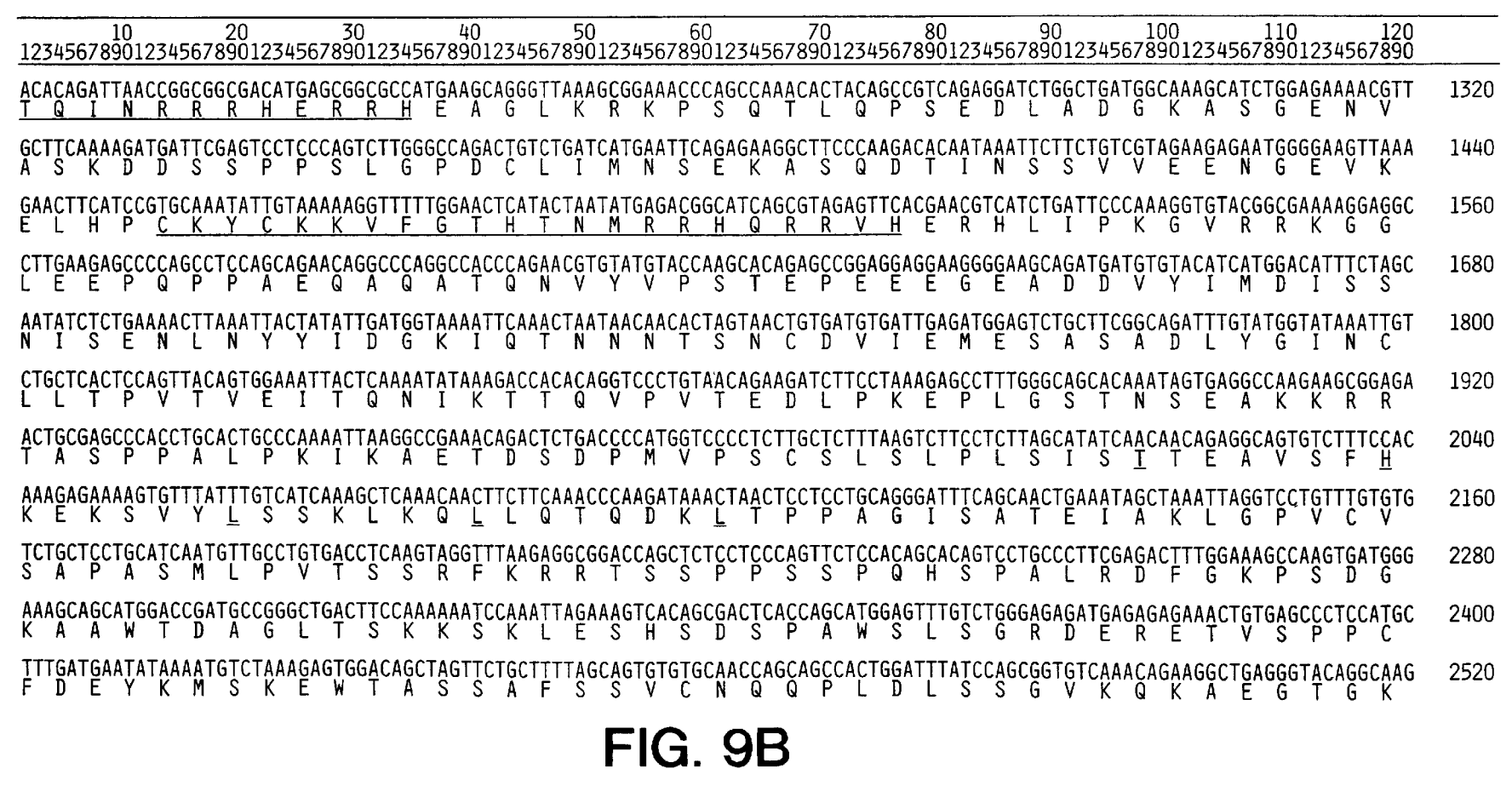
Figure 9D:
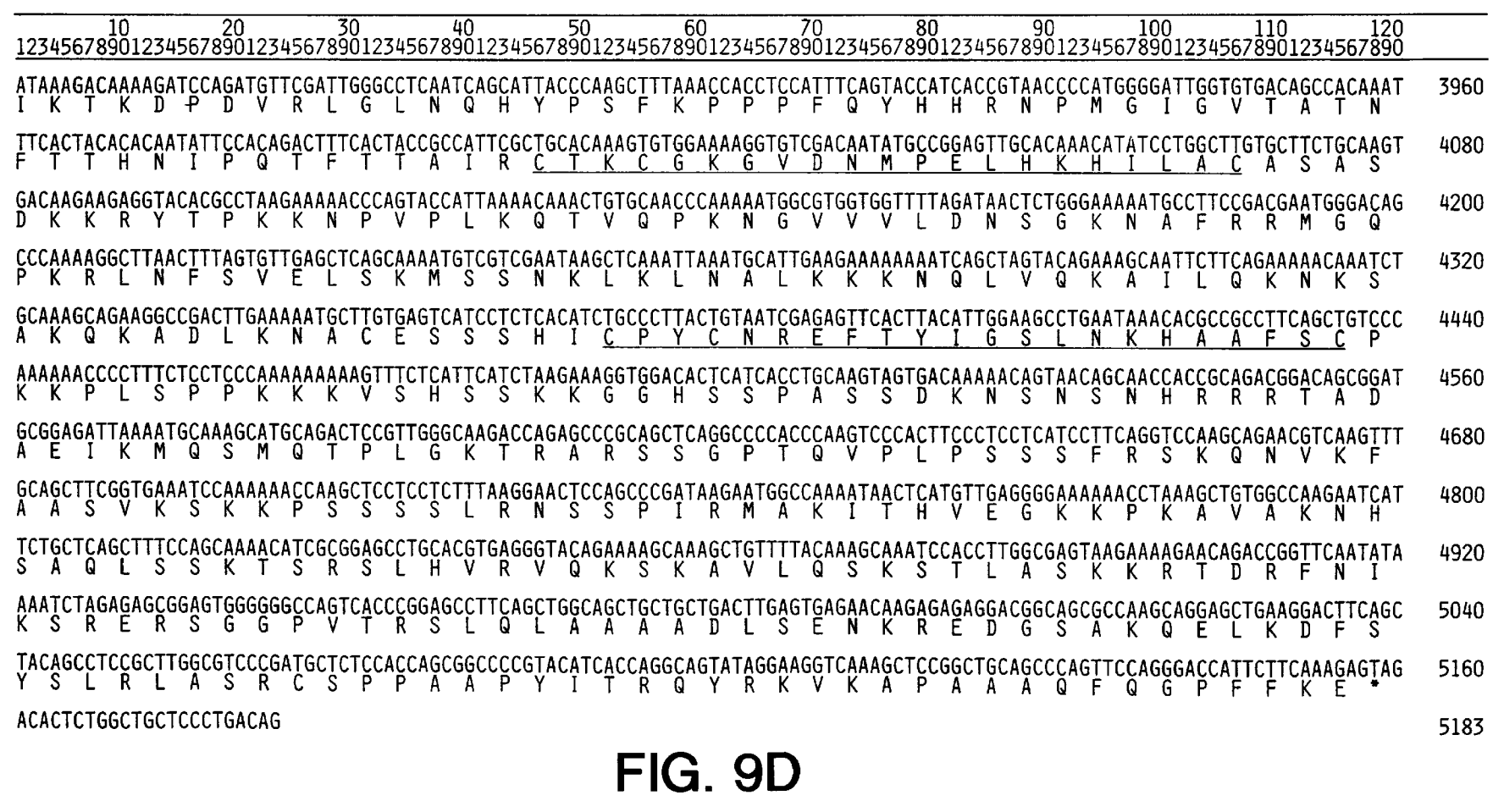

As used herein, the term "RIZ" means a protein having substantially the amino acid sequence of human RIZ as shown in FIG. 9 (SEQ ID NO: 4) or of rat RIZ as shown in FIG. 1 (SEQ ID NO: 2). The term "RIZ" is meant to include normal variants such as the allelic variants disclosed herein. Such normal variants can differ in amino acid sequence but share the same or similar functional activities such as binding to GTP, DNA or Rb (see Examples). A RIZ is referred to as a "normal RIZ" or a "wild-type RIZ", all of which are distinct from a mutant RIZ. In addition to the allelic variants, RIZ also can be a truncated RIZ protein encoded by a subset of the RIZ exons and that functions like a RIZ. Such a variant RIZ can be generated in the cell by alternative RNA splicing.

The term "RIZ" also includes peptide fragments of a RIZ, including active fragments of a RIZ. As used herein, the term "active fragment" means a peptide portion of a full length RIZ protein that has at least one activity that is characteristic of the corresponding full length protein. A peptide portion of a rat RIZ having the sequence EIRCEEKPEDL (SEQ ID NO: 6) or a peptide portion of a human RIZ having the sequence EIRCDEKPEDL (SEQ ID NO: 91) are examples of active fragments of a RIZ that can bind to Rb. Other RIZ activities that can be associated with an active fragment of a RIZ include the ability to bind DNA in a zinc ion-dependent manner, the ability to bind GTP or an anti-RIZ antibody, or the ability to act as a hapten or immunogen to obtain an anti-RIZ antibody.

The present invention provides an active fragment of a RIZ containing substantially the amino acid sequence of the RIZ cr2 motif, EIRCEEKPEDL (SEQ ID NO: 6), or EIRCDEKPEDL (SEQ ID NO: 91), where the cysteine residue is required when the activity of the fragment is Rb binding. The cr2 motifs of human RIZ or rat RIZ are examples of active fragments of a RIZ (see FIG. 10). Such active fragments can be produced by recombinant DNA methods, by peptide synthesis or by enzymatic cleavage of a RIZ protein. The present invention also provides a non-naturally occurring polypeptide having incorporated therein a RIZ cr2 core motif. Such a polypeptide can be produced using well known recombinant DNA methods.

A RIZ protein or a RIZ polypeptide containing the cr2 motif such as the amino acid sequences EIRCEEKPEDL (SEQ ID NO: 6) and EIRCDEKPEDL (SEQ ID NO: 91) can bind to Rb and, therefore, is useful for isolating Rb from a sample. Purified Rb can be used, for example, as a control target in a diagnostic test to detect whether a subject has a mutated Rb. Additionally, Rb can be used as a reagent to detect whether a sample has a RIZ which can bind to Rb or a mutant RIZ that fails to bind Rb. Mutations that affect the function of Rb and are diagnostic for cancer are well known in the art (see, for example, Lee et al., In *Tumor Suppressor Genes*, Chapter 11, Marcell Decker (1990).

To purify Rb, RIZ protein can be contacted with the Rb containing sample under suitable conditions, which allow formation of a RIZ-Rb complex. Suitable conditions for complex formation can be determined empirically and include, for example, an appropriate buffer concentration and pH and time and temperature of incubation that permit binding of the RIZ to Rb. The RIZ-Rb complex can be separated from unbound material in the sample and Rb can be dissociated from the complex and obtained in substantially purified form.

Substantially purified Rb can be obtained, for example, by using affinity chromatography, in which a RIZ is bound to a solid support, the sample is applied to the support to allow binding of Rb to the RIZ, the support is washed to remove unbound material and Rb is eluted from the support. Useful solid supports include, for example, agarose, Sepharose™ or plastic. RIZ can be attached to a solid support by direct chemical coupling or by an indirect means such as an affinity interaction with an anti-RIZ antibody bound to the support. Other indirect means for coupling a RIZ to a support include incorporating one entity of a known ligand/receptor pair into the RIZ, with the corresponding entity coupled directly to the support. For example, biotin can be coupled to RIZ and avidin can be coupled directly to a solid support to bind the RIZ to the support. Also, RIZ can be expressed as a fusion to glutationine S-transferase (see Example II) and the fusion protein can be bound to a glutathionine coupled support.

The present invention also provides a RIZ binding reagent. As used herein the phrase "RIZ binding reagent" means a chemical or biological molecule that specifically binds to a RIZ. As used herein with reference to a RIZ, the term "specifically binds" means that under a defined set of conditions, the RIZ binding reagent interacts with a RIZ but not with an unrelated molecule or with a mutant RIZ. Rb and anti-RIZ antibody are examples of a RIZ binding reagent.

The invention also provides a mutant RIZ binding reagent. As used herein, the phrase "mutant RIZ binding reagent" means a chemical or biological molecule that specifically binds to a mutant RIZ but not to a wild-type RIZ. In this case, the mutant RIZ binding reagent, under a defined set of conditions, interacts with the mutant RIZ but not with a wild-type RIZ.

Rb and an antibody specific for a RIZ are examples of reagents that can specifically bind to a RIZ. As used herein, the term "antibody" is used in its broadest sense to include polyclonal and monoclonal antibodies, as well as polypeptide fragments of antibodies that retain a specific binding activity for a specific antigen of at least about $1 \times 10^5$ M$^{-1}$. One skilled in the art would know that a fragment such as Fab, F(ab')$_2$, Fv and Fd fragments of an anti-RIZ antibody, for example, can retain specific binding activity for a RIZ and, thus, is included within the definition of an antibody. In addition, the term "antibody" as used herein includes naturally occurring antibodies as well as non-naturally occurring antibodies and fragments of antibodies that retain binding activity. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference.

An antibody specific for a RIZ can be prepared using well known methods as described, for example, by Harlow and Lane, *Antibodies: A laboratory manual* (Cold Spring Harbor Laboratory Press, 1988), which is incorporated herein by reference. For example, RIZ protein or a portion of the RIZ protein can be used as an immunogen, which can be prepared from natural sources or produced recombinantly or, in the case of a portion of the RIZ protein, can be chemically synthesized. Non-immunogenic peptides of RIZ protein can be made immunogenic by coupling to a carrier molecule such as bovine serum albumin or keyhole limpet hemocyanin as described, for example, by Harlow and Lane, supra, 1988. In addition, a RIZ fusion protein can be expressed as described in Example II. Such a fusion protein can be readily purified and used as an immunogen (see Example II). These methods can be used to produce various anti-RIZ antibodies.

Polyclonal antibodies can be raised, for example, in rabbits or goats. In addition, monoclonal antibodies can be obtained using well known methods (see, for example, Reed et al., *Anal. Biochem.* 205:70–76 (1992)), which is incorporated herein by reference; see, also, Harlow and Lane, supra, 1988). For example, spleen cells from a RIZ immunized mouse can be fused to an appropriate myeloma cell line such as SP2/0 or P3x653.Ag8 myeloma cells to produce hybridoma cells. Cloned hybridoma cell lines can be screened using a labeled RIZ immunogen to identify clones that secrete monoclonal antibodies. Hybridomas that express antibodies having a desirable specificity and affinity can be isolated and utilized as a continuous source of antibodies. A dependable source of monoclonal antibodies is desirable, for example, for preparing diagnostic kits as described below.

An antibody specific for a mutant RIZ protein also can be prepared using the above methods by immunizing with either the full-length mutant RIZ protein or with a fragment of the protein containing the mutation. Methods to direct the immune response to the mutant sequence also are well known in the art and include, for example, use of particular adjuvants or pre-prior tolerization of the animal to the wild-type RIZ sequence. Such tolerization can be performed by immunizing the animal with the wild-type RIZ in conjunction with administration of anti-T cell antibodies or immunosuppressive drugs. A monoclonal antibody to the mutant sequence can be obtained by screening a population of hybridomas for those that express an antibody that binds the mutant RIZ sequence but not a wild-type RIZ sequence.

The invention also provides a substantially purified nucleic acid molecule, which encodes a RIZ such as a mammalian RIZ. For example, the invention provides substantially purified nucleic acid molecules having substantially the nucleotide sequences encoding human RIZ and rat RIZ as shown in FIG. 9 (SEQ ID NO: 3) and FIG. 1 (SEQ ID NO: 1), respectively.

As used herein, the term "substantially purified nucleic acid molecule" means a nucleic acid molecule that is in a form that is relatively free from contaminating lipids, proteins, nucleic acids or other cellular material normally associated with a nucleic acid molecule in a cell. A substantially purified nucleic acid molecule can be obtained, for example, by recombinant DNA methods as described herein (see, also, Sambrook et al., *Molecular Cloning: A laboratory manual* (Cold Spring Harbor Laboratory Press 1989), which is incorporated herein by reference) or can be chemically synthesized.

As used herein with reference to a RIZ, the term "substantially the nucleotide sequence" means, for example, the disclosed nucleotide sequence for human RIZ (SEQ ID NO: 3), as well as a similar sequence that contains, for example, different nucleotides than shown in SEQ ID NO: 3, but that, as a result of the degeneracy of the genetic code, encodes the same amino acid sequence as shown in SEQ ID NO: 4. In addition, the rat RIZ nucleotide sequence (SEQ ID NO: 1) is considered to be substantially similar to the nucleotide sequence encoding human RIZ (SEQ ID NO: 3). For convenience, the coding strand for a nucleic acid molecule encoding a RIZ is shown. It should be recognized, however, that the complementary strand also is encompassed within the disclosed nucleic acid molecules. Thus, unless otherwise indicated, reference herein to a nucleic acid molecule or to a nucleotide sequence is meant to include the complementary sequence.

A nucleic acid molecule of the invention can encode a variant RIZ such as the allelic RIZ variants disclosed herein as well as variants of a RIZ that contain only particular exons of the gene that can be produced in a cell by alternative RNA splicing. In addition, a nucleic acid molecule of the invention can encode a portion of a RIZ such as an active fragment of a RIZ containing the polypeptide EIRCEEKPEDL (SEQ ID NO: 6) and EIRCDEKPEDL (SEQ ID NO: 91), which bind to the Rb pocket.

The invention also provides a nucleotide sequence that specifically hybridizes to a portion of a nucleic acid molecule encoding a mammalian RIZ under relatively stringent hybridization conditions. As used herein with reference to a RIZ, the term "specifically hybridizes" means that under a defined set of hybridization conditions, the nucleotide sequence can interacts with a RIZ encoding nucleic acid molecule but not with an unrelated nucleic acid molecule. A nucleotide sequence that specifically hybridizes to a RIZ can be complementary to a nucleotide sequence encoding a RIZ or can be a RIZ coding sequence or a portion thereof.

A nucleotide sequence that specifically hybridizes to a nucleic acid molecule encoding a RIZ or a mutant nucleic acid molecule encoding a RIZ should be at least ten nucleotides in length and can be prepared, for example, by restriction endonuclease digestion of a cloned nucleic acid molecule encoding a RIZ or by PCR amplification of a portion of the nucleic acid molecule shown in FIG. 1 (SEQ ID NO: 1) or FIG. 9 (SEQ ID NO: 3), or by chemical synthesis.

Relatively stringent hybridization conditions can be determined empirically or can be estimated based, for example, on the relative GC:AT content of the hybridizing nucleotide sequence and the target sequence, the length of the hybridizing nucleotide sequence and the number, if any, of mismatches between the hybridizing nucleotide sequence and the target sequence. If desired, a hybridizing nucleotide sequence can be detectably labeled and used as a probe or can be used as a primer for PCR. Methods for detectably labeling a nucleotide sequence are well known in the art (see, for example, Sambrook et al., supra, 1989; see, also, Ausubel et al., *Current Protocols in Molecular Biology* vol. 2, chapter 10 (Greene Publ., NY 1989), which is incorporated herein by reference).

As used herein, the term "mutant nucleic acid encoding a RIZ" includes nucleic acid molecules having a mutation in an exon, thus encoding a mutant RIZ protein, as well as nucleic acid molecules having a mutation in a region of the RIZ gene other than the exons. A mutation in the RIZ gene occurring outside the exons can involve a regulatory element of the gene that modulates the expression of the RIZ in a cell. Such regulatory elements that can be mutated include, for example, the promoter, enhancer, ribosomal binding site or intron-exon splice junctions. The term "mutant RIZ" also includes peptides of a mutant RIZ, including active fragments of a mutant RIZ.

A mutation that occurs in a regulatory element of the RIZ gene can have a significant impact on the level of expression of a RIZ in a cell. In addition, a mutation in a RIZ exon that codes for a stop codon within the reading frame of the RIZ can produce a truncated RIZ that may be inactive, have an altered activity or be subject to rapid proteolysis in the cell. Similarly, a deletion involving a substantial portion of the gene encoding the RIZ can result in a loss of RIZ expression.

As used herein, the term "mutant RIZ" includes any RIZ having a mutation in a RIZ exon that results in the expression of a RIZ having a functional activity differing from that of a wild-type RIZ normally expressed by a cell. A change in a functional activity characteristic of a mutant RIZ can result from one or more amino acid additions, deletions or substitutions in the wild-type RIZ sequence. Such mutations can arise spontaneously or can be resident in the population and inherited from generation to generation as occurs, for example, with Rb. As disclosed herein, a mutant RIZ can have a change in the nucleotide at position 317 in human RIZ from a G to a C, which results in the expression of a Tyr residue instead of a Cys residue at a.a. position 106.

The present invention also provides a nucleotide sequence that specifically hybridizes to a mutant nucleic acid molecule encoding a RIZ under relatively stringent conditions but not to a wild-type RIZ. In this case, the hybridizing sequence should be complementary to a portion of the RIZ gene containing the mutation.

The expression of a particular RIZ allele can be reduced in a cancer cell due to a mutation in the RIZ gene. As disclosed herein, melanoma tumor cells fail to express mRNA encoding one of two RIZ gene alleles present in the cells (see Example VI). The unexpressed allele likely contains a mutation outside the RIZ coding sequence that affects RIZ expression. Detection of such mutations through the RIZ protein or the RIZ gene can be diagnostic of a pathology such as a cancer.

A mutant RIZ can be obtained, for example, by site directed mutagenesis of a nucleic acid molecule encoding a RIZ, then screening the mutagenized nucleic acid molecule to identify an encoded mutant RIZ. Mutations that affect a functional activity of a RIZ such as Rb binding, DNA binding or GTP binding can be detected by screening for mutants that have lost such activities. Expression in a cell of a mutant RIZ such as mutant human RIZ, which can bind Rb, for example, but lacks a RIZ activity, can alter the association of wild type RIZ with Rb and can affect a function of a cell such as the ability of the cell to proliferate.

The ability of a RIZ to be expressed in the nucleus together with its ability to bind DNA, Rb and GTP (see Example II and IV) and its homology with Blimp-1 (PRD1-BF1) differentiation factor indicates that RIZ can function as a transcriptional regulatory protein or cell differentiation factor. Thus, a function of a cell can be modulated by expressing a RIZ in a cell, where the expressed RIZ can bind to Rb and to DNA in the cell. As used herein, the term, "a function of a cell" means a cell activity, including, for example, proliferation and differentiation. As used herein, the term "modulate" means increase or decrease. As disclosed herein the function of a cell can be modulated due to an altered level of expression of a RIZ or expression of a mutant RIZ in a cell.

The present invention provides methods for modulating a function of a cell by expressing in the cell a DNA sequence encoding a RIZ or an active fragment of a RIZ that can bind to Rb. Such a DNA sequence can be expressed by introducing into a host cell an appropriate expression vector having gene regulatory elements operably linked with the RIZ encoding nucleotide sequence. The expression vector can provide constitutive expression of the polypeptide or, if desired, inducible expression. Expression vectors having the appropriate gene regulatory elements can be purchased from commercial sources or can be constructed using well known methods. For therapeutic purposes, cells can be transfected in tissue culture, then administered to a subject, or a viral vector can be used to introduce a RIZ encoding nucleic acid into a cell in a subject.

As disclosed herein, RIZ can regulate the growth of normal adult cardiac muscle cells and prevent proliferation of surviving cells following cardiac muscle cell death. RIZ can function to maintain cells in the $G_1$ phase of the cell cycle by interacting with Rb through the cr2 domain of RIZ. In addition, the functional differentiation state of a cell, which involves maintenance of a cell in the $G_1$ phase of the cell cycle can be affected through the action of other RIZ domains such as the GTP binding domain and the zinc finger domains.

The regeneration of cardiac muscle cells can be promoted in a subject with cardiac damage by directly decreasing the activity of a RIZ or by decreasing the activity of Rb that occurs subsequent to RIZ binding. The activity of a RIZ can be decreased in such cells by introducing into the cells an expression vector having an expression control sequence operatively linked to a nucleotide sequence encoding a mutant RIZ polypeptide or an active fragment that can bind to Rb but lacks the growth suppressing properties of RIZ. The sequences EIRCEEKPEDL (SEQ ID NO: 6) and EIRCDEKPEDL (SEQ ID NO: 91) are examples of such a peptide.

As used herein, the term "growth suppressing properties of RIZ" means the ability of RIZ to effect the differentiation and the maintenance of cells in $G_1$. In fact, the cell may be in an extended $G_1$ phase or an $G_0$ phase or may be blocked at the $G_0/G_1$ boundary. For convenience, any such cells are referred to as being maintained or suppressed in $G_1$. The growth suppressing or differentiating properties of a RIZ are mediated by regions of the molecule outside the cr2 domain or in conjunction with cr2 that is involved in binding to the Rb pocket.

Neurons, like myocardial cells, normally do not proliferate in the adult. RIZ is preferentially expressed in neural cells (see Example V), indicating a role for RIZ in mediating $G_1$ suppression and differentiation of these cells. The ability to induce proliferation in neural cells can be useful for healing after injury of neural tissue treating neurodegenerative diseases such as Parkinson's disease, Huntington's disease or Alzheimer's disease or paralysis or motor neuron disorders. Thus, the disclosed methods for decreasing the activity of a RIZ protein in a muscle cell similarly can provide a therapy for a neurodegenerative disease.

As disclosed herein, mutations in the nucleotide sequence encoding a RIZ can be involved in the development of cancer such as in melanoma. The frequency of RIZ heterozygosity in melanoma cells versus normal individuals indicates that inactivation of a single RIZ allele is not infrequently found in melanoma (see Example VI). In addition, two of six melanoma cell lines heterozygous for RIZ expressed mRNA for only a single RIZ allele. For such cells, the overall expression of RIZ protein was reduced to about half the level detectable in the other heterozygous RIZ expressing melanoma cell lines. These results indicate that tumor cells such as from a melanoma can be characterized by a reduced level of RIZ protein and, thus, a reduced level of RIZ function. This loss of heterozygosity at the RIZ locus and the reduced expression of the RIZ protein is consistent with other studies showing that loss of heterozygosity of distal chromosome 1p is a late event in melanoma tumor progression that confers a selective growth advantage to the tumor cells (Dracopoli et al., *Proc. Natl. Acad. Sci., USA* 86:4614–4618 (1989)).

The absence of any detectable mutations in the RIZ coding sequence in heterozygous RIZ melanoma cell lines that express only one RIZ allele and the absence of any gross defects in the region near to the RIZ gene indicates that the loss of RIZ expression is due to small mutation in a regulatory region of the gene.

The loss of heterozygosity at the RIZ locus in melanoma can be involved in the increased tumor cell growth associated with melanoma cells having mutations in distal chromosome 1 (Dracopoli et al., supra) and can be responsible for the increased risk of melanoma observed in survivors of heritable retinoblastoma, which occurs without homozygous inactivation of the Rb gene. Since the tumor suppressor function of Rb requires complexing of Rb with an Rb binding protein such as RIZ, a decreased level of Rb-RIZ complex in a tumor cell, resulting from a reduced expression of a RIZ allele, can result in a loss in Rb tumor suppressor activity in the cell.

Further support for the loss of RIZ function and the development of cancer can be provided by the disclosure that RIZ is a differentiation factor. As such, a mutant RIZ can affect the regulation of cell growth by binding to the Rb pocket, a site in the Rb molecule that is involved in regulating cell proliferation. Thus, the present invention provides methods for restoring normal cell growth to a cancer cell that has a mutated or missing RIZ allele by expressing a normal RIZ protein in the cell.

The disclosure that RIZ can modulate a function of a cell by binding to a second molecule such as Rb or a nucleic acid such as DNA or RNA provides a means to identify agents that can effectively alter the association of a RIZ with a second molecule in a cell and, as a result, modulate a function of a cell. Thus, the present invention provides a screening assay useful for identifying an effective agent, which can alter the association of a RIZ with a second molecule.

An effective agent that can decrease the association of a RIZ with a second molecule such as Rb or that can decrease the activity of a RIZ can be useful for releasing a cell from Rb-mediated $G_1$ arrest. Alternatively, an effective agent that increases the association of a RIZ with a second molecule such as Rb or DNA or increases the activity of a RIZ can be useful for reducing the unrestricted growth of a cancer cell by providing a stronger $G_1$ arrest signal in the cell.

A nucleotide sequence that can specifically bind to a RIZ can be detected by using methods well known in the art (see for example, El-Deiry et al., *Nat. Gen.* 1:45 (1992), which is incorporated herein by reference). Genomic DNA can be processed, for example, by sonication to produce uniform-sized fragments using, which can be screened for the ability to bind to a RIZ. Genomic DNA sequences that bind to a RIZ can be isolated using, for example, an anti-RIZ antibody and Protein A affinity chromatography. The isolated DNA sequences can be amplified by PCR, which can be facilitated by ligating the original genomic DNA fragments to "catch linkers" (El-Deiry et al., supra, 1992) suitable for annealing to PCR primers.

Random oligonucleotides consisting of at least about ten nucleotides and including "catch linkers" also can be screened to identify sequences that can bind a RIZ. For example, RIZ protein can be immobilized to a filter, then incubated with the oligonucleotides under conditions that allow the RIZ to bind relatively specifically to a RIZ binding sequence. Unbound oligonucleotides can be washed from the filter, then specifically bound sequences can be eluted and amplified by PCR. Following three or more cycles of binding, elution and amplification, a consensus RIZ binding sequence can be obtained. If desired, the consensus RIZ binding sequence can be used to screen a genomic DNA library to obtain genomic DNA sequences containing the RIZ binding sequence.

An agent can be a chemical or biological molecule such as a simple or complex organic molecule, a peptide, a peptido-mimetic, a protein, a carbohydrate or an oligonucleotide that has the potential for altering the association of a RIZ with a second molecule or altering an activity of a RIZ. With reference to a RIZ, the term "effective agent" means an agent that can, in fact, alter the association of RIZ with a second molecule or can alter the activity of a RIZ.

An effective agent can be, for example, a nucleic acid molecule that encodes a RIZ or a mutant RIZ or is complementary to a RIZ- or mutant RIZ-encoding nucleotide sequence. Such nucleic acid molecules can be contained within an expression vector having the RIZ encoding sequence operably linked to an expression control sequence. An effective agent also can be an antisense RIZ or a ribozyme complementary to a RIZ mRNA sequence. Such agents can reduce the level of expression of a RIZ in a cell and, as a consequence, can alter the amount of a RIZ that is associated with a second molecule in a cell.

As used herein with reference to a RIZ, the term "alter the association" means that the association of a RIZ and a second molecule either is increased or is decreased due to the presence of an effective agent. As a result of an altered association of RIZ with a second molecule in a cell, the activity of the RIZ or second molecule can be increased or decreased, which can modulate a function of a cell. As used herein with reference to a RIZ, the term "alter the activity" means that the effective agent can increase or decrease the activity of RIZ in a cell, such as by altering the association of a RIZ with the second molecule as described above by modifying, for example, an activity of a RIZ that occurs consequent to binding a second molecule.

An effective agent that alters the association of a RIZ with a second molecule can interfere with the ability of the RIZ and the second molecule to associate or can cause the dissociation of a bound RIZ-second molecule complex. In the presence of an effective agent, the association of a RIZ with a second molecule can be altered, which can alter the activity of the RIZ or the second molecule in the cell. As a result of the altered activity, a cell function such as the ability of a cell to proliferate can be modulated. Thus, the identification of an effective agent that alters the association of a RIZ with a second molecule provides a means to modulate cell proliferation.

An effective agent that alters the association of a RIZ and Rb can be useful as a medicament to treat a pathology characterized, in part, by excessive cell growth such as occurs in a cancer or by insufficient cell growth such as occurs in a tissue that fails to regenerate in response to cell death. A peptide having the sequence EIRCEEKPEDL (SEQ ID NO: 6) or EIRCDEKPEDL (SEQ ID NO: 91), which represent the cr2 motif of RIZ, is an example of an effective agent. Either of the peptides can alter the association between a RIZ and Rb (see Example II) and can induce cells such as adult cardiac muscle cells or adult neural cells to proliferate, which can regenerate heart function or neural function, respectively, following injury or disease.

The present invention also provides in vitro screening assays to detect an effective agent. Such screening assays are particularly useful in that they can be automated, which allows for high through-put screening, for example, of randomly or rationally designed agents such as drugs, peptido-mimetics or peptides in order to identify agents that effectively alter the association of a RIZ and a second molecule or modulate a function of a cell.

An in vitro screening assay can utilize, for example, RIZ or a RIZ fusion protein such as a glutathione-S-transferase-RIZ fusion protein (GST-RIZ; see Example II). For in vitro screening assays, the RIZ or RIZ fusion protein can be attached to a solid substrate, provided the attached RIZ maintains the ability to associate with a particular second molecule. For example, when human RIZ is used in the assay, the solid substrate can contain a covalently attached anti-RIZ antibody to bind RIZ to the substrate (see Example II). Alternatively, a GST-RIZ fusion protein can be used in the assay and the solid substrate can contain covalently attached glutathione, which is bound by the GST component of the GST-RIZ fusion protein. Similarly, a second molecule or a GST-second molecule fusion protein can be used in an in vitro assay as described herein.

An in vitro screening assay can be performed by allowing, for example, a RIZ or RIZ-fusion protein to bind to the solid support, then adding a second molecule and an agent to be tested. Alternatively, a second molecule or a second molecule-fusion protein can be attached to the solid support and RIZ and an agent to be tested are added. Control reactions, which do not contain an agent, can be performed in parallel. Following incubation under suitable conditions, which include, for example, an appropriate buffer concentration and pH and time and temperature of incubation that permit binding of a RIZ and a second molecule, the amount of the RIZ and second molecule that have associated in the absence of an agent and in the presence of an agent can be determined.

The association of a RIZ and a second molecule can be detected, for example, by attaching a detectable moiety such as a radionuclide or a fluorescent label to the second molecule and measuring the amount of label that is associated with the solid support, wherein the amount of label detected indicates the amount of association of the second molecule and RIZ. By comparing the amount of specific binding in the presence of an agent as compared to the control level of binding, an effective agent, which alters the association of a RIZ and a second molecule, can be identified. Such an assay is particularly useful for screening a panel of agents such as a peptide library in order to detect an effective agent.

In an in vitro screening assay as disclosed herein, the order in which the components are added can be informative. For example, the agent to be detected can be combined with a RIZ prior to adding a second molecule, can be combined with a second molecule prior to adding a RIZ or can be added after allowing binding of the RIZ and the second molecule. Depending on the relative affinities of the components in the reaction mixture for each other, the order of addition and the time between mixing the first two components and adding the remaining component can be manipulated to detect effective agents with varying properties.

The methods for identifying an effective agent that alters the association of RIZ with a second molecule, can be performed to determine, for example, whether the agent can dissociate a bound RIZ-second molecule complex. For this purpose, a RIZ is first contacted with a second molecule under conditions suitable for forming a RIZ-second molecule complex and thereafter the complex is contacted with the effective agent.

The invention also provides methods for identifying an effective agent that alters the association of a RIZ and a second molecule in a test sample containing the RIZ and the second molecule. As used herein, the term "test sample" means a cell or tissue specimen that is obtained from a subject and is to be examined for expression of RIZ protein or a nucleic acid molecule encoding RIZ. A test sample can be obtained, for example, during surgery or by needle biopsy. The test sample can be, for example, a soluble lysate of a cell preparation obtained by treating the cells with a solubilizing agent such as a non-ionic detergent.

A soluble lysate or other form of test sample can be examined by a gel-shift assay to determine the proportion of a RIZ and a second molecule that are associated as a complex. In this assay, the test sample is electrophoresed in a non-denaturing gel such as a low percentage polyacrylamide gel with a buffer containing 50 mM Tris (pH 8.5), 0.4M glycine, 2 mM EDTA and 3% glycerol. By adjusting the buffer conditions, gel concentration or other parameters of electrophoresis well known in the art, electrophoretic separation of a free second molecule, a free RIZ and a second molecule-RIZ complex in the test sample can be achieved. After electrophoresis, the identity of proteins in the gel can be determined by immunoblotting using antibodies specific for the second molecule or the RIZ. Methods for performing immunoblotting using an enzyme or radioisotope labeled primary or secondary antibody are well known in the art (see, for example, Harlow and lane, supra 1988).

If desired a separate gel can be produced and western blotted with either anti-second molecule antibodies or anti-RIZ antibodies. Each gel can contain known amounts of both the second molecule and the RIZ to be detected to provide standards for quantitation and specificity of the blot. The amount of a second molecule-RIZ complex in a test sample treated with an agent suspected of being able to alter the association of the second molecule with RIZ can be compared to a control test sample not treated with the agent in order to identify an effective agent, which increases or decreases the proportion of the second molecule-RIZ complex in the treated relative to the control test sample.

The present invention provides methods to modulate a function of a cell by contacting the cell with an effective agent. As used herein, the term "contacting" means providing within sufficient proximity such that the effective agent can interact with a target. Thus, an effective agent can be contacted with Rb in vitro, or can be contacted with a cell, provided the effective agent can enter the cell to interact with RIZ or a second molecule. For example, a small molecule effective agent can enter a cell passively such as through pores in the cell membrane or through the lipid bilayer of the cell. An effective agent also can enter a cell by active means such as through pinocytosis, endocytosis, phagocytosis or through an energy driven specific transport mechanism.

Methods for introducing and expressing a RIZ in a cell can be performed using well known expression vectors and gene transfer methods (for example, see Sambrook et al., supra, 1989 and Kriegler M. *Gene Transfer and Expression: A Laboratory Manual* (W. H. Freeman and Co. New York N.Y., 1990), which is incorporated herein by reference). Such gene transfer methods include, for example, transfection methods such as calcium phosphate precipitation, electroporation or lipofection, or viral infection. For convenience, the term "transfected cell" is meant to include any cell having an exogenous nucleic acid molecule introduced therein. Transfected cells useful for expressing large amounts of RIZ protein can be prokaryotic or eukaryotic and include, for example, bacterial cells such as *E. coli*, yeast cells, insect cells or mammalian cells such as COS cells or chinese hamster ovary (CHO) cells.

An expression vector useful for expressing a RIZ or a mutant RIZ in a cell contains an expression control sequence operatively linked to a nucleotide sequence encoding a RIZ. An expression control sequence that is operatively linked to a nucleic acid sequence can direct the transcription and translation of the nucleic acid sequence in vitro or in an appropriate host cell. Expression control elements are well known in the art and include, for example, promoters, enhancers and appropriate start and stop codons. In particular, a tissue specific expression control element can provide a means to selectively express a RIZ or mutant RIZ in a cell. Tissue specific control elements are well known in the art and include, for example, the muscle creatine kinase enhancer for restricting expression to muscle cells and the Purkinje cell protein-2 promoter for restricting expression to Purkinje cells (Vandaele et al., *Genes Devel.* 5:1136–1148 (1991), which is incorporated herein by reference).

Viral vectors that are compatible with a targeted cell are particularly useful for introducing a nucleic acid molecule encoding a RIZ or a mutant RIZ into a cell. For example, recombinant adenoviruses having general or tissue-specific promoters can be used to deliver a nucleic acid encoding RIZ into a variety of cell types in various tissues and can direct expression of the nucleic acid in the target cell (Lebkowski et al. U.S Pat. No. 5,354,678, issued Oct. 11, 1994, which is incorporated herein by reference). Recombinant adeno-associated viruses also are useful for introducing a nucleic acid molecule encoding RIZ into a cell and have the added advantage that the recombinant virus can stably integrate into the chromatin of even quiescent non-proliferating cells such as neurons of the central and peripheral nervous systems (Lebkowski et al., *Mol. Cell. Biol.* 8:3988–3996 (1988), which is incorporated herein by reference).

Such viral vectors are particularly useful where it is desirable to introduce a nucleic acid molecule encoding a RIZ or a mutant RIZ into a cell in a subject, for example, for gene therapy. Viruses are specialized infectious agents that can elude host defense mechanisms and can infect and propagate in specific cell types. The specificity of viral vectors for particular cell types can be utilized to target predetermined cell types. Thus, the selection of a viral vector will depend, in part, on the cell type to be targeted. For example, if a neurodegenerative disease is to be treated by increasing the level of RIZ in neuronal cells affected by the disease, then a viral vector that targets neuronal cells can be used. A vector derived from a herpes simplex virus is an example of a viral vector that targets neuronal cells (Battleman et al., *J. Neurosci.* 13:941–951 (1993), which is incorporated herein by reference).

A viral vector that is specific for a particular blood cell or its precursor cell can be used to introduce a nucleic acid molecule encoding a RIZ or a mutant RIZ into a hematopoietic cell from a subject having a pathological condition of the hematopoietic system. A vector based on a human immunodeficiency virus is an example of such a viral vector (Carroll et al., *J. Cell. Biochem.* 17E:241 (1993), which is incorporated herein by reference). In addition, a viral vector or other vector can be constructed to express a nucleic acid encoding a RIZ in a tissue specific manner by incorporating a tissue-specific promoter or enhancer into the vector (Dai et al., *Proc. Natl. Acad. Sci. USA* 89:10892–10895 (1992), which is incorporated herein by reference).

Retroviral vectors can be particularly useful for introducing a nucleic acid molecule encoding a RIZ or a mutant RIZ into a cell in vivo. Retroviral vectors can be constructed either to function as infectious particles or as non-infectious particles that undergo only a single initial round of infection. In the former case, the genome of the virus is modified so that it maintains the necessary genes, regulatory sequences and packaging signals to synthesize new viral proteins and RNA. However, genes conferring oncogenic potential of these viruses are destroyed or removed. After the viral proteins are synthesized, the host cell packages the RNA into new viral particles, which can undergo further rounds of infection. The viral genome also is engineered to encode and express the desired recombinant gene.

In the case of non-infectious viral vectors, a helper virus genome is required to provide the structural genes necessary to encode for the viral structural proteins. However, the helper virus is mutated to destroy the viral packaging signal required to encapsulate the helper viral RNA into viral particles. Thus, only the recombinant viral vector containing the gene of interest and a functional packaging signal, but lacking viral structural genes can be incorporated into a virus particle. Although this new virus can infect a target cell, no further infectious virus can be produced since there are not viral structural genes provided. Methods for constructing and using viral vectors are known in the art and reviewed, for example, in Miller and Rosman, *Biotechniques* 7:980–990 (1992), which is incorporated herein by reference. The specific type of vector will depend upon the intended application. These vectors are well known and readily available within the art or can be constructed by one skilled in the art.

For gene therapy, a vector containing a nucleic acid encoding a RIZ or a mutant RIZ can be administered to a subject by various methods. For example, if viral vectors are used, administration can take advantage of the target specificity of the vectors. In such cases, there is no need to administer the vector locally at the diseased site. However, local administration can be a particularly effective method of administering a nucleic acid molecule. In addition, administration can be via intravenous or subcutaneous injection into the subject. Following injection, the viral vectors will circulate until they recognize host cells with the appropriate target specificity for infection. Injection of viral vectors into the spinal fluid also can be an effective mode of administration, for example, in treating a neurodegenerative disease.

Receptor-mediated DNA delivery approaches also can be used to deliver a nucleic acid molecule encoding a RIZ or a mutant RIZ into a cell in a tissue-specific manner using a tissue-specific ligand or an antibody that is non-covalently complexed with the nucleic acid molecule via a bridging molecule (Curiel et al., *Hum. Gene Ther.* 3:147–154 (1992); Wu and Wu, *J. Biol. Chem.* 262:4429–4432 (1987), each of which is incorporated herein by reference). Direct injection of a naked or a nucleic acid molecule encapsulated, for example, in cationic liposomes also can be used for stable gene transfer into non-dividing or dividing cells in vivo (Ulmer et al., *Science* 259:1745–1748 (1993), which is incorporated herein by reference). In addition, a nucleic acid molecule encoding a RIZ can be transferred into a variety of tissues using the particle bombardment method (Williams et al., *Proc. Natl. Acad. Sci. USA* 88:2726–2730 (1991), which is incorporated herein by reference). Such nucleic acid molecules can be linked to the appropriate nucleotide sequences required for transcription and translation.

A particularly useful mode of administration of a nucleic acid encoding a RIZ or mutant RIZ is by direct inoculation locally at the site of the disease or pathological condition. Local administration can be advantageous because there is no dilution effect and, therefore, the likelihood that a majority of the targeted cells will be contacted with the nucleic acid molecule is increased. Thus, local inoculation can alleviate the targeting requirement necessary with other forms of administration and, if desired, a vector that infects all cell types in the inoculated area can be used. If expression is desired in only a specific subset of cells within the inoculated area, then a promotor, an enhancer or other expression element specific for the desired subset of cells to be targeted can be linked to the nucleic acid molecule. Vectors containing such nucleic acid molecules and regulatory elements can be viral vectors, viral genomes, plasmids, phagemids and the like. Transfection vehicles such as liposomes also can be used to introduce a non-viral vector into recipient cells. Such vehicles are well known in the art.

An alternative method of modulating a function of a cell is to introduce a nucleic acid molecule having a nucleotide sequence encoding an antisense RIZ or a ribozyme specific for a RIZ mRNA into the cell. Such a nucleotide sequence is included within the meaning of an effective agent since it can alter the expression level of RIZ and thus alter the association of a RIZ with a second molecule.

An antisense RIZ or a ribozyme specific for a RIZ mRNA can be complementary to the nucleotide sequence of a RIZ such as the nucleotide sequence of FIG. 1 (SEQ ID NO: 1) or FIG. 9 (SEQ ID NO: 3). An antisense RIZ or ribozyme specific for RIZ mRNA can be introduced into a cell using the methods and vectors described above. Chemically synthesized nucleotide sequences also can be administered directly to cells. Synthetic antisense or ribozyme oligonucleotides can be prepared using well known methods or can be purchased from commercial sources and, if desired, can incorporate nucleotide analogs to increase the resistance of the oligonucleotide to degradation by nucleases in a cell. Synthetic antisense or ribozyme sequences can be active in a cell after contact with and uptake by the cell.

An effective agent can be administered in vivo as a pharmaceutical composition containing the effective agent and a pharmaceutically acceptable carrier. Pharmaceutically acceptable carriers are well known in the art and include, for example, aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of an effective agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. One skilled in the art would know that a pharmaceutical composition containing an effective agent can be administered to a subject by various routes including, for example, by direct instillation, orally or parenterally, such as intravenously, intramuscularly, subcutaneously or intraperitoneally. The composition can be administered by injection or by intubation. The pharmaceutical composition also can be incorporated, if desired, into liposomes or microspheres or can be microencapsulated in other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

In order to modulate a function of a cell, an effective agent is administered in an effective amount, which can be determined using methods well known to those in the art. As used herein, the term "effective amount" means the amount that produces a desired effect. Thus, an effective amount of an effective agent can alter the association of a RIZ and Rb in a cell and can have a functional effect on the ability of a target cell to increase or decrease its ability to enter the cell cycle. Administration of an effective amount of an effective agent in vivo can reduce symptoms associated with a disease being treated.

The total effective amount can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of an effective agent needed to obtain an effective amount in a subject depends on many factors including the age and general health of the subject as well as the route of administration and the number of treatments to be administered, as well as the chemical form of the effective agent. In view of these factors, the skilled artisan would adjust the particular dose so as to obtain an effective amount for subject being treated.

The present invention also provides methods for detecting the presence of a RIZ in a test sample by detecting the RIZ protein or a nucleic acid molecule encoding RIZ. In addition, methods are disclosed for diagnosing a pathology that is characterized, in part, by an increased or decreased ability of a cell to enter the cell cycle by determining whether cell proliferation or lack thereof is due, for example, to increased or decreased expression of a RIZ or a mutant RIZ in the cell. The identification of such a pathology can allow for intervention therapy using an effective agent as described above.

A test sample can be obtained from a subject having a pathology characterized by increased or decreased cell function and can be compared to a control sample from a normal healthy subject to determine whether the cells in the test sample have an increased or decreased level of a RIZ or a mutant RIZ. The level of RIZ protein in a cell can be determined by contacting a sample with a RIZ binding reagent such as an anti-RIZ antibody or Rb. For example, the level of RIZ in a cell can be determined by well known immunoassay or immunohistochemical methods using an anti-RIZ antibody (see, for example, Reed et al., supra, 1992; see, also, Harlow and Lane, supra, 1988). In addition, the expression of a mutant RIZ can be detected, for example, by an antibody that specifically binds to the mutant RIZ but not to wild-type RIZ.

The detection of a RIZ by binding to an antibody and to Rb can provide complementary information. For example, the antibody can be used to determine the total level of RIZ expressed, while Rb binding can be used to determine the fraction of RIZ that is bound to Rb. Because Rb can bind to other proteins in a cell, it is advantageous to first isolate RIZ from a cell prior to detecting the fraction of RIZ that is bound to Rb.

An increased or decreased level of expression of a RIZ in a cell in a test sample can be determined by comparison to an expected normal level for the RIZ in a particular cell type. A normal range of RIZ levels in various cell types can be determined by sampling a statistically significant number of normal cell types, which can be obtained from healthy subjects. In addition, a control sample can be evaluated in parallel with a test sample in order to determine whether a pathology characterized by increased or decreased cell function is due to increased or decreased expression of a RIZ or to expression of a mutant RIZ. The test sample can be examined using, for example, immunohistochemical methods as described above or the sample can be further processed and examined. For example, an extract of a test sample can be prepared and examined to determine whether RIZ that is expressed in cells in the sample can associate with Rb in the same manner as RIZ from control cells or whether a variant RIZ, which does not properly associate with Rb, is expressed in the cells in the test sample.

A diagnostic assay kit incorporating a reagent such as an anti-RIZ antibody or Rb can be useful for detecting a pathology due to altered RIZ expression or to expression of a mutant RIZ in a cell. Such a kit is particularly useful because it allows for standardization of assay conditions. A kit can contain, in addition to a reagent, a reaction cocktail that provides suitable reaction conditions for performing the assay and, if desired, a control sample that contains a known amount of RIZ. In addition, the kit can contain an antibody that is specific for the reagent. Where Rb is used as a reagent to detect RIZ, the kit also can contain a competitor molecule such as EIRCEEKPEDL (SEQ ID NO: 6) or EIRCDEKPEDL (SEQ ID NO: 91), which inhibits the association of RIZ and Rb and, therefore, can confirm the specificity of the binding reaction.

A diagnostic assay should include a simple method for detecting the amount of RIZ in a sample that is bound to the reagent. Detection can be performed by labeling the reagent and detecting the presence of the label using well known methods (see, for example, Harlow and Lane, supra, 1988; chap. 9, for labeling an antibody). A reagent can be labeled with various detectable moieties including a radiolabel, an enzyme, biotin or a fluorochrome. Materials for labeling the reagent can be included in the diagnostic kit or can be purchased separately from a commercial source. Following contact of a test sample and, if desired, a control sample, with a labeled reagent, specifically bound reagent can be identified by detecting the particular moiety.

A labeled antibody that can specifically bind the reagent also can be used to identify specific binding of an unlabeled reagent. For example, if the reagent is an anti-RIZ antibody, a second antibody can be used to detect specific binding of the anti-RIZ antibody. A second antibody generally will be specific for the particular class of the first antibody. For example, if an anti-RIZ antibody is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody, then the sample is contacted with the labeled second antibody, which specifically binds to the first antibody and results in a labeled sample.

A method for diagnosing a pathology characterized by an abnormal level of expression of a RIZ or can involve measuring the level of expression of a DNA or RNA in the sample. Similarly, diagnosing a pathology characterized by expression of a mutant RIZ or by the presence of a mutant nucleic acid molecule encoding a RIZ can involve detecting the mutation in the RIZ gene or in the RNA encoded by the gene.

For example, a nucleic acid molecule encoding a RIZ can be detected in a test sample using a complementary nucleotide sequence. If desired, the target nucleic acid molecule can be extracted from a test sample by methods well known in the art (See Sambrook et al., supra, 1988). Methods to detect the presence of a particular nucleic acid molecule within a population of nucleic acid molecules are well known to those in the art and include, for example, Southern blotting, northern blotting, slot blotting and PCR amplification (see, for example, Sambrook et al., supra, 1989). In situ hybridization also can be used to identify nucleic acids in directly in a sample containing cells or free chromosomes (see for example, Pardue, in *Nucleic Acid Hybridisation: a practical approach* (IRL Press, 1991), which is incorporated herein by reference).

To detect a nucleic acid molecule encoding a RIZ in a sample, the sample is contacted with the complementary nucleotide sequence, which can hybridize to a nucleic acid molecule encoding the RIZ under relatively stringent conditions. The nucleotide sequence can carry a detectable label such as a radioisotope. The presence of a nucleic acid molecule encoding the RIZ in the sample can be determined, for example, by detecting the level of the specifically bound nucleotide sequence. The normal level of binding of the nucleotide sequence also can be determined in a control sample. An increase or a decrease in the level of nucleic acid molecules encoding a RIZ in the test sample compared to the control sample indicates a pathology characterized by an abnormal expression of the RIZ. A complementary nucleotide sequence for a RIZ can also be used as a primer in a PCR reaction to amplify the RIZ for hybridization by a probe.

A mutant RIZ can be detected by hybridizing with a complementary nucleic acid molecule under relatively stringent conditions essentially as described above except that the complementary sequence is of sufficiently small size to enable selective hybridization to the mutant sequence but not to the wild-type sequence under the conditions chosen for hybridization. Alternatively, the RIZ gene or RNA can be purified directly from a test sample and, if desired, amplified from the sample by PCR and the mutant sequence determined by standard nucleotide sequencing methods (see, for example, Sambrook et al. supra, 1989). The mutant nucleic acid encoding a RIZ or the nucleic acid encoding a mutant RIZ also can be detected in a sample of cells or free chromosomes by in situ hybridization techniques (see, for example Pardue, supra, 1991).

The following Examples are intended to illustrate but not limit the invention.

EXAMPLE I

Cloning of Mammalian RIZ cDNAs

This section describes methods to clone a nucleic acid molecule encoding a RIZ from mammalian cDNA and genomic libraries.

The rat RIZ cDNA was obtained from a rat neonatal cardiac myocyte λgt11 cDNA expression library (Zhu et al., *Mol. Cell Biol.*, 13:4432 (1993), which is incorporated herein by reference). The library was screened using a 56 kD fragment containing the pocket binding site of Rb and the EE epitope (p56EERb) according to previously described methods (Macgregor et al., *Oncogene*, 5:451–458 (1991), which is incorporated herein by reference).

After induction of p56EERb was generated by cloning a synthetic pair of complementary polynucleotides that hybridize to form a double stranded linker encoding the EE-epitope, EEEEYMPME (SEQ ID NO: 8; Grussenmeyer et al., *Proc. Natl. Acad. Sci., USA.*, 82:7952–7954 (1985) and Walter, *J. Immune Meth.*, 88:149–161 (1986), both of which are incorporated herein by reference) and having Bsm I cohesive ends. The ends of the linker were phosphorylated by T4 kinase and the linker was ligated into the plasmid pET8Rbc (Huang et al., *Nature*, 350:160–162 (1991), which is incorporated herein by reference) to produce the plasmid p56EERb. The synthetic nucleotides used to make the linker were: 5'-AATCGATGAA GAAGAAGAAT ATATGCCTAT GGAACA-3' (SEQ ID NO: 9), and 5'-TTCCATAGGC ATATATTCTT CTTCTTCATC GATTTG-3' (SEQ ID NO: 10). A clone with four tandem copies of the EE linker was selected and used to direct expression of p56EERb in the *E. coli* strain BL21(DE3)pLysS as previously described (Huang et al. supra, 1991).

After induction of 56EERb, the bacterial cells were lysed as described (Huang et al. supra, 1991) and 56EERb was precipitated by ammonium sulfate (60% of saturation). The precipitate was dialyzed in dialysis buffer (20 mM Tris-HCl, pH 7.5, 50 mM NaCl, 1 mM EDTA, 1 mM DTT, 1 mM PMSF) and subjected to further purification by diethylaminoethyl (DEAE) Sepharose™ chromatography (Pharmacia, Piscataway, N.J.). Partially purified p56EERb was eluted from DEAE by a salt gradient of 50 mM to 500 mM NaCl. Both the DEAE partially purified fraction and the dialyzed ammonium sulfate precipitate of 56EERb were used for screening the cDNA library.

For binding-specificity control, p56EERb was preincubated with 5 μM poly-L-lysine (Sigma) or 50 μM T- or K-peptide (Huang et al., supra, 1991) before applying onto filters. T peptide is an 18 residue synthetic peptide derived from residues 101–118 of SV40 large T antigen, while K peptide is the same as T peptide except for a lysine residue substituted for a glutamic acid residue at position 107 of SV40 large T antigen (Huang et al., supra, 1991). The T peptide binds to the Rb pocket while the K peptide does not.

The binding of p56EERb to a clone expressing a RIZ protein was detected using an anti-EE monoclonal antibody obtained as spent culture medium of the anti-EE hybridoma (Walter, supra, 1986) and an alkaline phosphatase conjugated goat anti-mouse IgG antibody specific for mouse immunoglobulin (Promega, Madison, Wis.).

Filters containing $1 \times 10^6$ library phage plaques were screened using p56EERb and ten positive clones that survived three rounds of plaque purification were selected. Five clones, which maintained their reactivity with p56EERb in the presence of a non-specific inhibitory substance, poly-L-Lysine, but were inhibited from binding p56EERb in the presence of T peptide but not K peptide, were selected for further study. Inhibition by T peptide indicated that the selected clones expressed a product that binds the Rb pocket.

Of the final five clones, four contained an identical 1.9 kilobase (kb) insert. One of the clones, clone 7.1, was subjected to nucleotide sequencing. Sequencing was performed on both strands of the DNA and utilized the Sequenase enzyme™ (United States Biochemical Corp., Arlington Hts., Ill.). Clone 7.1 contained a partial cDNA sequence having a predicted open reading frame encoding 638 amino acids, which formed two types of readily recognizable motifs: a cr2 core motif and 3 zinc finger motifs (see below). The protein encoded by clone 7.1 was designated RIZ for "Rb-interacting zinc finger" protein.

The 1.9 kb insert was used to further screen the cardiac myocyte library and to screen a rat brain B49 cell cDNA library produced in the λZAP vector (Stratagene) according to standard methods (see Sambrook et al., supra, 1989) or purchased from a commercial source. Several clones containing overlapping open reading frames were obtained. The overlapping sequences were assembled into a contiguous stretch of 6171 nucleotides to obtain the cDNA sequence for rat RIZ (FIG. 1; SEQ ID NO: 1).

Analysis of the complete rat RIZ cDNA sequence revealed a large open reading frame beginning at nucleotide 157 and ending at nucleotide 5274. The initiation codon at nucleotide 157 was considered the translational start site based on its being the first ATG following an in-frame upstream stop codon at nucleotide 100 and by it's match with the Kozak consensus sequence (Kozak, Nucl. Acids Res. 15: 8125–8148 (1987)). The identity of the start site was confirmed by analyzing an independent cDNA clone that revealed a divergent sequence upstream of nucleotide 92 but otherwise was identical to the assembled cDNA sequence of rat RIZ.

The complete rat RIZ cDNA sequence predicted a protein consisting of 1706 amino acids having a molecular weight of 187,437 Daltons (FIG. 1). Northern blot analysis showed a 7.2 kb major rat RIZ mRNA species. Southern blot analysis indicated that the rat RIZ genome contains a single copy of the RIZ gene.

A nucleic acid molecule encoding human RIZ was cloned from a human fetal brain cDNA library (Clonetech, Palo Alto CA) and a human placental genomic cosmid DNA library (Stratagene, San Diego CA) using the rat RIZ cDNA coding regions as a hybridization probe (clone 7.1). The human RIZ cDNA encodes a polypeptide of 1719 amino acids residues (see FIG. 9; SEQ ID NO: 4). The human RIZ gene obtained from the genomic library showed that RIZ coding sequence was divided between eight separate exons.

An allelic variant of the human RIZ gene is also identified. This variant contains a single nucleotide change of $T_{849}$ to $A_{849}$, leading to a change of amino acid residue $D_{283}$ to $E_{283}$. The $T_{849}$ allele is estimated to be two times more frequent than the $A_{849}$ allele.

Both the rat and human RIZ proteins have similar sequence motifs including cr1, cr2, ce1, zinc finger, SH3, SH2 and a nuclear localization signal. The deduced rat and human RIZ amino acid sequences show 83% identity. In addition, a rabbit antiserum prepared to rat RIZ crossreacts with human RIZ.

EXAMPLE II

Detection and Characterization of RIZ-Rb Binding

This section describes methods for demonstrating binding of RIZ and Rb and for identifying an agent that effectively alters the binding of a RIZ and Rb.

To characterize the interaction between RIZ and Rb, a $^{35}$S-labeled fragment of rat RIZ from amino acid position 245-883 (RIZ (245-883)) was produced by subcloning the 1.9 kb insert of clone 7.1 into pBKS+ (Stratagene) to yield plasmid pBKS+7.1. Following subcloning, the RIZ insert was then removed and inserted downstream of the 5' untranslated sequence of β-globin in the vector pSP64-xβm (Krieg and Melton, Nucl. Acids Res., 12:7057–7070 (1984). SP6 RNA transcripts encoding RIZ (245–883) were produced by linearizing the plasmid encoding this fragment with Sal I and translating the RIZ fragment using a rabbit reticulocyte lysate in vitro protein translation system (Promega) containing $^{35}$S-methionine. The labeled RIZ fragment had an apparent molecular weight of 125 kD by sodium dodecyl sulfate polyacrylamide gel electrophoresis (SDS-PAGE), which was about 55 kD greater than the predicted molecular mass for this fragment of RIZ. The larger size obtained by SDS-PAGE is likely due to anomalous mobility of the RIZ fragment on the gel.

A 56 kD fragment of Rb produced by bacterial expression from p55Rb plasmid, as described previously (Huang et al., supra, 1991), was tested for binding to radiolabeled RIZ (245–883). Binding was detected by immunoprecipitation with an anti-Rb antiserum and Protein A-Sepharose™ (Huang et al., supra, 1990), which is incorporated herein by reference; and Huang et al., supra, 1991) followed by SDS-PAGE and autoradiography (see Harlow and Lane, supra, 1988). The rabbit anti-Rb antiserum was produced to purified p56Rb using previously described methods (see Harlow and Lane, supra, 1988).

The amount of binding of RIZ by Rb in the immunoprecipitation reaction was dependent on the concentration of Rb added. Full binding of $^{35}$S-labeled RIZ (245–883) was achieved by 10 nM Rb but not 3.3 nM Rb (not shown). These results indicated that RIZ binds Rb.

A competition experiment was used to compare the relative binding affinity of RIZ for Rb as compared to another Rb binding protein, SV40 large T antigen. The full length large T antigen cDNA was subcloned from Y-62–25–2 into plasmid pSP64 for in vitro transcription/translation and $^{35}$S-methionine labeling as described above. When approximately equal amounts of T antigen and RIZ were mixed individually or together with the same amount of Rb, similar amounts of T antigen and RIZ, or somewhat more RIZ, were co-precipitated (not shown). These data indicate that RIZ has a similar binding affinity for Rb as does large T antigen.

Several mutations were generated to identify the regions of RIZ that were involved in binding to Rb. A single amino acid substitution was introduced into full length RIZ cDNA in the plasmid pCMVRIZ to change cysteine at a.a. position 307 to glycine. PCMVRIZ was produced by subcloning the full-length RIZ cDNA into the pRc-CMV vector (Invitrogen, San Diego, Calif.). Mutagenesis of the cr2 motif changing Cys to Gly was performed using the T7 GENE™ mutagenesis kit (United States Biochemical, Arlington Heights, Ill.) as follows: Briefly, the primer, 5'-CCGGAGATCC GGGCTGAAGA AAAGCCA -3' (SEQ ID NO: 11), was used to direct DNA synthesis on a single stranded antisense template prepared from pBSK-5.4. Vector pBSK-5.4 was produced by cloning the cDNA RIZ amino terminal clone 5.4 obtained from the B49 λZAP DNA library into vector pBSK+. An Nsi I to Spe I fragment (nucleotide 1-1718) containing the point mutation was sequenced and subcloned into pRc-CMV to produce pCMVmRIZ (RIZ$^{307\text{-}Gly}$). A $^{35}$S labeled fragment of RIZ from amino acid position 1-575 (RIZ (1-575)) and $^{35}$S-RIZ (1-575)$^{307\text{-}Gly}$ were produced by in vitro transcription/translation of Spe I linearized template as described above.

Binding between labeled RIZ (1-575) and the glycine mutant with 33 nM Rb was evaluated by immunoprecipitation with anti-Rb antiserum followed by SDS-PAGE and autoradiography. The results showed that the 56 kD Rb bound the $^{35}$S-RIZ (1-575) fragment but not to the $^{35}$S-RIZ (1-575)$^{307-Gly}$ cr2 mutant (not shown). These results indicate that the RIZ cr2 motif is involved in Rb binding.

To determine whether the RIZ cr2 motif is functional and sufficient for binding Rb, the 11 amino acid peptide EIRCEEKPEDL (SEQ ID NO: 6), representing the cr2 motif of RIZ (RIZ-Pep), and a cysteine to glycine mutant of this peptide (RIZ-Pep*) were synthesized according to standard procedures and tested at various concentrations for their ability to inhibit the binding of labeled RIZ (1-575) to 56 kD Rb. Binding was inhibited with wild-type peptide but not the C→G mutant peptide (see FIG. 4). These data indicate the cr2 motif of RIZ is sufficient for binding to Rb and that the cysteine at a.a. position 307 in the cr2 motif of RIZ is involved in the binding.

In a similar manner, the binding between radiolabeled RIZ (1-575) and 56 kD Rb was tested for inhibition using the 17 amino acid Rb binding peptide (101-118: T-pep) from the SV40 large T antigen oncoprotein and a position 107 Glu to Lys mutant of T-pep (T-pep*) that lacks Rb binding activity (Huang et al., supra, 1990 and Huang et al., supra, 1991). Binding was inhibited with T-pep but not with the mutant (FIG. 4). These results indicate that RIZ and large T antigen bind to a similar region on Rb.

The 56 kD Rb fragment that binds to RIZ is a C-terminal fragment containing the Rb pocket binding region and a C-terminal extension. To further define the portion of 56 kD Rb that binds to RIZ, several Rb mutant polypeptides were tested for binding to RIZ. Mutant and full length Rb were cloned and in vitro transcribed/translated as described previously (Huang et al., supra, 1990). H209 is a point mutation resulting in a single amino acid change in Rb that was identified in the small cell lung cancer H209 cell line (American Type Culture Collection (ATCC) #HTB 172). The various Rb forms were tested for binding to glutathionine S-transferase (GST) fused to a fragment of RIZ from amino acid position 245-573 (GST-RIZ (245-573)). This RIZ fragment contains all of the E1A motifs related to binding Rb and was constructed by cloning a Stu I-Hpa I RIZ fragment (nucleotide 795-3068) into vector pBSK+ to make pBSK+SH. An Eco RI fragment was removed from pBSK+SH and ligated into pGEX-KG to produce vector pKG7.1S containing GST-RIZ (245-573).

The binding between purified GST-RIZ (245-573) and the above radiolabeled Rb wild-type and deletion mutants were determined by immunoprecipitation with an anti-RIZ antiserum followed by SDS-PAGE and autoradiography. The antiserum was generated by injecting rabbits with the purified GST fused to a fragment of RIZ from amino acid position 245-573 (RIZ (245-573)), which contains zinc fingers 1-3, according to commonly used procedures (see Harlow and Lane, supra, 1988). GST-RIZ (245-573) used for immunizing rabbits was produced by expression of plasmid pKG7.1S in E. coli strain XL-1 blue. The bacteria were lysed and the GST-RIZ fusion protein isolated by glutathionine agarose column chromotography. pKG7.1S was constructed by ligating the 1.9 kb RIZ insert from pB7.1 into vector pGEX-KG. The resulting plasmid was linearized with Spe I, treated with Klenow fragment of DNA polymerase I and religated, thereby introducing a stop codon at the former Spe I site (nucleotide 1876).

The anti-RIZ antiserum specifically bound to in vitro translated RIZ (245-883) expressed from pB7.1. This binding was inhibited by the addition of the immunogen, GST-RIZ (245-573).

Purified GST-RIZ (245-573) showed binding to wild-type Rb and the B3 mutant of Rb, which contains a deletion C-terminal to the Rb binding pocket, but failed to bind three different forms of Rb having a deletion within the pocket (FIG. 5A). These results indicate that the Rb pocket, which was initially defined for its role in binding of oncoproteins such as the large T antigen or E1A, also is required for binding to RIZ. RIZ-binding by Rb does not require the C-terminal sequence distal to the pocket, as do certain cellular proteins such as E2F (see Huang et al., DNA Cell Biol., 11:539–548 (1992); Qin et al., Genes Devel., 6:953–964 (1992)) and c-Abl oncoprotein (see Welch and Wang, Cell 75:779–790, (1993)). The binding results map the C-terminal boundary of the RIZ-binding domain of Rb to residue 803 of Rb, in close proximity to the beginning of the N-terminal boundary of the Rb pocket (FIG. 5B).

Rat RIZ was tested for binding to Rb in HT1080 cells (ATCC #ICCL 121). The cells were grown in DMEM supplemented with 10% fetal calf serum. Cells were lysed in ELB buffer (50 mM HEPES, pH 7.5, 250 mM NaCl, 0.1% NP-40) supplemented with 5 mM EDTA, 50 mM NaF, 1 mM Na orthovandate, 1 mM of DTT, aprotinin, leupeptin, and PMSF. The lysate was cleared of cell debris by centrifugation at 12,000 rpm for 10 min in a microfuge.

Binding between 4 μg GST-RIZ (215-462) and Rb from HT1080 cell extract was evaluated by first mixing the two, then binding GST-RIZ and any associated Rb to glutathione-agarose beads. The beads were washed in binding buffer and the bound complexes were eluted by boiling in SDS buffer and analyzed by immunoblotting with anti-Rb antiserum. Immunoblotting was performed by standard techniques (see, for example, Harlow and Lane, supra, 1988).

Figure 6:
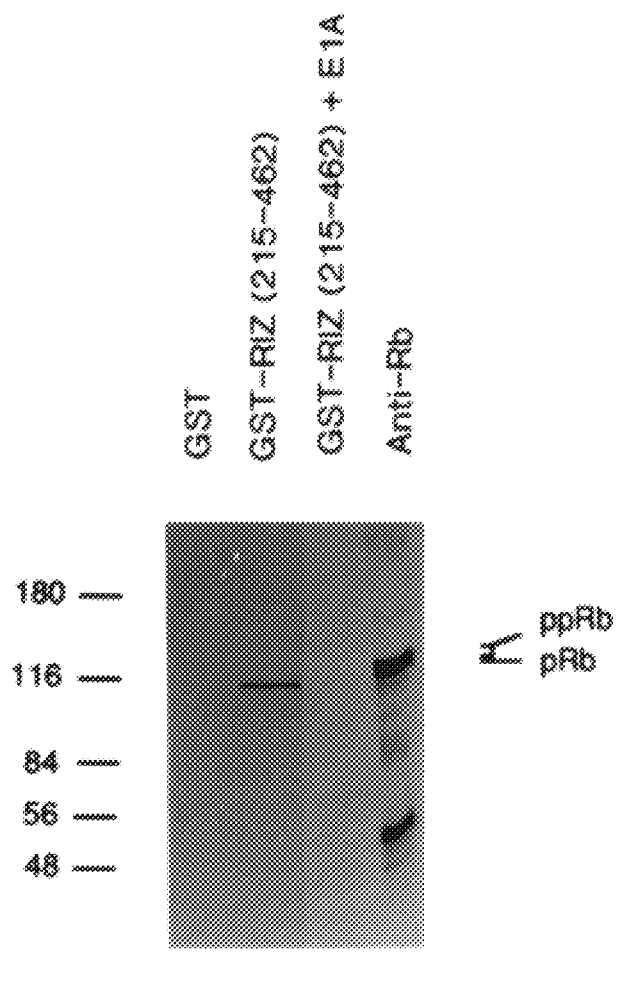
FIG. 6 shows in vitro binding of Rb from HT1080 cells with purified rat RIZ (a.a. position 215-462) fused C-terminal to glutathionine S-transferase (GST). The positions of hypophosphorylated Rb (pRb) and phosphorylated Rb (ppRb) from HT1080 cell extract are indicated in lane 4. Numbers to left indicate the migration of molecular weight markers (kilodaltons).

GST-RIZ (215-462) bound to the fastest migrating forms of Rb, representing hypophosphorylated Rb (FIG. 6, lane 2). The specificity of the interaction between RIZ and hypophosphorylated Rb was demonstrated by showing that the addition of a source of E1A protein inhibited binding (FIG. 6, lane 3). A cell lysate from 293 stably transfected to express E1A was used as the source of E1A.

EXAMPLE III

Structural and Functional Comparison Between RIZ and E1A

The similarity in sequence of particular domains between RIZ and Adenovirus E1A (see FIG. 2A) and the shared property of Rb binding indicated significant structural similarity between RIZ and E1A. To investigate this relationship further, the anti-RIZ antiserum raised against the GST-RIZ (245-573) fusion protein containing the cr2, ce1 and part of the cr1 motifs, was tested for crossreactivity with E1A. For these experiments, E1A was labeled with $^{35}$S-methionine during in vitro transcription/translation using methods described above.

Anti-RIZ antiserum crossreacted weakly with E1A (not shown). To further verify binding between anti-RIZ and E1A, the crossreactive antibodies from the anti-RIZ antiserum were purified by affinity chromatography on a column containing E1A 12S protein. The column was prepared by coupling Affi-gel 10™ beads (Bio-Rad Laboratories, Hercules Calif.) with the purified GST-E1A 12S fusion protein expressed from pGSTE1A12S (Taylor et al., Mol. Cell. Biol. 13:4714–4727 (1993), which is incorporated herein by reference). Antibody affinity purification was conducted by high pH elution according to standard procedures (see Harlow and Lane, supra, 1988).

Anti-RIZ antibodies purified from the E1A affinity column were tested for binding to RIZ and E1A. Both proteins were bound by the antibodies, confirming the original cross-reactivity of the anti-RIZ antiserum with E1A 12S (not shown). The E1A-affinity purified RIZ antibodies were designated "anti-ce1" for crossreacting E1A antigen.

Anti-ce1 antibodies were tested for binding to various deletion mutants of RIZ and E1A 12S in order to map the location of the ce1 epitope on each molecule. A RIZ mutant truncated after residue 304 (RIZ304) was produced by in vitro transcription/translation of a BAM HI digested fragment derived from a BAM H1 mutant of pCMVRIZ. A T7 GEN™ mutagenesis kit (U.S. Biochemical) was used to introduce a Bam HI restriction site into pCMVRIZ at RIZ nucleotide 1067 using the primer 5'-TTCACACCGG ATC-CCCGGCT CTTTCGC -3' (SEQ ID NO: 12). The Bam HI fragment was then excised and cloned into pRc-CMV to yield a vector encoding RIZ304.

A RIZ mutant truncated after residue 308 (RIZ308) was produced by PCR using full-length RIZ as the template and an upstream T7 primer (Stratagene) and a downstream RIZ primer 5'- TGGCTCTTCT AATAAGTC -3' (SEQ ID NO: 13). The PCR fragment was cloned into pCRSK+ (Stratagene) and used to produce the RIZ318 polypeptide by in vitro T7 transcription/translation.

E1A 12S, truncated at residue 223 (E1A223) was produced by generating a PCR fragment of E1A using an upstream SP6 primer (Stratagene) a downstream E1A primer 5'- GATACATTCC ACAGCCTG -3' (SEQ ID NO: 19) and the plasmid pGEM1Ad5E1A12S as template. The resulting PCR fragment was cloned into pCRSK+, which was used to direct the synthesis of the mutant E1A 12S protein by SP6 in vitro transcription/translation. The full length E1A 12S (E1A243) was produced from vector pGEM1Ad5E1A12S by in vitro transcription/translation as described above for the other vectors.

Anti-ce1 antibody bound to RIZ truncated at residue 318 but failed to react with RIZ truncated at residue 304 (not shown). These results indicate that the ce1 crossreactive antigenic determinant lies within residues 304 to 318 of RIZ. Anti-ce1 antibody bound to full length E1A (EIA243) but failed to react with the C-terminal deletion mutant of E1A (E1A223; not shown). These results indicate that the ce1 epitope is located within the C-terminal 20 amino acids of E1A 12S.

The regions of RIZ and E1A 12S that contain the ce1 epitope show significant amino acid sequence homology (FIG. 2A). The sequence $^{312}$EDLLEE (SEQ ID NO: 20) in RIZ and the sequence $^{224}$EDLLNE (SEQ ID NO: 21) in E1A are likely sites for the ce1 epitope. To evaluate this possibility, an 11 amino acid peptide encompassing residues 310–320 in RIZ (ce1 peptide) KPEDLLEEPQS (SEQ ID NO: 7) and an overlapping 11 amino acid control peptide encompassing residues 304–314 containing the cr2 core motif of RIZ, peptide EIRCEEKPEDL (SEQ ID NO: 6), were synthesized by solid phase peptide synthesis and tested for their ability to block binding between anti-ce1 antibody and RIZ or E1A.

The ce1 peptide inhibited binding between anti-ce1 antibody and either $^{35}$S-RIZ318 or $^{35}$S-E1A 12S (E1A243); the cr2 peptide was not inhibitory (not shown). These experiments indicated that the ce1 epitope is located in the sequence $^{312}$EDLLEE (SEQ ID NO: 20) in RIZ and the homologous sequence $^{224}$EDLLNE (SEQ ID NO: 21) in E1A.

Anti-ce1 was tested for binding to a preformed RIZ-Rb complex to determine if the ce1 epitope is directly involved or closely associated with regions in the RIZ-Rb binding interface. In these experiments, $^{35}$S-labeled full-length Rb was preincubated with in vitro translated RIZ (215-462) to form the RIZ-Rb complex prior to adding anti-ce1 antibody for immunoprecipitation. In these experiments, the GST portion of GST-RIZ (215-462) had been previously removed by thrombin cleavage and was purified from any residual uncleaved fusion protein by adsorption with glutathionine-agarose.

The anti-ce1 antibody bound to the preformed RIZ-Rb complex (not shown). Although the binding could be characterized as weak, this was similar in reactivity with anti-ce1 binding with RIZ. Because no evidence of RIZ homo-oligomer formation was observed, Rb likely interacts directly with RIZ that also was bound by anti-ce1. The failure to observe homo-oligomer formation was based on the lack of binding between GST-RIZ (215-462) and $^{35}$S-labeled full length RIZ.

The above binding study also was performed in reverse order by first precomplexing $^{35}$S-labeled RIZ (1-575) with full-length Rb, then testing the complex for binding to anti-ce1 antibody. The result showed that the RIZ fragment bound anti-ce1 antibody regardless of whether RIZ had complexed with Rb (not shown). These experiments indicate that the ce1 epitope is not significantly involved in the interface between RIZ and Rb in the RIZ-Rb complex.

EXAMPLE IV

DNA- And GTP-Binding Activities of RIZ

To evaluate whether the zinc finger domains of RIZ can bind to DNA, the RIZ finger motifs 1 to 3 from amino acid position 245-573 or finger 4 to 6 from amino acid position 1114-1260 were expressed as GST fusion proteins, GSTZ13 and GSTZ46, respectively. The GST-RIZ fragments were purified by glutathionine agarose chromatography (Guan and Dixon, *Anal. Biochem.* 192:262–267 (1991), which is incorporated herein by reference) and evaluated for binding in a filter-based DNA-binding assay (Sukegawa and Blobel, *Cell* 72:29–38 (1993), which is incorporated herein by reference). To obtain GSTZ46, a fragment encoding RIZ (1114-1260) was made by PCR using primers 5'- GTGGTC-CAAG AAACATTC -3' (SEQ ID NO: 17) and 5'- TCGT-GTAAAG CTCTTCAG -3' (SEQ ID NO: 18) and pCM-VRIZ as template. The PCR fragment was cloned into pBKS+, then into pGEX-KG (Guan and Dixon, supra, 1991).

The filter-based DNA binding assay was performed by electrophoresing 0.5 µg of purified GST or GST-RIZ fusion proteins by SDS-PAGE and transferring the proteins to nitrocellulose. The proteins were renatured by incubating the nitrocellulose for 3 hr in binding buffer (50 mM Tris-HCl, pH 8, 100 mM KCl, 0.1% Triton X-100™, 10% glycerol, and 0.1 mM $ZnCl_2$). $^{32}$P-labeled, randomly sheared rat ovary genomic DNA was added to the buffer and the nitrocellulose was incubated for an additional 3 hr. Blots were washed 5 times in binding buffer, dried, then autoradiographed. In some experiments, the binding buffer contained 10 mM EDTA and 2 mM DTT but no $ZnCl_2$.

Figures 7A, 7B, 7C:
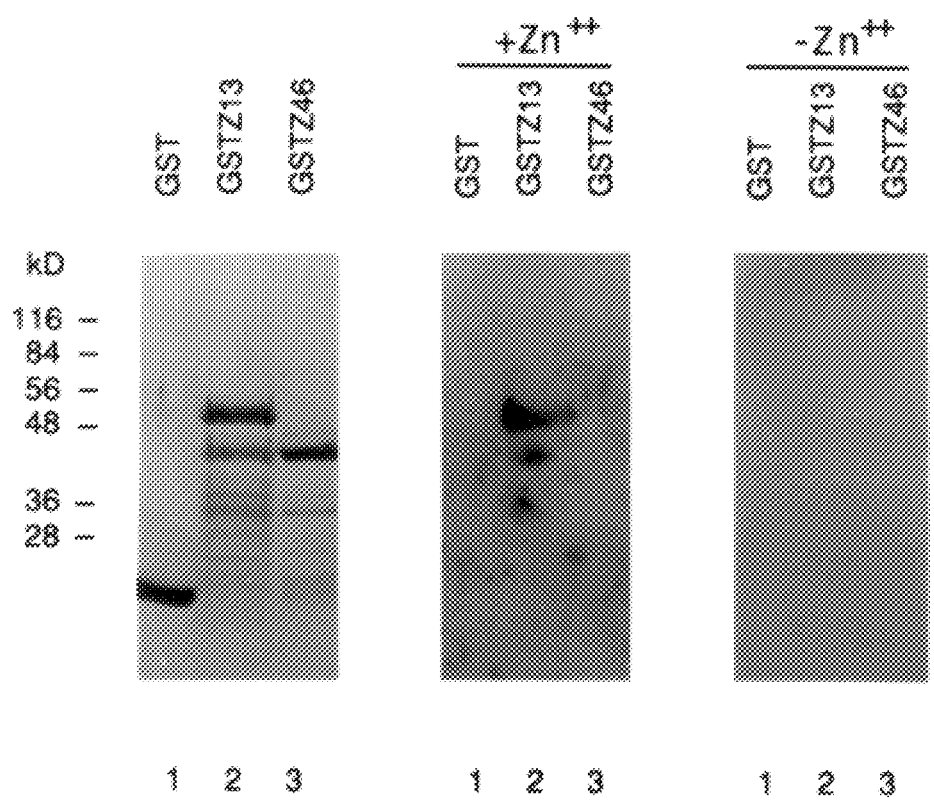
FIGS. 7A to 7C demonstrate that rat RIZ protein binds DNA.

The DNA filter binding assay showed that GSTZ13, containing zinc fingers 1 to 3 bound to rat DNA while GSTZ46, containing zinc fingers 4 to 6 did not bind (FIGS. 7A and 7B). In addition, RIZ fragment containing zinc fingers 1-3 bound to DNA in a $Zn^{++}$ ion dependent manner (FIG. 7). These results indicate that RIZ zinc finger domains 1 to 3 are active in binding DNA.

The GTPase domain of RIZ, which was defined by sequence homology, was evaluated to determine if it was functionally active. For these studies, a fragment of RIZ from amino acid position 760-949 (RIZ 760-949), containing the putative GTPase domain was expressed as a fusion to GST from the plasmid pKG-G and tested for binding to radiolabeled nucleotides. pKG-G was produced by PCR amplification of the nucleotide sequence encoding RIZ (760-949) using primers 5'- TCTCCACAGC ACAGCCCT -3' (SEQ ID No: 15), and 5'- GGATAAGGAG GCTGTCTG -3' (SEQ ID NO: 16) and pCMVRIZ as template. The fragment was cloned into pBSK+ and then into pGEX-KG, expressed and purified by glutathionine-agarose as described above. GST was also expressed from vector pGEX-KG and purified as described above.

To measure GTP-binding, 0.5 μg of GST-RIZ or control GST proteins were separated by SDS-PAGE and blotted onto nitrocellulose. Proteins were renatured in GTP-binding buffer (50 mM Tris-HCl, pH8, 100 mM KCl, 10% glycerol, 0.1% Triton X-100, and 2 mM $ZnSO_2$). The nitrocellulose was incubated for 30 min in GTP-binding buffer and then for 2 hr in GTP-binding buffer containing 1 μM α-$^{32}$P-GTP (800 Ci/mmol). The nitrocellulose was washed 5 times in GTP-binding buffer, dried and autoradiographed. In some samples, 20 mM unlabeled nucleotides were incubated with the nitrocellulose for 1 hr prior to the addition of α-$^{32}$P-GTP.

Figure 8A:
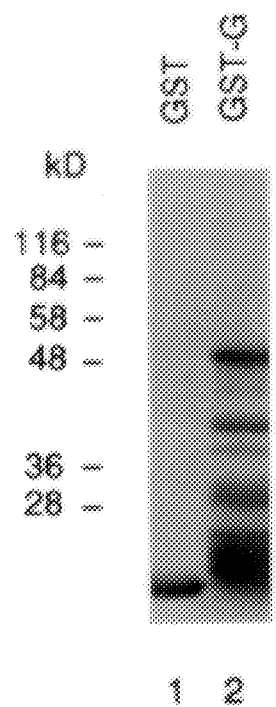
FIGS. 8A and 8B show the GTP-binding activity of rat RIZ GTPase domain (a.a. position 760-949).
Figure 8B:
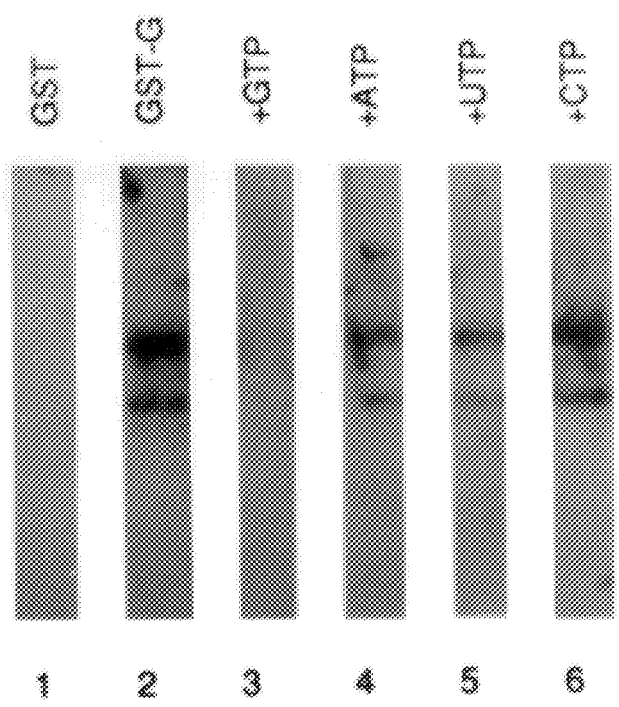

The RIZ GTPase fusion protein (GST-G), but not the control GST protein, bound to radiolabeled GTP (FIG. 8A and lanes 1 and 2 of FIG. 8B). Binding was specific for GTP, as an excess amount of unlabeled GTP inhibited binding of RIZ GTPase to radiolabeled GTP but excess unlabeled ATP, CTP, or UTP did not effect binding (FIG. 8B, lanes 3–6). These data indicate that the GTPase domain of RIZ is functionally active.

EXAMPLE V

Expression of RIZ in Cells, Tissues and Organs

This example provides methods to identify nucleic acid molecules encoding a RIZ in mammalian cells, tissues and organs.

RNA samples were obtained from rat tissues and from the mouse pituitary cell line Att-20 (ATCC #CCL 89) by extraction with RNAzol (Biotecx, Houston, Tex.) following manufacturer's procedures and purification of the mRNA by oligo dT cellulose chromatography using an oligo dT MRNA kit (Qiagen) using standard procedures. mRNA was also extracted as described above from a variety of human cell lines obtained from the American Type Culture Collection (Rockville, Md.). Northern blotting was performed using these various mRNAs and hybridization with a $^{32}$P-labeled rat RIZ (representing a.a. positions 245–883) according to standard procedures (Sambrook et. al. supra, 1989).

Figure 11A:
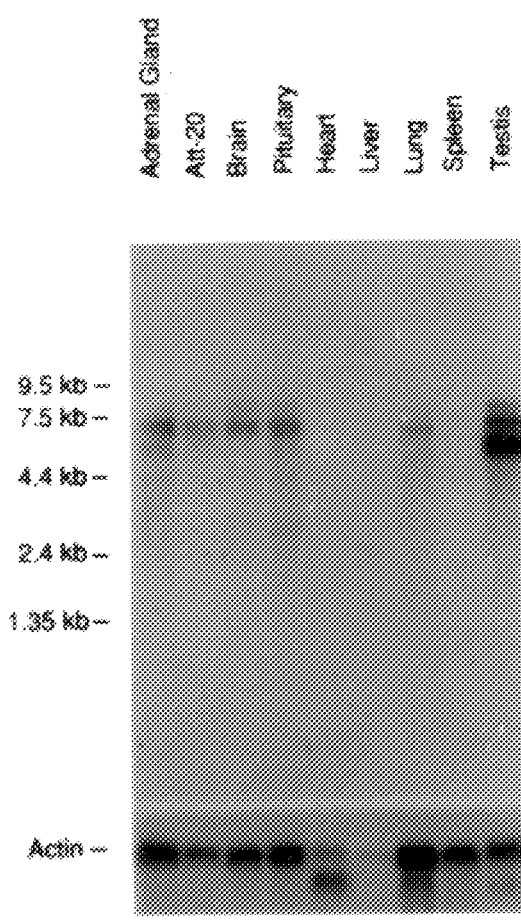
FIGS. 11A and 11B show RIZ mRNA expression in adult and fetal rat tissues, as indicated. Relative amounts of RNA loaded were compared by probing for Actin (see bottom of each blot). Numbers to the left of each figure indicate position of molecular weight markers as indicated (Kb: kilobases).

Northern blotting showed a major 7.2 kb major RIZ mRNA species primarily localized to rat neuroendocrine tissues (FIG. 11A). The testes showed a 5 kb mRNA species, which is smaller than the RIZ mRNA detected in the other organs or tissues.

Figure 11B:
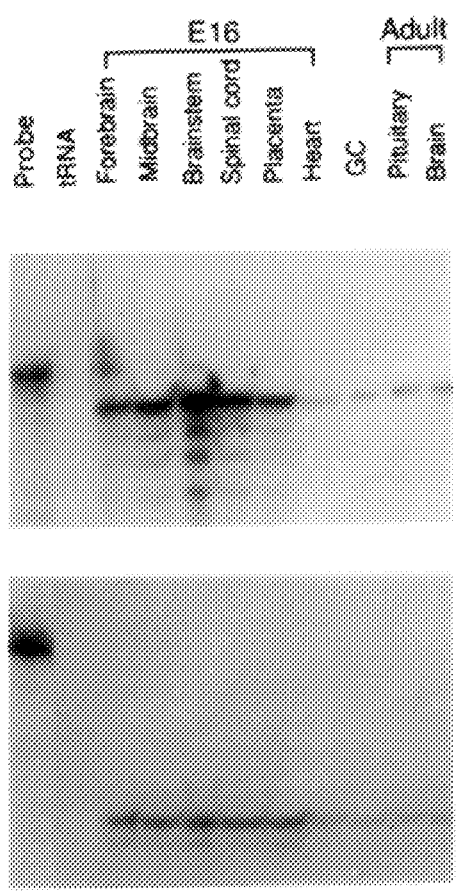

Further evaluation of mRNA expression was performed using an RNase protection method. The method was performed according to standard procedures using a $^{32}$p-labeled rat RIZ (representing a.a. position 463-574) was used as probe. The results showed abundant levels of RIZ mRNA in various neural tissues of a 16 day rat fetus as well as the placenta (FIG. 11B). In contrast, little if any mRNA was detected in adult rat tissues by this method.

Figure 12:
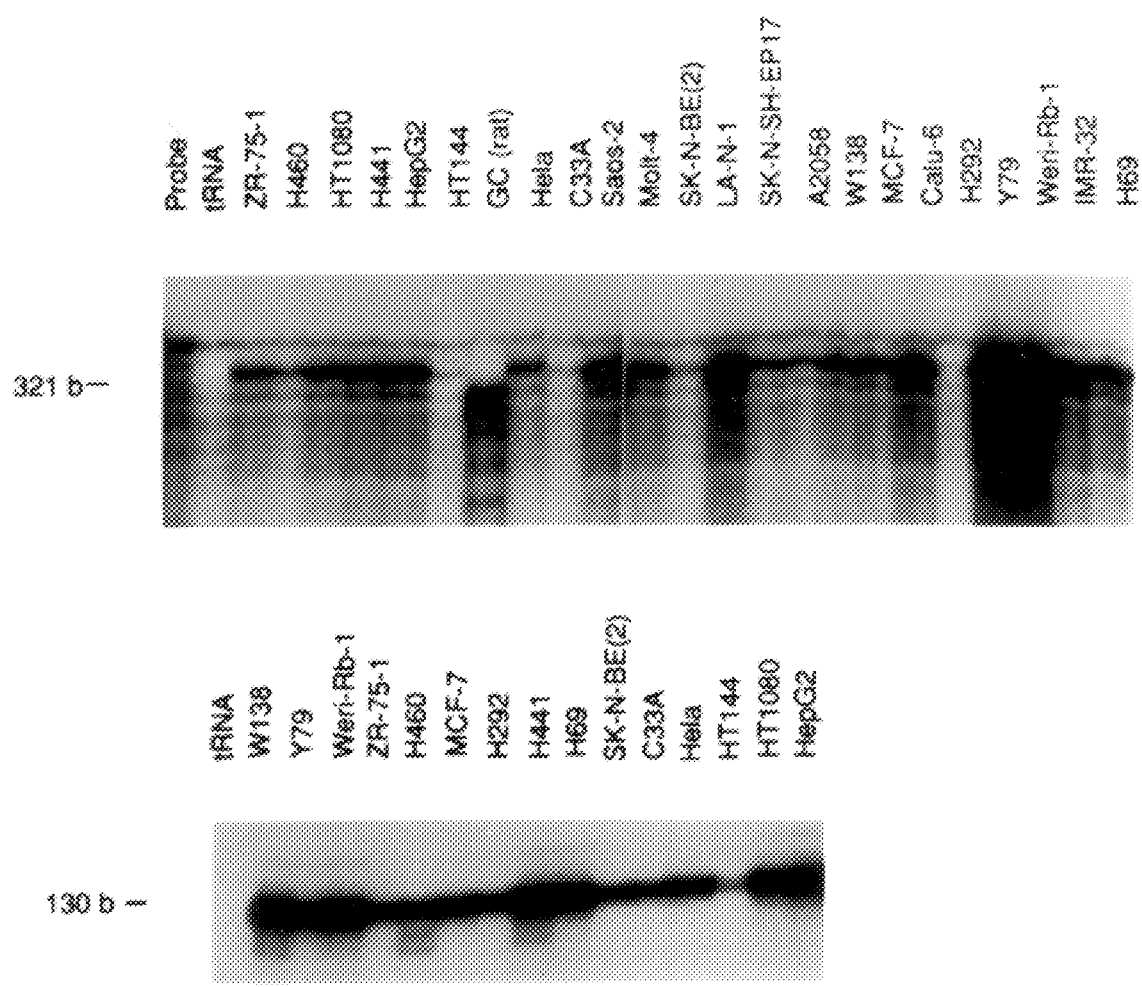
FIG. 12 presents an RNase protection experiment using mRNA from various human cell lines and from a rat cell line (indicated as GC). The 321 base pair marker (321 b) indicates protection of $^{32}$P-labeled rat RIZ (a.a. position 457-579) while the 130 base pair marker (130 b) indicates protection of Actin.

RNase protection showed that RIZ MRNA was detectable in the human retinoblastoma cell lines, Y79 and Weri-Rb-1, with lower levels of detection in a variety of other human cell lines (FIG. 12). These results indicate that RIZ mRNA is expressed in large amounts in neuroendocrine related tissues of mammals and can be involved in fetal development.

Several segments of human RIZ cDNA, encompassing the full length coding region were used as probes to screen a human placental genomic cosmid library to isolate the RIZ gene. Several genomic clones were isolated and the segments encoding RIZ were localized within the clones by restriction mapping and nucleotide sequencing. The genomic clones showed that the sequence encoding RIZ is distributed across eight exons in the gene, with the majority of RIZ sequence (4.3 kb) contained in exon 7.

EXAMPLE VI

Analysis of the RIZ Gene in Normal and Tumor Cells

This example provides methods to detect the RIZ gene by direct chromosomal analysis and to evaluate mutations in the RIZ gene in tumor cells.

A. Chromosomal Localization of the Human RIZ Gene

A cosmid clone with a 35 kb insert that contains exons 7 and 8 was used as a probe for fluorescence in situ hybridization (FISH) on R-banded metaphase chromosomes to detect the chromosomal localization of the human RIZ gene. The method for FISH was performed as described previously (Takahashi et al., *Human Genetics* 88:119–121 (1991), which is incorporated herein by reference). Cot-1 DNA (BRL, Gaitherburg, Md.) was used for the suppression of repetitive sequences present in this clone according to methods described by Lichter et al., (Lichter et. al., *Proc. Natl. Acad. Sci., USA* 87:6634–6638 (1990), which is incorporated herein by reference) using a 20 fold excess of Cot-1 DNA. Ektachrome film (Kodak, ASA100) was used for the microphotography (filter combination, Nikon B-2A).

Of 100 R-banded metaphase plates evaluated by the FISH method, 52 plates showed hybridization of the probe to both chromatids of chromosome 1 at band p36.13–p36.23, 44 plates showed hybridization of the probe only to one chromatid of chromosome 1, and four plates showed no hybridization.

Further localization of the RIZ gene to chromosome 1p36 was accomplished at the molecular level by YAC cloning. A CEPH-derived human mega-YAC library (CEPH, France) was screened by PCR using two oligonucleotide primers to amplify a 290 bp fragment within the RIZ exon 7. YAC DNA was amplified in a total volume of 10 μl containing 1xPCR buffer (50 mM KCl/10 mM Tris-HCl, pH 8.3/1.5 mM $MgCl_2$), 200 μM of each dNTP, 0.3 μM of each primer (SSO 81: 5'CCAGAACCAGACGAGCGATT3' (SEQ ID NO: 92) and SSO 82: 5'AGTTCTGGGGATTTGCATG3' (SEQ ID NO: 93)), 0.2 U Taq DNA polymerase (Perkin Elmer, Norwalk, Conn.). One of the primers was end-labeled using $^{32}$P-γ-ATP and T4 polynucleotide kinase. The PCR fragments were analyzed by acrylamide gel electrophoresis followed by autoradiography.

PCR screening of the CEPH human mega-YAC library for RIZ gene sequences identified two YAC clones, 796H4 and 807H7. A search of Genethon human genome database (Genethon, Paris France) showed that the clones contained the polymorphic marker D1S228, which maps to chromosome 1p36 (Gyapay et al., *Nat. Genet.* 7:246–339 (1994); Weissenbach et al., *Nature* 359:794–801 (1992) and Cohen et al., *Nature* 366:698–701 (1993), each of which is incorporated herein by reference)). Thus, these results indicate that the RIZ gene is localized to chromosome 1p36.

B. Allele-Specific RIZ Expression in Human Melanoma Cells

Genomic DNA from blood and placental samples of normal subjects and tumor cell lines were prepared by incubating cells for 1 hr at 55° C. in 50 mM Tris-HCl, pH 8.0/100 mM EDTA/0.5% SDS/500 µg/ml Proteinase K. After phenol/chloroform and chloroform extraction, the DNA was precipitated. RNA was prepared from a pellet of $5-10\times10^6$ PBS washed cells or from fetal tissues using RNAzol (Biotecx Laboratories, Houston, Tex.).

Southern blots and were performed on melanoma cell DNA and RNA, respectively, using a RIZ cDNA a 1 kb human RIZ cDNA probe (1.1). The results showed identification of the appropriate sized bands for the RIZ gene and mRNA transcripts in the melanoma cells, indicating no gross abnormalities in the RIZ gene in these cells.

To determine whether both alleles of RIZ were active in melanoma cells, the frequency of the two allelic variants of RIZ were determined for melanoma and compared with the frequency in the population. RIZ genotyping was performed by amplification of a 290 bp fragment representing RIZ (230-330) using PCR on genomic DNA isolated from 28 normal individuals and 26 human melanoma cell lines. PCR amplification of the 290 bp fragment was performed on 100 ng of genomic DNA in a total volume of 50 µl containing 1x PCR buffer, 200 µM of each dNTP, 0.3 µM of each primer (SSO 81+SSO 82), and 1 U of Taq DNA polymerase (Perkin Elmer). The PCR product was sequenced to determine the codons encoding RIZ a.a. position 283. The RIZ D283 allele encodes an Asp residue at a.a. position 283 by the codon GAT, while the RIZ E283 allele encodes a Glu residue at a.a. position 283 by the codon GAA.

Genotyping of DNA from 28 normal individuals showed that fifteen were homozygous for the RIZ D283 allele (53%) three were homozygous for the E283 allele (10%) and ten were heterozygous (35%). Thus, the overall frequency of the RIZ E283 allele in the population of normal individuals studies was estimated to be about 28.5%.

Genotyping the DNA of 26 melanoma cell lines showed that fifteen were homozygous for the RIZ D283 allele (57%), five were homozygous for RIZ E283 (19%) and six were heterozygous (23%). This reduced frequency of heterozygous alleles in the population of melanoma cell lines tested (23%) compared to normal individuals tested (35%), indicates that a loss of heterozygosity occurs at the 1p36 locus in human melanoma.

RNA samples from the 6 heterozygous melanoma cell lines were sequenced to determine if both alleles were transcribed in the cell. Sequencing was performed on DNA products produced by reverse transcription-PCR (RT-PCR) amplification using specific RIZ primers. RT-PCR amplification was performed according to the manufacturer's instructions (GeneAmp RNA PCR kit, Perkin Elmer). A 640 bp fragment encoding RIZ exons 5–7 was obtained from transcription of 1 µg of total RNA using the SSO 82 primer (SEQ ID NO: 93) and PCR amplification using the SSO 24 primer (5'GCGAGGAGCTCCTGGTCTGG3'; SEQ ID NO: 92) and the SSO 82 primer (SEQ ID NO: 93). The amplified fragment was gel purified and sequenced using primer SSO 82 and a CircumVent™ Thermal Cycle DNA Sequencing kit (New England Biolabs, Mass.). The sequencing products were analyzed on a 6% sequencing gel.

Sequencing of amplified and transcribed RIZ mRNA from heterozygous melanoma cell lines showed that both RIZ alleles were transcribed in four of the lines while only the E283 RIZ allele was detected as transcribed in cell line HT144 (ATCC #HTB 63) and SK-MEL-23. In contrast, sequencing of amplified and transcribed mRNA from RIZ heterozygotes representing seven non-melanoma cell lines and two normal human placental tissues showed that both RIZ alleles were transcribed. Sequence analysis of the expressed allele in HT144 and SK-MEL-23 melanoma cells revealed no mutations in the RIZ encoding sequence. RIZ mRNA amplification was accomplished in 15 of 15 melanoma cell lines analyzed, indicating that homozygous RIZ gene inactivation was not present in this sample.

Regions in human chromosome 1 in the melanoma cell lines HT144 and SK-MEL-23 were evaluated for gross deletions to determine a genetic basis for the failure of these cells to produce detectable mRNA encoding the RIZ D283 allele. Gross deletion in chromosome 1 was determined by PCR amplification of polymorphic $(C-A)_2$ repeat microsatellite markers, including D1S228, D1S489 and D1S507. D1S228 is the only genetic marker in the RIZ YAC clone 796H4 that has an insert of 340 kb, indicating that the distance between RIZ and D1S228 is less than 340 kb. D1S489 is ~9-centamorgan (cM) telomeric and D1S507 ~5-cM centromeric from D1S228 (Gyapay et al., supra, 1994). Oligonucleotide primer pairs for D1S223, D1S489 and D1S507 were used to amplify 100 ng of genomic DNA. One primer was end-labeled with $^{32}$p and the amplified fragments were analyzed by sequencing and autoradiography.

PCR amplification of chromosome 1 microsatellite markers in the melanoma cell line DNA showed two different length fragments of the expected size range for each of the three markers examined, indicating heterozygosity at all three loci. These results showed that loss of transcription of the D283 allele in HT144 and SK-MEL-23 cells was not likely due to a gross deletion in the genomic DNA near the RIZ allele.

The 6 melanoma cell lines heterozygous for RIZ were evaluated to determine the amount of RIZ protein produced by the cells. RIZ protein level was estimated qualitatively by immunoprecipition of RIZ from cell extracts with anti-RIZ antibody followed by immunoblotting the isolated RIZ with the anti-RIZ antibody. The melanoma cells lines HT144 and SK-MEL-23 produced about 50% less RIZ protein than the other melanoma cell lines tested. These data indicate that the loss of expression of the RIZ D283 allele in these cell lines results in a decrease in overall expression of RIZ in the cell.

Although the invention has been described with reference to the above-provided examples, it should be understood that various modifications can be made without departing from the spirit of the invention. Accordingly, the invention is limited only by the claims that follow.

I claim:

1. A substantially purified active fragment of a mammalian retinoblastoma protein interacting zinc finger protein, said active fragment comprising the amino acid sequence EIRCEEKPEDL (SEQ ID NO: 6), wherein said active fragment binds to retinoblastoma protein.

2. A substantially purified active fragment of a mammalian retinoblastoma protein interacting zinc finger protein, said active fragment comprising the amino acid sequence EIRCDEKPEDL (SEQ ID NO: 91), wherein said active fragment binds to retinoblastoma protein.

3. Substantially purified human retinoblastoma protein interacting zinc finger protein, comprising the amino acid sequence shown in FIG. 9 (SEQ ID NO: 4).

4. Substantially purified human retinoblastoma protein interacting zinc finger protein, comprising the amino acid sequence shown in FIG. 9 (SEQ ID NO: 4), except wherein glutamic acid is substituted for aspartic acid at amino acid position 283.

5. Substantially purified rat retinoblastoma protein interacting zinc finger protein, comprising the amino acid sequence shown in FIG. 1 (SEQ ID NO: 2).

6. A substantially purified mutant human retinoblastoma protein interacting zinc finger protein, comprising the amino acid sequence shown in FIG. 9 (SEQ ID NO: 4), except wherein tyrosine is substituted for cysteine at amino acid position 106.

* * * * *

UNITED STATES PATENT AND TRADEMARK OFFICE
CERTIFICATE OF CORRECTION

PATENT NO. : 5,831,008
DATED : Nov. 3, 1998
INVENTOR(S) : Shi Huang

It is certified that error appears in the above-identified patent and that said Letters Patent is hereby corrected as shown below:

In column 2, line 33, please delete "79" and replace therefor with --91--.

In column 7, Table 1 legend, please delete "Ray Chaudhuri and Park (1992)." and replace therefor with --Raychaudhuri and Park, Nature 359:251-254 (1992).--.

Signed and Sealed this

Twenty-ninth Day of May, 2001

Attest:

NICHOLAS P. GODICI

Attesting Officer          Acting Director of the United States Patent and Trademark Office

SEQUENCE LISTING ( 1 ) GENERAL INFORMATION:

( i i i ) NUMBER OF SEQUENCES: 93

( 2 ) INFORMATION FOR SEQ ID NO:1:

( i ) SEQUENCE CHARACTERISTICS:
        ( A ) LENGTH: 6171 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 157..5275

( x i ) SEQUENCE DESCRIPTION: SEQ ID NO:1:

```
GCCAAGATGG  CGGCGGCGCG  GCCGCGGGCG  CCAGGGCGAC  GGCGGCGGCT  GAGGCTCTGG         60

GCTCGCTGAA  GCGTTGGCAC  GTCGCGCTCT  GGGCTCATGT  AATCAAAGAA  GTTTCTTTGT        120

TGTGTGTATC  TTCACAGAAC  ACAACAGGAA  TTGAAA ATG CAT CAG AAC ACT GAG            174
                                          Met His Gln Asn Thr Glu
                                           1               5

TCT GTG GCA GCC ACT GAG ACT CTG GCT GAG GTA CCT GAA CAT GTG CTT              222
Ser Val Ala Ala Thr Glu Thr Leu Ala Glu Val Pro Glu His Val Leu
             10                  15                  20

CGA GGA CTT CCA GAG GAA GTA AGA CTT TTC CCA TCT GCA GTC GAC AAG              270
Arg Gly Leu Pro Glu Glu Val Arg Leu Phe Pro Ser Ala Val Asp Lys
         25                  30                  35

ACT CGG ATT GGT GTC TGG GCT ACT AAA CCA ATT TTA AAA GGG AAA AAG              318
Thr Arg Ile Gly Val Trp Ala Thr Lys Pro Ile Leu Lys Gly Lys Lys
     40                  45                  50

TTT GGG CCA TTT GTT GGT GAT AAG AAG AAG AGA TCC CAG GTT AGG AAT              366
Phe Gly Pro Phe Val Gly Asp Lys Lys Lys Arg Ser Gln Val Arg Asn
 55                  60                  65                  70

AAT GTG TAC ATG TGG GAG GTC TAC TAC CCA AAT TTG GGG TGG ATG TGC              414
Asn Val Tyr Met Trp Glu Val Tyr Tyr Pro Asn Leu Gly Trp Met Cys
                 75                  80                  85

ATT GAT GCC ACC GAT CCG GAG AAG GGC AAC TGG CTA CGC TAT GTG AAC              462
Ile Asp Ala Thr Asp Pro Glu Lys Gly Asn Trp Leu Arg Tyr Val Asn
             90                  95                 100

TGG GCT TGC TCA GGA GAA GAG CAG AAT TTA TTT CCA CTG GAA ATC AAC              510
Trp Ala Cys Ser Gly Glu Glu Gln Asn Leu Phe Pro Leu Glu Ile Asn
            105                 110                 115

AGA GCC ATT TAC TAT AAA ACC TTA AAG CCA ATC GCG CCT GGC GAG GAG              558
Arg Ala Ile Tyr Tyr Lys Thr Leu Lys Pro Ile Ala Pro Gly Glu Glu
        120                 125                 130

CTC CTG GTC TGG TAC AAT GGG GAA GAC AAC CCT GAG ATA GCA GCT GCG              606
Leu Leu Val Trp Tyr Asn Gly Glu Asp Asn Pro Glu Ile Ala Ala Ala
135                 140                 145                 150

ATT GAG GAA GAG CGA GCC AGC GCC CGG AGC AAG CGG AGC TCC CCG AAG              654
Ile Glu Glu Glu Arg Ala Ser Ala Arg Ser Lys Arg Ser Ser Pro Lys
                155                 160                 165

AGC CGC AGA GGG AAG AAG AAA TCA CAC GAG AAC AAA AAC AAA GGC ATC              702
Ser Arg Arg Gly Lys Lys Lys Ser His Glu Asn Lys Asn Lys Gly Ile
            170                 175                 180

AGA ACC CAC CCC ACA CAG CTG AAG GCA AGT GAG CTG GAC TCT ACC TTT              750
Arg Thr His Pro Thr Gln Leu Lys Ala Ser Glu Leu Asp Ser Thr Phe
        185                 190                 195

GCA AAC ATG AGG GGC TCT GCA GAA GGT CCA AAA GAA GAG GAT GAG AGG              798
Ala Asn Met Arg Gly Ser Ala Glu Gly Pro Lys Glu Glu Asp Glu Arg
```

|  |  |  |  |  |  |  |  |  |  |  |  |  |  |  |  |
|---|---|---|---|---|---|---|---|---|---|---|---|---|---|---|---|
|  |  |  |  | 200 |  |  |  |  | 205 |  |  |  |  | 210 |  |
| CCT | TTG | GCT | TCG | GCA | CCT | GAG | CAG | CCA | GCC | CCT | CTG | CCG | GAG | GTG | GGG | 846
| Pro | Leu | Ala | Ser | Ala | Pro | Glu | Gln | Pro | Ala | Pro | Leu | Pro | Glu | Val | Gly |
| 215 |  |  |  |  | 220 |  |  |  |  | 225 |  |  |  |  | 230 |

| AAT | CAA | GAT | GCA | GTT | CCA | CAG | GTG | GCC | ATC | CCT | CTC | CCT | GCC | TGC | GAG | 894
|---|---|---|---|---|---|---|---|---|---|---|---|---|---|---|---|
| Asn | Gln | Asp | Ala | Val | Pro | Gln | Val | Ala | Ile | Pro | Leu | Pro | Ala | Cys | Glu |
|  |  |  |  | 235 |  |  |  |  | 240 |  |  |  |  | 245 |  |

| CCA | CAG | CCA | GAG | GTA | GAT | GGG | AAA | CAA | GAA | GTC | ACA | GAC | TGT | GAG | GTC | 942
|---|---|---|---|---|---|---|---|---|---|---|---|---|---|---|---|
| Pro | Gln | Pro | Glu | Val | Asp | Gly | Lys | Gln | Glu | Val | Thr | Asp | Cys | Glu | Val |
|  |  |  | 250 |  |  |  |  | 255 |  |  |  |  | 260 |  |  |

| AAT | GAT | GTG | GAG | GAA | GAG | GAG | CTG | GAA | GAG | GAA | GAG | GAG | CTG | GAA | GAG | 990
|---|---|---|---|---|---|---|---|---|---|---|---|---|---|---|---|
| Asn | Asp | Val | Glu | Glu | Glu | Glu | Leu | Glu | Glu | Glu | Glu | Glu | Leu | Glu | Glu |
|  |  | 265 |  |  |  |  | 270 |  |  |  |  | 275 |  |  |  |

| GAG | GAG | GAG | GAG | GAG | TTG | GGA | GAA | GAT | GGG | GTA | GAA | GAA | GCA | GAC | ATG | 1038
|---|---|---|---|---|---|---|---|---|---|---|---|---|---|---|---|
| Glu | Glu | Glu | Glu | Glu | Leu | Gly | Glu | Asp | Gly | Val | Glu | Glu | Ala | Asp | Met |
|  |  | 280 |  |  |  |  | 285 |  |  |  |  | 290 |  |  |  |

| CCG | AAT | GAA | AGC | TCT | GCG | AAA | GAG | CCG | GAG | ATC | CGG | TGT | GAA | GAA | AAG | 1086
|---|---|---|---|---|---|---|---|---|---|---|---|---|---|---|---|
| Pro | Asn | Glu | Ser | Ser | Ala | Lys | Glu | Pro | Glu | Ile | Arg | Cys | Glu | Glu | Lys |
| 295 |  |  |  |  | 300 |  |  |  |  | 305 |  |  |  |  | 310 |

| CCA | GAA | GAC | TTA | TTA | GAA | GAG | CCA | CAG | AGC | ATG | TCG | AAT | GAA | GCT | CGT | 1134
|---|---|---|---|---|---|---|---|---|---|---|---|---|---|---|---|
| Pro | Glu | Asp | Leu | Leu | Glu | Glu | Pro | Gln | Ser | Met | Ser | Asn | Glu | Ala | Arg |
|  |  |  |  | 315 |  |  |  |  | 320 |  |  |  |  | 325 |  |

| GAA | GAC | TCT | CCA | GAC | GTG | ACC | CCT | CCT | CCC | CAC | ACT | CCC | AGA | GCT | AGA | 1182
|---|---|---|---|---|---|---|---|---|---|---|---|---|---|---|---|
| Glu | Asp | Ser | Pro | Asp | Val | Thr | Pro | Pro | Pro | His | Thr | Pro | Arg | Ala | Arg |
|  |  |  | 330 |  |  |  |  | 335 |  |  |  |  | 340 |  |  |

| GAG | GAG | GCC | AAC | GGT | GAT | GTA | CTT | GAG | ACA | TTT | ATG | TTT | CCG | TGT | CAG | 1230
|---|---|---|---|---|---|---|---|---|---|---|---|---|---|---|---|
| Glu | Glu | Ala | Asn | Gly | Asp | Val | Leu | Glu | Thr | Phe | Met | Phe | Pro | Cys | Gln |
|  |  |  | 345 |  |  |  |  | 350 |  |  |  |  | 355 |  |  |

| CAC | TGT | GAA | AGA | AAA | TTT | GCA | ACG | AAG | CAG | GGG | CTA | GAG | CGT | CAC | ATG | 1278
|---|---|---|---|---|---|---|---|---|---|---|---|---|---|---|---|
| His | Cys | Glu | Arg | Lys | Phe | Ala | Thr | Lys | Gln | Gly | Leu | Glu | Arg | His | Met |
|  |  | 360 |  |  |  |  | 365 |  |  |  |  | 370 |  |  |  |

| CAC | ATC | CAC | ATT | TCT | ACC | ATC | AAT | CAT | GCT | TTC | AAG | TGC | AAG | TAC | TGT | 1326
|---|---|---|---|---|---|---|---|---|---|---|---|---|---|---|---|
| His | Ile | His | Ile | Ser | Thr | Ile | Asn | His | Ala | Phe | Lys | Cys | Lys | Tyr | Cys |
| 375 |  |  |  |  | 380 |  |  |  |  | 385 |  |  |  |  | 390 |

| GGG | AAA | CGG | TTT | GGC | ACA | CAG | ATT | AAC | AGG | AGG | CGG | CAT | GAA | CGG | CGC | 1374
|---|---|---|---|---|---|---|---|---|---|---|---|---|---|---|---|
| Gly | Lys | Arg | Phe | Gly | Thr | Gln | Ile | Asn | Arg | Arg | Arg | His | Glu | Arg | Arg |
|  |  |  |  | 395 |  |  |  |  | 400 |  |  |  |  | 405 |  |

| CAC | GAA | ACG | GGG | TTG | AAG | AGA | AGA | CCC | AGC | ATG | ACT | TTA | CAG | TCC | TCA | 1422
|---|---|---|---|---|---|---|---|---|---|---|---|---|---|---|---|
| His | Glu | Thr | Gly | Leu | Lys | Arg | Arg | Pro | Ser | Met | Thr | Leu | Gln | Ser | Ser |
|  |  |  | 410 |  |  |  |  | 415 |  |  |  |  | 420 |  |  |

| GAG | GAT | CCA | GAT | GAT | GGC | AAG | GGG | GAA | AAT | GTT | ACT | TCT | AAA | GAT | GAG | 1470
|---|---|---|---|---|---|---|---|---|---|---|---|---|---|---|---|
| Glu | Asp | Pro | Asp | Asp | Gly | Lys | Gly | Glu | Asn | Val | Thr | Ser | Lys | Asp | Glu |
|  |  |  | 425 |  |  |  |  | 430 |  |  |  |  | 435 |  |  |

| TCA | AGT | CCA | CCT | CAA | CTC | GGG | CAA | GAC | TGT | TTG | ATA | TTG | AAC | TCA | GAG | 1518
|---|---|---|---|---|---|---|---|---|---|---|---|---|---|---|---|
| Ser | Ser | Pro | Pro | Gln | Leu | Gly | Gln | Asp | Cys | Leu | Ile | Leu | Asn | Ser | Glu |
|  |  | 440 |  |  |  |  | 445 |  |  |  |  | 450 |  |  |  |

| AAA | ACC | TCA | CAG | GAA | GTA | CTG | AAT | TCA | TCT | TTT | GTG | GAA | GAA | AAT | GGT | 1566
|---|---|---|---|---|---|---|---|---|---|---|---|---|---|---|---|
| Lys | Thr | Ser | Gln | Glu | Val | Leu | Asn | Ser | Ser | Phe | Val | Glu | Glu | Asn | Gly |
| 455 |  |  |  |  | 460 |  |  |  |  | 465 |  |  |  |  | 470 |

| GAA | GTT | AAA | GAA | CTT | CAT | CCG | TGC | AAA | TAC | TGC | AAA | AAG | GTA | TTT | GGA | 1614
|---|---|---|---|---|---|---|---|---|---|---|---|---|---|---|---|
| Glu | Val | Lys | Glu | Leu | His | Pro | Cys | Lys | Tyr | Cys | Lys | Lys | Val | Phe | Gly |
|  |  |  |  | 475 |  |  |  |  | 480 |  |  |  |  | 485 |  |

| ACT | CAC | ACC | AAT | ATG | AGA | CGA | CAT | CAG | CGT | AGA | GTT | CAT | GAG | CGC | CAC | 1662
|---|---|---|---|---|---|---|---|---|---|---|---|---|---|---|---|
| Thr | His | Thr | Asn | Met | Arg | Arg | His | Gln | Arg | Arg | Val | His | Glu | Arg | His |
|  |  |  | 490 |  |  |  |  | 495 |  |  |  |  | 500 |  |  |

| CTG | ATT | CCC | AAA | GGT | GTC | AGG | CGA | AAA | GGA | GGA | CTT | CTG | GAA | GAG | CCA | 1710
|---|---|---|---|---|---|---|---|---|---|---|---|---|---|---|---|
| Leu | Ile | Pro | Lys | Gly | Val | Arg | Arg | Lys | Gly | Gly | Leu | Leu | Glu | Glu | Pro |
|  |  |  | 505 |  |  |  |  | 510 |  |  |  |  | 515 |  |  |

| CAG | CCA | CCA | GCA | GAG | CAG | GCT | CCA | CCC | TCC | CAG | AAT | GTC | TAT | GTC | CCA | 1758
|---|---|---|---|---|---|---|---|---|---|---|---|---|---|---|---|
| Gln | Pro | Pro | Ala | Glu | Gln | Ala | Pro | Pro | Ser | Gln | Asn | Val | Tyr | Val | Pro |

|     |     |     |     | 520 |     |     |     |     | 525 |     |     |     |     | 530 |     |      |
|-----|-----|-----|-----|-----|-----|-----|-----|-----|-----|-----|-----|-----|-----|-----|-----|------|
| AGC | ACA | GAG | CCA | GAG | GAG | GAA | GGG | GAA | ACA | GAT | GAC | GTG | TAC | ATC | ATG | 1806 |
| Ser | Thr | Glu | Pro | Glu | Glu | Glu | Gly | Glu | Thr | Asp | Asp | Val | Tyr | Ile | Met |      |
| 535 |     |     |     |     | 540 |     |     |     |     | 545 |     |     |     |     | 550 |      |
| GAC | ATT | TCT | AGC | AAC | ATC | TCT | GAA | AAC | CTA | AAT | TAC | TAT | ATT | GAC | GGT | 1854 |
| Asp | Ile | Ser | Ser | Asn | Ile | Ser | Glu | Asn | Leu | Asn | Tyr | Tyr | Ile | Asp | Gly |      |
|     |     |     |     | 555 |     |     |     |     | 560 |     |     |     |     | 565 |     |      |
| AAG | ATT | CAG | ACC | AAC | AGC | AGC | ACT | AGT | AAC | TGT | GAT | GTG | ATT | GAG | ATG | 1902 |
| Lys | Ile | Gln | Thr | Asn | Ser | Ser | Thr | Ser | Asn | Cys | Asp | Val | Ile | Glu | Met |      |
|     |     |     | 570 |     |     |     |     | 575 |     |     |     |     | 580 |     |     |      |
| GAG | TCT | AAT | TCT | GCA | CAC | TTG | TAT | GGC | ATA | GAC | TGT | CTG | CTC | ACT | CCA | 1950 |
| Glu | Ser | Asn | Ser | Ala | His | Leu | Tyr | Gly | Ile | Asp | Cys | Leu | Leu | Thr | Pro |      |
|     |     | 585 |     |     |     |     | 590 |     |     |     |     | 595 |     |     |     |      |
| GTG | ACC | GTG | GAG | ATT | ACT | CAG | AAC | ATA | AAG | AGC | ACT | CAG | GTC | TCT | GTG | 1998 |
| Val | Thr | Val | Glu | Ile | Thr | Gln | Asn | Ile | Lys | Ser | Thr | Gln | Val | Ser | Val |      |
|     |     | 600 |     |     |     |     | 605 |     |     |     |     | 610 |     |     |     |      |
| ACA | GAT | GAT | CTT | CTC | AAA | GAC | TCT | CCC | AGC | AGC | ACA | AAT | TGT | GAG | TCT | 2046 |
| Thr | Asp | Asp | Leu | Leu | Lys | Asp | Ser | Pro | Ser | Ser | Thr | Asn | Cys | Glu | Ser |      |
| 615 |     |     |     |     | 620 |     |     |     |     | 625 |     |     |     |     | 630 |      |
| AAG | AAA | CGG | AGG | ACT | GCC | AGT | CCA | CCT | GTG | CTC | CCC | AAA | ATT | AAA | ACG | 2094 |
| Lys | Lys | Arg | Arg | Thr | Ala | Ser | Pro | Pro | Val | Leu | Pro | Lys | Ile | Lys | Thr |      |
|     |     |     |     | 635 |     |     |     |     | 640 |     |     |     |     | 645 |     |      |
| GAG | ACG | GAG | TCT | GAT | TCC | ACA | GCA | CCC | TCG | TGT | TCC | TTA | AGT | CTG | CCC | 2142 |
| Glu | Thr | Glu | Ser | Asp | Ser | Thr | Ala | Pro | Ser | Cys | Ser | Leu | Ser | Leu | Pro |      |
|     |     |     | 650 |     |     |     |     | 655 |     |     |     |     | 660 |     |     |      |
| CTG | AGC | ATA | TCC | ACA | GCC | GAG | GTG | GTG | TCC | TTC | CAT | AAA | GAG | AAG | GGC | 2190 |
| Leu | Ser | Ile | Ser | Thr | Ala | Glu | Val | Val | Ser | Phe | His | Lys | Glu | Lys | Gly |      |
|     |     |     | 665 |     |     |     |     | 670 |     |     |     |     | 675 |     |     |      |
| GTC | TAT | TTG | TCG | TCC | AAG | CTC | AAG | CAG | CTT | CTT | CAG | ACC | CAG | GAC | AAG | 2238 |
| Val | Tyr | Leu | Ser | Ser | Lys | Leu | Lys | Gln | Leu | Leu | Gln | Thr | Gln | Asp | Lys |      |
|     |     | 680 |     |     |     |     | 685 |     |     |     |     | 690 |     |     |     |      |
| CTG | ACC | CTT | CCT | GCA | GGG | TTT | TCA | GCA | GCT | GAG | ATT | CCT | AAG | TTA | GGT | 2286 |
| Leu | Thr | Leu | Pro | Ala | Gly | Phe | Ser | Ala | Ala | Glu | Ile | Pro | Lys | Leu | Gly |      |
| 695 |     |     |     |     | 700 |     |     |     |     | 705 |     |     |     |     | 710 |      |
| CCC | GTG | TGC | GCG | TCT | GCT | CCT | GCA | TCC | ATG | TTG | CCC | GTG | ACC | TCT | AGT | 2334 |
| Pro | Val | Cys | Ala | Ser | Ala | Pro | Ala | Ser | Met | Leu | Pro | Val | Thr | Ser | Ser |      |
|     |     |     |     | 715 |     |     |     |     | 720 |     |     |     |     | 725 |     |      |
| AGG | TTT | AAG | AGA | CGC | ACC | AGC | TCT | CCA | CCG | AGC | TCT | CCA | CAG | CAC | AGC | 2382 |
| Arg | Phe | Lys | Arg | Arg | Thr | Ser | Ser | Pro | Pro | Ser | Ser | Pro | Gln | His | Ser |      |
|     |     |     | 730 |     |     |     |     | 735 |     |     |     |     | 740 |     |     |      |
| CCT | GCC | CTT | CGA | GAC | TTC | GGG | AAA | CCA | AAT | GAT | GGG | AAA | GCA | GCA | TGG | 2430 |
| Pro | Ala | Leu | Arg | Asp | Phe | Gly | Lys | Pro | Asn | Asp | Gly | Lys | Ala | Ala | Trp |      |
|     |     |     | 745 |     |     |     |     | 750 |     |     |     |     | 755 |     |     |      |
| ACA | GAC | ACA | GTC | CTG | ACT | TCC | AAG | AAA | CCC | AAG | TTA | GAA | AGT | CGT | AGT | 2478 |
| Thr | Asp | Thr | Val | Leu | Thr | Ser | Lys | Lys | Pro | Lys | Leu | Glu | Ser | Arg | Ser |      |
|     | 760 |     |     |     |     | 765 |     |     |     |     | 770 |     |     |     |     |      |
| GAC | TCA | CCA | GCA | TGG | AGT | TTG | TCT | GGG | AGA | GAT | GAA | AGA | GAA | ACC | GGA | 2526 |
| Asp | Ser | Pro | Ala | Trp | Ser | Leu | Ser | Gly | Arg | Asp | Glu | Arg | Glu | Thr | Gly |      |
| 775 |     |     |     |     | 780 |     |     |     |     | 785 |     |     |     |     | 790 |      |
| AGC | CCT | CCT | TGC | TTT | GAT | GAA | TAC | AAA | ATA | TCA | AAG | GAA | TGG | GCA | GCC | 2574 |
| Ser | Pro | Pro | Cys | Phe | Asp | Glu | Tyr | Lys | Ile | Ser | Lys | Glu | Trp | Ala | Ala |      |
|     |     |     |     | 795 |     |     |     |     | 800 |     |     |     |     | 805 |     |      |
| AGT | TCT | ACT | TTC | AGC | AGT | GTG | TGC | AAC | CAA | CAG | CCA | TTG | GAT | TTA | TCC | 2622 |
| Ser | Ser | Thr | Phe | Ser | Ser | Val | Cys | Asn | Gln | Gln | Pro | Leu | Asp | Leu | Ser |      |
|     |     |     | 810 |     |     |     |     | 815 |     |     |     |     | 820 |     |     |      |
| AGC | GGG | GTC | AAA | CAG | AAG | TCA | GAG | GGC | ACA | GGC | AAG | ACT | CCA | GTC | CCA | 2670 |
| Ser | Gly | Val | Lys | Gln | Lys | Ser | Glu | Gly | Thr | Gly | Lys | Thr | Pro | Val | Pro |      |
|     |     | 825 |     |     |     |     | 830 |     |     |     |     | 835 |     |     |     |      |
| TGG | GAA | TCT | GTA | TTG | GAT | CTC | AGT | GTG | CAT | AAA | AAG | CCT | TGC | GAT | TCT | 2718 |
| Trp | Glu | Ser | Val | Leu | Asp | Leu | Ser | Val | His | Lys | Lys | Pro | Cys | Asp | Ser |      |

```
                840                           845                           850
GAA  GGC  AAG  GAA  TTC  AAA  GAG  AAC  CAT  TTG  GCA  CAG  CCA  GCT  GCA  AAG      2766
Glu  Gly  Lys  Glu  Phe  Lys  Glu  Asn  His  Leu  Ala  Gln  Pro  Ala  Ala  Lys
855                 860                      865                           870

AAG  AAA  AAA  CCA  ACC  ACC  TGT  ATG  CTT  CAA  AAG  GTT  CTT  CTC  AAT  GAG      2814
Lys  Lys  Lys  Pro  Thr  Thr  Cys  Met  Leu  Gln  Lys  Val  Leu  Leu  Asn  Glu
                         875                 880                           885

TAT  AAT  GGT  GTT  AGC  TTA  CCT  ACA  GAA  ACC  ACA  CCA  GAG  GTG  ACC  AGG      2862
Tyr  Asn  Gly  Val  Ser  Leu  Pro  Thr  Glu  Thr  Thr  Pro  Glu  Val  Thr  Arg
               890                      895                      900

AGC  CCA  AGT  CCT  TGT  AAA  TCC  CCA  GAT  ACA  CAG  CCA  GAT  CCT  GAA  CTT      2910
Ser  Pro  Ser  Pro  Cys  Lys  Ser  Pro  Asp  Thr  Gln  Pro  Asp  Pro  Glu  Leu
          905                      910                      915

GGT  CCT  GAC  TCA  AGT  TGC  TCA  GTC  CCC  ACT  GCT  GAG  TCT  CCA  CCT  GAA      2958
Gly  Pro  Asp  Ser  Ser  Cys  Ser  Val  Pro  Thr  Ala  Glu  Ser  Pro  Pro  Glu
     920                      925                      930

GTT  GTT  GGC  CCT  TCC  TCA  CCC  CCT  CTC  CAG  ACA  GCC  TCC  TTA  TCC  TCC      3006
Val  Val  Gly  Pro  Ser  Ser  Pro  Pro  Leu  Gln  Thr  Ala  Ser  Leu  Ser  Ser
935                      940                      945                           950

GGT  CAG  CTG  CCT  CCT  CTC  TTA  ACC  CCC  ACA  GAG  CCT  TCT  TCC  CCT  CCC      3054
Gly  Gln  Leu  Pro  Pro  Leu  Leu  Thr  Pro  Thr  Glu  Pro  Ser  Ser  Pro  Pro
                    955                      960                      965

CCC  TGC  CCT  CCT  GTG  TTA  ACT  GTT  GCC  ACT  CCA  CCA  CCT  CCC  CTC  CTT      3102
Pro  Cys  Pro  Pro  Val  Leu  Thr  Val  Ala  Thr  Pro  Pro  Pro  Pro  Leu  Leu
               970                      975                      980

CCA  ACC  GTC  CCT  CTC  TCC  CAC  CCC  TCT  TCT  GAT  GCC  TCC  CCT  CAG  CAG      3150
Pro  Thr  Val  Pro  Leu  Ser  His  Pro  Ser  Ser  Asp  Ala  Ser  Pro  Gln  Gln
          985                      990                      995

TGT  CCC  TCT  CCG  TTC  TCA  AAC  ACC  ACT  GCT  CAG  TCT  CCT  CTT  CCC  ATT      3198
Cys  Pro  Ser  Pro  Phe  Ser  Asn  Thr  Thr  Ala  Gln  Ser  Pro  Leu  Pro  Ile
     1000                     1005                     1010

CTC  TCC  CCA  ACA  GTG  TCT  CCC  TCT  CCC  TCT  CCC  ATT  CCT  CCT  GTA  GAG      3246
Leu  Ser  Pro  Thr  Val  Ser  Pro  Ser  Pro  Ser  Pro  Ile  Pro  Pro  Val  Glu
1015                     1020                     1025                          1030

CCA  CTT  ATG  TCT  GCT  GCT  TCC  CCT  GGT  CCC  CCA  ACA  CTT  TCT  TCC  TCC      3294
Pro  Leu  Met  Ser  Ala  Ala  Ser  Pro  Gly  Pro  Pro  Thr  Leu  Ser  Ser  Ser
                    1035                     1040                     1045

TCC  TCT  TCT  TCC  TCT  TCC  TTC  CCT  TCC  TCT  TCC  TGC  TCC  TCC  ACC  TCC      3342
Ser  Ser  Ser  Ser  Ser  Ser  Phe  Pro  Ser  Ser  Ser  Cys  Ser  Ser  Thr  Ser
               1050                     1055                     1060

CCC  TCC  CCA  CCC  CCT  CTT  TCA  GCA  GTG  TCA  TCT  GTG  GTT  TCC  TCT  GGG      3390
Pro  Ser  Pro  Pro  Pro  Leu  Ser  Ala  Val  Ser  Ser  Val  Val  Ser  Ser  Gly
          1065                     1070                     1075

GAC  AAC  CTG  GAG  GCA  TCT  CTG  CCT  GCA  GTA  ACT  TTC  AAA  CAG  GAG  GAG      3438
Asp  Asn  Leu  Glu  Ala  Ser  Leu  Pro  Ala  Val  Thr  Phe  Lys  Gln  Glu  Glu
     1080                     1085                     1090

TCA  GAG  AGT  GAA  GGT  CTG  AAA  CCC  AAG  GAA  GAG  GCC  CCA  CCT  GCA  GGG      3486
Ser  Glu  Ser  Glu  Gly  Leu  Lys  Pro  Lys  Glu  Glu  Ala  Pro  Pro  Ala  Gly
1095                     1100                     1105                          1110

GGA  CAG  AGT  GTG  GTC  CAA  GAA  ACA  TTC  AGC  AAA  AAC  TTC  ATT  TGC  AAT      3534
Gly  Gln  Ser  Val  Val  Gln  Glu  Thr  Phe  Ser  Lys  Asn  Phe  Ile  Cys  Asn
                    1115                     1120                     1125

GTC  TGT  GAA  TCG  CCT  TTT  CTT  TCC  ATT  AAA  GAC  CTA  ACC  AAA  CAT  TTA      3582
Val  Cys  Glu  Ser  Pro  Phe  Leu  Ser  Ile  Lys  Asp  Leu  Thr  Lys  His  Leu
               1130                     1135                     1140

TCC  GTC  CAT  GCT  GAA  GAG  TGG  CCC  TTC  AAA  TGT  GAG  TTT  TGT  GTG  CAG      3630
Ser  Val  His  Ala  Glu  Glu  Trp  Pro  Phe  Lys  Cys  Glu  Phe  Cys  Val  Gln
          1145                     1150                     1155

CTG  TTT  AAG  GTT  AAG  ACT  GAT  CTA  TCA  GAG  CAT  CGA  TTT  CTG  CTT  CAT      3678
Leu  Phe  Lys  Val  Lys  Thr  Asp  Leu  Ser  Glu  His  Arg  Phe  Leu  Leu  His
```

```
                        1160                        1165                        1170
GGG  GTT  GGA  AAT  ATC  TTT  GTG  TGT  TCT  GTA  TGT  AAG  AAA  GAA  TTT  GCC       3726
Gly  Val  Gly  Asn  Ile  Phe  Val  Cys  Ser  Val  Cys  Lys  Lys  Glu  Phe  Ala
1175                1180                     1185                          1190

TTC  TTA  TGC  AAT  CTG  CAG  CAG  CAC  CAG  CGT  GAT  CTC  CAC  CCA  GAT  GAG       3774
Phe  Leu  Cys  Asn  Leu  Gln  Gln  His  Gln  Arg  Asp  Leu  His  Pro  Asp  Glu
                         1195                     1200                     1205

GTA  TGC  ACA  CAC  CAC  GAG  TTT  GAA  AGT  GGG  ACC  CTG  AGG  CCC  CAG  AAC       3822
Val  Cys  Thr  His  His  Glu  Phe  Glu  Ser  Gly  Thr  Leu  Arg  Pro  Gln  Asn
               1210                     1215                          1220

TTC  ACA  GAC  CCC  AGC  AAG  GCC  AAT  GTT  GAG  CAT  ATG  CCA  AGT  TTG  CCA       3870
Phe  Thr  Asp  Pro  Ser  Lys  Ala  Asn  Val  Glu  His  Met  Pro  Ser  Leu  Pro
          1225                     1230                     1235

GAA  GAG  CCT  TTA  GAA  ACT  TCT  AGA  GAG  GAG  GAG  TTA  AAT  GAT  TCC  TCT       3918
Glu  Glu  Pro  Leu  Glu  Thr  Ser  Arg  Glu  Glu  Glu  Leu  Asn  Asp  Ser  Ser
1240                     1245                     1250

GAA  GAG  CTT  TAC  ACG  ACC  ATC  AAA  ATA  ATG  GCT  TCT  GGA  ATA  AAG  ACG       3966
Glu  Glu  Leu  Tyr  Thr  Thr  Ile  Lys  Ile  Met  Ala  Ser  Gly  Ile  Lys  Thr
1255                     1260                     1265                          1270

AAG  GAT  CCA  GAT  GTT  CGA  CTT  GGT  CTC  AAC  CAG  CAC  TAC  CCG  AGC  TTT       4014
Lys  Asp  Pro  Asp  Val  Arg  Leu  Gly  Leu  Asn  Gln  His  Tyr  Pro  Ser  Phe
                    1275                     1280                     1285

AAA  CCT  CCT  CCA  TTT  CAG  TAC  CAC  CAT  CGA  AAC  CCT  ATG  GGG  ATA  GGG       4062
Lys  Pro  Pro  Pro  Phe  Gln  Tyr  His  His  Arg  Asn  Pro  Met  Gly  Ile  Gly
                    1290                     1295                     1300

GTG  ACA  GCC  ACC  AAC  TTC  ACC  ACC  CAC  AAT  ATT  CCA  CAG  ACT  TTC  ACT       4110
Val  Thr  Ala  Thr  Asn  Phe  Thr  Thr  His  Asn  Ile  Pro  Gln  Thr  Phe  Thr
               1305                     1310                     1315

ACT  GCC  ATC  CGC  TGC  ACA  AAG  TGT  GGG  AAG  GGC  GTC  GAC  AAT  ATG  CCT       4158
Thr  Ala  Ile  Arg  Cys  Thr  Lys  Cys  Gly  Lys  Gly  Val  Asp  Asn  Met  Pro
          1320                     1325                     1330

GAG  CTG  CAT  AAG  CAT  ATC  TTG  GCG  TGT  GCG  TCT  GCA  AGT  GAC  AAG  AAG       4206
Glu  Leu  His  Lys  His  Ile  Leu  Ala  Cys  Ala  Ser  Ala  Ser  Asp  Lys  Lys
1335                     1340                     1345                          1350

AGG  TAC  ACC  CCT  AAG  AAA  AAC  CCA  GTG  CCC  CTG  AAA  CAA  ACT  GTG  CAG       4254
Arg  Tyr  Thr  Pro  Lys  Lys  Asn  Pro  Val  Pro  Leu  Lys  Gln  Thr  Val  Gln
                    1355                     1360                     1365

CCC  AAA  AAT  GGA  GTG  GTG  GTT  CTA  GAC  AAC  TCT  GGG  AAA  AAT  GCC  TTC       4302
Pro  Lys  Asn  Gly  Val  Val  Val  Leu  Asp  Asn  Ser  Gly  Lys  Asn  Ala  Phe
               1370                     1375                     1380

AGA  CGG  ATG  GGG  CAG  CCC  AAG  AGA  CTG  AGC  TTC  AAT  GTT  GAA  CTG  GGT       4350
Arg  Arg  Met  Gly  Gln  Pro  Lys  Arg  Leu  Ser  Phe  Asn  Val  Glu  Leu  Gly
          1385                     1390                     1395

AAA  ATG  TCT  CCA  AAC  AAG  CTC  AAG  CTG  AGT  GCG  CTG  AAG  AAG  AAA  AAC       4398
Lys  Met  Ser  Pro  Asn  Lys  Leu  Lys  Leu  Ser  Ala  Leu  Lys  Lys  Lys  Asn
1400                     1405                     1410

CAG  CTG  GTG  CAG  AAG  GCC  ATC  CTT  CAG  AAG  AAC  AGA  GCC  GCG  AAG  CAG       4446
Gln  Leu  Val  Gln  Lys  Ala  Ile  Leu  Gln  Lys  Asn  Arg  Ala  Ala  Lys  Gln
1415                     1420                     1425                          1430

AAG  GCG  GAC  CTG  AGG  GAT  ACT  TCC  GAG  GCG  TCC  TCA  CAC  ATC  TGC  CCG       4494
Lys  Ala  Asp  Leu  Arg  Asp  Thr  Ser  Glu  Ala  Ser  Ser  His  Ile  Cys  Pro
                    1435                     1440                     1445

TAC  TGT  GAC  AGG  GAG  TTC  ACA  TAC  ATT  GGC  AGC  CTG  AAT  AAG  CAT  GCC       4542
Tyr  Cys  Asp  Arg  Glu  Phe  Thr  Tyr  Ile  Gly  Ser  Leu  Asn  Lys  His  Ala
               1450                     1455                     1460

GCC  TTC  AGC  TGT  CCT  AAA  AAA  CCT  CTT  TCT  CCT  TCC  AAA  AGA  AAA  GTT       4590
Ala  Phe  Ser  Cys  Pro  Lys  Lys  Pro  Leu  Ser  Pro  Ser  Lys  Arg  Lys  Val
          1465                     1470                     1475

TCC  CAT  TCG  TCT  AAG  AAA  GGT  GGC  CAT  GCA  TCA  TCT  TCT  AGC  AGT  GAC       4638
Ser  His  Ser  Ser  Lys  Lys  Gly  Gly  His  Ala  Ser  Ser  Ser  Ser  Ser  Asp
```

-continued

|  | 1480 | | | | 1485 | | | | | 1490 | | | | | | |
|---|---|---|---|---|---|---|---|---|---|---|---|---|---|---|---|---|
| AGA | AAC | AGC | AGC | TGC | CAC | CCC | CGG | AGG | CGG | ACT | GCA | GAT | ACC | GAG | ATC | 4686 |
| Arg | Asn | Ser | Ser | Cys | His | Pro | Arg | Arg | Arg | Thr | Ala | Asp | Thr | Glu | Ile | |
| 1495 | | | | 1500 | | | | | 1505 | | | | | 1510 | | |
| AAG | ATG | CAG | AGC | ACG | CAG | GCA | CCC | TTG | GGC | AAG | ACC | AGA | GCT | CGG | AGT | 4734 |
| Lys | Met | Gln | Ser | Thr | Gln | Ala | Pro | Leu | Gly | Lys | Thr | Arg | Ala | Arg | Ser | |
| | | | | 1515 | | | | | 1520 | | | | | 1525 | | |
| ACA | GGC | CCC | GCC | CAG | GCC | TCA | CTG | CCC | TCC | TCG | TCC | TTC | AGA | TCC | AGA | 4782 |
| Thr | Gly | Pro | Ala | Gln | Ala | Ser | Leu | Pro | Ser | Ser | Ser | Phe | Arg | Ser | Arg | |
| | | | 1530 | | | | | 1535 | | | | | 1540 | | | |
| CAG | AAT | GTC | AAA | TTT | GCA | GCT | TCA | GTG | AAA | TCC | AAA | AAA | GCA | AGC | TCT | 4830 |
| Gln | Asn | Val | Lys | Phe | Ala | Ala | Ser | Val | Lys | Ser | Lys | Lys | Ala | Ser | Ser | |
| | | 1545 | | | | | 1550 | | | | | 1555 | | | | |
| TCA | TCC | TTG | AGG | AAT | TCC | AGT | CCC | ATA | AGA | ATG | GCC | AAA | ATT | ACT | CAC | 4878 |
| Ser | Ser | Leu | Arg | Asn | Ser | Ser | Pro | Ile | Arg | Met | Ala | Lys | Ile | Thr | His | |
| | 1560 | | | | | 1565 | | | | | 1570 | | | | | |
| GTC | GAG | GGC | AAA | AAA | CCC | AAA | GCT | GTT | GCC | AAG | AGT | CAT | TCT | GCT | CAG | 4926 |
| Val | Glu | Gly | Lys | Lys | Pro | Lys | Ala | Val | Ala | Lys | Ser | His | Ser | Ala | Gln | |
| 1575 | | | | 1580 | | | | | 1585 | | | | | 1590 | | |
| CTC | TCA | AGC | AAA | TCC | TCC | CGA | GGC | CTG | CAT | GTC | AGA | GTG | CAG | AAG | AGC | 4974 |
| Leu | Ser | Ser | Lys | Ser | Ser | Arg | Gly | Leu | His | Val | Arg | Val | Gln | Lys | Ser | |
| | | | | 1595 | | | | | 1600 | | | | | 1605 | | |
| AAA | GCT | GTC | ATA | CAG | AGC | AAG | ACT | GCC | CTG | GCC | AGT | AAG | AGG | AGA | ACA | 5022 |
| Lys | Ala | Val | Ile | Gln | Ser | Lys | Thr | Ala | Leu | Ala | Ser | Lys | Arg | Arg | Thr | |
| | | | 1610 | | | | | 1615 | | | | | 1620 | | | |
| GAC | CGG | TTC | ATA | GTG | AAA | TCT | AGA | GAG | CGC | AGC | GGG | GGC | CCA | ATC | ACC | 5070 |
| Asp | Arg | Phe | Ile | Val | Lys | Ser | Arg | Glu | Arg | Ser | Gly | Gly | Pro | Ile | Thr | |
| | | 1625 | | | | | 1630 | | | | | 1635 | | | | |
| CGA | AGC | CTT | CAG | CTG | GCA | GCT | GCT | GCG | GAC | CTG | AGT | GAA | AGC | AGG | AGA | 5118 |
| Arg | Ser | Leu | Gln | Leu | Ala | Ala | Ala | Ala | Asp | Leu | Ser | Glu | Ser | Arg | Arg | |
| | 1640 | | | | | 1645 | | | | | 1650 | | | | | |
| GAG | GAC | AGC | AGT | GCC | AGG | CAT | GAG | CTG | AAG | GAC | TTC | AGC | TAC | AGT | CTC | 5166 |
| Glu | Asp | Ser | Ser | Ala | Arg | His | Glu | Leu | Lys | Asp | Phe | Ser | Tyr | Ser | Leu | |
| 1655 | | | | 1660 | | | | | 1665 | | | | | 1670 | | |
| CGC | CTG | GCA | TCT | CGA | TGC | GGC | TCA | TCA | ACA | GCC | TCT | TAC | ATC | ACC | AGA | 5214 |
| Arg | Leu | Ala | Ser | Arg | Cys | Gly | Ser | Ser | Thr | Ala | Ser | Tyr | Ile | Thr | Arg | |
| | | | | 1675 | | | | | 1680 | | | | | 1685 | | |
| CAA | TGC | AGA | AAG | GTC | AAG | GCC | GCC | GCA | GCA | ACT | CCG | TTC | CAG | GGA | CCC | 5262 |
| Gln | Cys | Arg | Lys | Val | Lys | Ala | Ala | Ala | Ala | Thr | Pro | Phe | Gln | Gly | Pro | |
| | | | 1690 | | | | | 1695 | | | | | 1700 | | | |
| TTC | CTC | AAA | GAG | T | AGGCACTCTG | TCTGCTCCTT | AACAGCACCT | GAAGTGACCT | | | | | | | | 5315 |
| Phe | Leu | Lys | Glu | | | | | | | | | | | | | |
| | | 1705 | | | | | | | | | | | | | | |

```
GGAATCAGTG  AAGCCAAAGG  GACCAGCAGT  CTGCCCTGCA  GAGAGCACTG  ACCTCTCCCA    5375
GTTGTGAGAG  TGAGAGAACG  AGAGAGAGAG  AGAGAGAGAG  AGAGAGAGAG  AGAGAGAGAG    5435
AGAATGAGAA  TGTGTGTGTG  TGTGTGCTGG  TGCATGTGTG  TGGTCTTCAA  GCCAAGGTCC    5495
CAGCCTCAGG  AGCAGGACCT  TCCCATTTCC  CGTCATCCTC  TGGATGATCC  TTGGACGTGG    5555
CCCAGAACCG  TGCTCTGTGG  TGCAGCCATC  CTGCCCGGGA  GGGGCATCTC  CTTCTATGCA    5615
ATTTTTTTAA  AGAGTTCCTT  GGCCCTGCTT  TGTGCTTCTT  GAGCTGTCCG  TTTGCCACCA    5675
CTGGGACTTG  GATCTGGCCC  TGAGGGGTGG  GGAAGAGGGC  CTATCTAAGG  ATAACCTTTC    5735
AGAGGTCAAG  CTCCCCTTCA  TGCCACCCCT  CCCCCCTGCC  CTCACCGACC  TTTTCCCCAC    5795
ACTGTCTCTG  GGAATCAATA  GCAGATAGCA  TATAGATCCA  TCAGGGTTGA  GCCTGAACCT    5855
CGGCCCTAGC  ACTAGGAAAT  CCCCCTTTTC  TCCCTAAGCA  ACTGGAGCCG  CCAGCTTTCA    5915
AGTCATTTCC  TCCTTTGAGG  TTCTAGAGTC  CGAGAGTCTG  CTCCGAAGTC  TCTCCTGGGA    5975
```

```
ACCCGGGAGC CCTCGCACCC AGGACGCAGA CTCTGTGCCC ATTCTTAGAC CTGAGGTAGA    6035

AGAAGCAGTG TTTTGGGACG ATAGGGTGGA GGCGTGCCTA CTTTGTCTCC TCTGGTGGGA    6095

CCTCCTACAT CATTGGCATC TGAACCTTGC AAGTTCGCTG CAAAGAGAAG CAAAGGAAAA    6155

AAAAAAAAAA AAAAA                                                    6171
```

( 2 ) INFORMATION FOR SEQ ID NO:2:

( i ) SEQUENCE CHARACTERISTICS:
        ( A ) LENGTH: 1706 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met His Gln Asn Thr Glu Ser Val Ala Ala Thr Glu Thr Leu Ala Glu
 1               5                  10                  15

Val Pro Glu His Val Leu Arg Gly Leu Pro Glu Glu Val Arg Leu Phe
                20                  25                  30

Pro Ser Ala Val Asp Lys Thr Arg Ile Gly Val Trp Ala Thr Lys Pro
            35                  40                  45

Ile Leu Lys Gly Lys Lys Phe Gly Pro Phe Val Gly Asp Lys Lys Lys
        50                  55                  60

Arg Ser Gln Val Arg Asn Asn Val Tyr Met Trp Glu Val Tyr Tyr Pro
65                  70                  75                  80

Asn Leu Gly Trp Met Cys Ile Asp Ala Thr Asp Pro Glu Lys Gly Asn
                85                  90                  95

Trp Leu Arg Tyr Val Asn Trp Ala Cys Ser Gly Glu Glu Gln Asn Leu
                100                 105                 110

Phe Pro Leu Glu Ile Asn Arg Ala Ile Tyr Tyr Lys Thr Leu Lys Pro
            115                 120                 125

Ile Ala Pro Gly Glu Glu Leu Leu Val Trp Tyr Asn Gly Glu Asp Asn
        130                 135                 140

Pro Glu Ile Ala Ala Ala Ile Glu Glu Glu Arg Ala Ser Ala Arg Ser
145                 150                 155                 160

Lys Arg Ser Ser Pro Lys Ser Arg Arg Gly Lys Lys Ser His Glu
                165                 170                 175

Asn Lys Asn Lys Gly Ile Arg Thr His Pro Thr Gln Leu Lys Ala Ser
                180                 185                 190

Glu Leu Asp Ser Thr Phe Ala Asn Met Arg Gly Ser Glu Gly Pro
            195                 200                 205

Lys Glu Glu Asp Glu Arg Pro Leu Ala Ser Ala Pro Glu Gln Pro Ala
210                 215                 220

Pro Leu Pro Glu Val Gly Asn Gln Asp Ala Val Pro Gln Val Ala Ile
225                 230                 235                 240

Pro Leu Pro Ala Cys Glu Pro Gln Pro Glu Val Asp Gly Lys Gln Glu
            245                 250                 255

Val Thr Asp Cys Glu Val Asn Asp Val Glu Glu Glu Leu Glu Glu
            260                 265                 270

Glu Glu Glu Leu Glu Glu Glu Glu Glu Glu Glu Leu Gly Glu Asp Gly
                275                 280                 285

Val Glu Glu Ala Asp Met Pro Asn Glu Ser Ser Ala Lys Glu Pro Glu
            290                 295                 300

Ile Arg Cys Glu Glu Lys Pro Glu Asp Leu Leu Glu Glu Pro Gln Ser
305                 310                 315                 320
```

```
Met Ser Asn Glu Ala Arg Glu Asp Ser Pro Asp Val Thr Pro Pro
            325                 330                 335

His Thr Pro Arg Ala Arg Glu Glu Ala Asn Gly Asp Val Leu Glu Thr
            340                 345                 350

Phe Met Phe Pro Cys Gln His Cys Glu Arg Lys Phe Ala Thr Lys Gln
            355                 360                 365

Gly Leu Glu Arg His Met His Ile His Ile Ser Thr Ile Asn His Ala
370                 375                 380

Phe Lys Cys Lys Tyr Cys Gly Lys Arg Phe Gly Thr Gln Ile Asn Arg
385                 390                 395                 400

Arg Arg His Glu Arg Arg His Glu Thr Gly Leu Lys Arg Arg Pro Ser
                405                 410                 415

Met Thr Leu Gln Ser Ser Glu Asp Pro Asp Asp Gly Lys Gly Glu Asn
            420                 425                 430

Val Thr Ser Lys Asp Glu Ser Ser Pro Pro Gln Leu Gly Gln Asp Cys
            435                 440                 445

Leu Ile Leu Asn Ser Glu Lys Thr Ser Gln Glu Val Leu Asn Ser Ser
    450                 455                 460

Phe Val Glu Glu Asn Gly Glu Val Lys Glu Leu His Pro Cys Lys Tyr
465                 470                 475                 480

Cys Lys Lys Val Phe Gly Thr His Thr Asn Met Arg Arg His Gln Arg
                485                 490                 495

Arg Val His Glu Arg His Leu Ile Pro Lys Gly Val Arg Arg Lys Gly
            500                 505                 510

Gly Leu Leu Glu Glu Pro Gln Pro Pro Ala Glu Gln Ala Pro Pro Ser
            515                 520                 525

Gln Asn Val Tyr Val Pro Ser Thr Glu Pro Glu Glu Gly Glu Thr
    530                 535                 540

Asp Asp Val Tyr Ile Met Asp Ile Ser Ser Asn Ile Ser Glu Asn Leu
545                 550                 555                 560

Asn Tyr Tyr Ile Asp Gly Lys Ile Gln Thr Asn Ser Ser Thr Ser Asn
                565                 570                 575

Cys Asp Val Ile Glu Met Glu Ser Asn Ser Ala His Leu Tyr Gly Ile
            580                 585                 590

Asp Cys Leu Leu Thr Pro Val Thr Val Glu Ile Thr Gln Asn Ile Lys
    595                 600                 605

Ser Thr Gln Val Ser Val Thr Asp Asp Leu Leu Lys Asp Ser Pro Ser
    610                 615                 620

Ser Thr Asn Cys Glu Ser Lys Lys Arg Arg Thr Ala Ser Pro Pro Val
625                 630                 635                 640

Leu Pro Lys Ile Lys Thr Glu Thr Glu Ser Asp Ser Thr Ala Pro Ser
                645                 650                 655

Cys Ser Leu Ser Leu Pro Leu Ser Ile Ser Thr Ala Glu Val Val Ser
            660                 665                 670

Phe His Lys Glu Lys Gly Val Tyr Leu Ser Ser Lys Leu Lys Gln Leu
    675                 680                 685

Leu Gln Thr Gln Asp Lys Leu Thr Leu Pro Ala Gly Phe Ser Ala Ala
    690                 695                 700

Glu Ile Pro Lys Leu Gly Pro Val Cys Ala Ser Ala Pro Ala Ser Met
705                 710                 715                 720

Leu Pro Val Thr Ser Ser Arg Phe Lys Arg Arg Thr Ser Ser Pro Pro
                725                 730                 735

Ser Ser Pro Gln His Ser Pro Ala Leu Arg Asp Phe Gly Lys Pro Asn
            740                 745                 750
```

| | | | | | | | | | | | | | | |
|---|---|---|---|---|---|---|---|---|---|---|---|---|---|---|
| Asp | Gly | Lys<br>755 | Ala | Ala | Trp | Thr | Asp<br>760 | Thr | Val | Leu | Thr | Ser<br>765 | Lys | Lys | Pro |
| Lys | Leu | Glu<br>770 | Ser | Arg | Ser | Asp | Ser<br>775 | Pro | Ala | Trp | Ser<br>780 | Leu | Ser | Gly | Arg |
| Asp<br>785 | Glu | Arg | Glu | Thr | Gly<br>790 | Ser | Pro | Pro | Cys | Phe<br>795 | Asp | Glu | Tyr | Lys | Ile<br>800 |
| Ser | Lys | Glu | Trp | Ala<br>805 | Ala | Ser | Ser | Thr | Phe<br>810 | Ser | Ser | Val | Cys | Asn<br>815 | Gln |
| Gln | Pro | Leu | Asp<br>820 | Leu | Ser | Ser | Gly | Val<br>825 | Lys | Gln | Lys | Ser | Glu<br>830 | Gly | Thr |
| Gly | Lys | Thr<br>835 | Pro | Val | Pro | Trp | Glu<br>840 | Ser | Val | Leu | Asp | Leu<br>845 | Ser | Val | His |
| Lys | Lys<br>850 | Pro | Cys | Asp | Ser | Glu<br>855 | Gly | Lys | Glu | Phe | Lys<br>860 | Glu | Asn | His | Leu |
| Ala<br>865 | Gln | Pro | Ala | Ala | Lys<br>870 | Lys | Lys | Pro | Thr | Thr<br>875 | Cys | Met | Leu | Gln<br>880 |
| Lys | Val | Leu | Leu | Asn<br>885 | Glu | Tyr | Asn | Gly<br>890 | Val | Ser | Leu | Pro | Thr<br>895 | Glu | Thr |
| Thr | Pro | Glu | Val<br>900 | Thr | Arg | Ser | Pro<br>905 | Ser | Pro | Cys | Lys | Ser<br>910 | Pro | Asp | Thr |
| Gln | Pro | Asp<br>915 | Pro | Glu | Leu | Gly | Pro<br>920 | Asp | Ser | Ser | Cys | Ser<br>925 | Val | Pro | Thr |
| Ala | Glu | Ser<br>930 | Pro | Pro | Glu | Val<br>935 | Val | Gly | Pro | Ser | Ser<br>940 | Pro | Pro | Leu | Gln |
| Thr<br>945 | Ala | Ser | Leu | Ser | Ser<br>950 | Gly | Gln | Leu | Pro | Leu<br>955 | Leu | Thr | Pro | Thr<br>960 |
| Glu | Pro | Ser | Ser | Pro<br>965 | Pro | Pro | Cys | Pro | Pro<br>970 | Val | Leu | Thr | Val | Ala<br>975 | Thr |
| Pro | Pro | Pro | Pro<br>980 | Leu | Leu | Pro | Thr | Val<br>985 | Pro | Leu | Ser | His | Pro<br>990 | Ser | Ser |
| Asp | Ala | Ser<br>995 | Pro | Gln | Gln | Cys | Pro<br>1000 | Ser | Pro | Phe | Ser | Asn<br>1005 | Thr | Thr | Ala |
| Gln | Ser | Pro<br>1010 | Leu | Pro | Ile | Leu | Ser<br>1015 | Pro | Thr | Val | Ser | Pro<br>1020 | Ser | Pro | Ser |
| Pro<br>1025 | Ile | Pro | Pro | Val | Glu<br>1030 | Pro | Leu | Met | Ser | Ala<br>1035 | Ala | Ser | Pro | Gly | Pro<br>1040 |
| Pro | Thr | Leu | Ser | Ser<br>1045 | Ser | Ser | Ser | Ser | Ser<br>1050 | Ser | Ser | Phe | Pro | Ser<br>1055 | Ser |
| Ser | Cys | Ser | Ser | Thr<br>1060 | Ser | Pro | Ser | Pro<br>1065 | Pro | Pro | Leu | Ser | Ala<br>1070 | Val | Ser |
| Ser | Val | Val<br>1075 | Ser | Ser | Gly | Asp | Asn<br>1080 | Leu | Glu | Ala | Ser | Leu<br>1085 | Pro | Ala | Val |
| Thr | Phe | Lys<br>1090 | Gln | Glu | Glu | Ser | Glu<br>1095 | Ser | Glu | Gly | Leu | Lys<br>1100 | Pro | Lys | Glu |
| Glu | Ala<br>1105 | Pro | Pro | Ala | Gly | Gly<br>1110 | Gln | Ser | Val | Val | Gln<br>1115 | Glu | Thr | Phe | Ser<br>1120 |
| Lys | Asn | Phe | Ile | Cys<br>1125 | Asn | Val | Cys | Glu | Ser<br>1130 | Pro | Phe | Leu | Ser | Ile<br>1135 | Lys |
| Asp | Leu | Thr | Lys | His<br>1140 | Leu | Ser | Val | His<br>1145 | Ala | Glu | Glu | Trp | Pro<br>1150 | Phe | Lys |
| Cys | Glu | Phe | Cys<br>1155 | Val | Gln | Leu | Phe<br>1160 | Lys | Val | Lys | Thr | Asp<br>1165 | Leu | Ser | Glu |
| His | Arg | Phe | Leu | Leu | His | Gly | Val | Gly | Asn | Ile | Phe | Val | Cys | Ser | Val |

-continued

```
          1170                         1175                         1180

Cys  Lys  Lys  Glu  Phe  Ala  Phe  Leu  Cys  Asn  Leu  Gln  Gln  His  Gln  Arg
1185                         1190                         1195                         1200

Asp  Leu  His  Pro  Asp  Glu  Val  Cys  Thr  His  His  Glu  Phe  Glu  Ser  Gly
                    1205                         1210                         1215

Thr  Leu  Arg  Pro  Gln  Asn  Phe  Thr  Asp  Pro  Ser  Lys  Ala  Asn  Val  Glu
               1220                         1225                         1230

His  Met  Pro  Ser  Leu  Pro  Glu  Glu  Pro  Leu  Glu  Thr  Ser  Arg  Glu  Glu
          1235                         1240                         1245

Glu  Leu  Asn  Asp  Ser  Ser  Glu  Glu  Leu  Tyr  Thr  Thr  Ile  Lys  Ile  Met
          1250                         1255                         1260

Ala  Ser  Gly  Ile  Lys  Thr  Lys  Asp  Pro  Asp  Val  Arg  Leu  Gly  Leu  Asn
1265                         1270                         1275                         1280

Gln  His  Tyr  Pro  Ser  Phe  Lys  Pro  Pro  Pro  Phe  Gln  Tyr  His  His  Arg
               1285                         1290                         1295

Asn  Pro  Met  Gly  Ile  Gly  Val  Thr  Ala  Thr  Asn  Phe  Thr  Thr  His  Asn
                    1300                         1305                         1310

Ile  Pro  Gln  Thr  Phe  Thr  Thr  Ala  Ile  Arg  Cys  Thr  Lys  Cys  Gly  Lys
               1315                         1320                         1325

Gly  Val  Asp  Asn  Met  Pro  Glu  Leu  His  Lys  His  Ile  Leu  Ala  Cys  Ala
          1330                         1335                         1340

Ser  Ala  Ser  Asp  Lys  Lys  Arg  Tyr  Thr  Pro  Lys  Lys  Asn  Pro  Val  Pro
1345                         1350                         1355                         1360

Leu  Lys  Gln  Thr  Val  Gln  Pro  Lys  Asn  Gly  Val  Val  Val  Leu  Asp  Asn
                    1365                         1370                         1375

Ser  Gly  Lys  Asn  Ala  Phe  Arg  Arg  Met  Gly  Gln  Pro  Lys  Arg  Leu  Ser
                    1380                         1385                         1390

Phe  Asn  Val  Glu  Leu  Gly  Lys  Met  Ser  Pro  Asn  Lys  Leu  Lys  Leu  Ser
                    1395                         1400                         1405

Ala  Leu  Lys  Lys  Lys  Asn  Gln  Leu  Val  Gln  Lys  Ala  Ile  Leu  Gln  Lys
          1410                         1415                         1420

Asn  Arg  Ala  Ala  Lys  Gln  Lys  Ala  Asp  Leu  Arg  Asp  Thr  Ser  Glu  Ala
1425                         1430                         1435                         1440

Ser  Ser  His  Ile  Cys  Pro  Tyr  Cys  Asp  Arg  Glu  Phe  Thr  Tyr  Ile  Gly
                    1445                         1450                         1455

Ser  Leu  Asn  Lys  His  Ala  Ala  Phe  Ser  Cys  Pro  Lys  Lys  Pro  Leu  Ser
                    1460                         1465                         1470

Pro  Ser  Lys  Arg  Lys  Val  Ser  His  Ser  Ser  Lys  Lys  Gly  Gly  His  Ala
               1475                         1480                         1485

Ser  Ser  Ser  Ser  Ser  Asp  Arg  Asn  Ser  Ser  Cys  His  Pro  Arg  Arg  Arg
1490                         1495                         1500

Thr  Ala  Asp  Thr  Glu  Ile  Lys  Met  Gln  Ser  Thr  Gln  Ala  Pro  Leu  Gly
1505                         1510                         1515                         1520

Lys  Thr  Arg  Ala  Arg  Ser  Thr  Gly  Pro  Ala  Gln  Ala  Ser  Leu  Pro  Ser
                    1525                         1530                         1535

Ser  Ser  Phe  Arg  Ser  Arg  Gln  Asn  Val  Lys  Phe  Ala  Ala  Ser  Val  Lys
                    1540                         1545                         1550

Ser  Lys  Lys  Ala  Ser  Ser  Ser  Leu  Arg  Asn  Ser  Ser  Pro  Ile  Arg
          1555                         1560                         1565

Met  Ala  Lys  Ile  Thr  His  Val  Glu  Gly  Lys  Lys  Pro  Lys  Ala  Val  Ala
          1570                         1575                         1580

Lys  Ser  His  Ser  Ala  Gln  Leu  Ser  Ser  Lys  Ser  Ser  Arg  Gly  Leu  His
1585                         1590                         1595                         1600
```

| Val | Arg | Val | Gln | Lys | Ser | Lys | Ala | Val | Ile | Gln | Ser | Lys | Thr | Ala | Leu |
|-----|-----|-----|-----|-----|-----|-----|-----|-----|-----|-----|-----|-----|-----|-----|-----|
|     |     |     |     | 1605|     |     |     |     | 1610|     |     |     |     | 1615|     |

| Ala | Ser | Lys | Arg | Arg | Thr | Asp | Arg | Phe | Ile | Val | Lys | Ser | Arg | Glu | Arg |
|-----|-----|-----|-----|-----|-----|-----|-----|-----|-----|-----|-----|-----|-----|-----|-----|
|     |     |     |     | 1620|     |     |     |     | 1625|     |     |     |     | 1630|     |

| Ser | Gly | Gly | Pro | Ile | Thr | Arg | Ser | Leu | Gln | Leu | Ala | Ala | Ala | Ala | Asp |
|-----|-----|-----|-----|-----|-----|-----|-----|-----|-----|-----|-----|-----|-----|-----|-----|
|     |     |     |     | 1635|     |     |     |     | 1640|     |     |     |     | 1645|     |

| Leu | Ser | Glu | Ser | Arg | Arg | Glu | Asp | Ser | Ser | Ala | Arg | His | Glu | Leu | Lys |
|-----|-----|-----|-----|-----|-----|-----|-----|-----|-----|-----|-----|-----|-----|-----|-----|
|     |     |     |     | 1650|     |     |     |     | 1655|     |     |     |     | 1660|     |

| Asp | Phe | Ser | Tyr | Ser | Leu | Arg | Leu | Ala | Ser | Arg | Cys | Gly | Ser | Ser | Thr |
|-----|-----|-----|-----|-----|-----|-----|-----|-----|-----|-----|-----|-----|-----|-----|-----|
| 1665|     |     |     |     | 1670|     |     |     |     | 1675|     |     |     |     | 1680|

| Ala | Ser | Tyr | Ile | Thr | Arg | Gln | Cys | Arg | Lys | Val | Lys | Ala | Ala | Ala | Ala |
|-----|-----|-----|-----|-----|-----|-----|-----|-----|-----|-----|-----|-----|-----|-----|-----|
|     |     |     |     | 1685|     |     |     |     | 1690|     |     |     |     | 1695|     |

| Thr | Pro | Phe | Gln | Gly | Pro | Phe | Leu | Lys | Glu |
|-----|-----|-----|-----|-----|-----|-----|-----|-----|-----|
|     |     |     |     | 1700|     |     |     |     | 1705|

( 2 ) INFORMATION FOR SEQ ID NO:3:

( i ) SEQUENCE CHARACTERISTICS:
        ( A ) LENGTH: 5183 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..5158

( x i ) SEQUENCE DESCRIPTION: SEQ ID NO:3:

| ATG | AAT | CAG | AAC | ACT | ACT | GAG | CCT | GTG | GCG | GCC | ACC | GAG | ACC | CTG | GCT | 48 |
|-----|-----|-----|-----|-----|-----|-----|-----|-----|-----|-----|-----|-----|-----|-----|-----|-----|
| Met | Asn | Gln | Asn | Thr | Thr | Glu | Pro | Val | Ala | Ala | Thr | Glu | Thr | Leu | Ala |  |
| 1   |     |     |     | 5   |     |     |     |     | 10  |     |     |     |     | 15  |     |  |

| GAG | GTA | CCC | GAA | CAT | GTG | CTG | CGA | GGA | CTT | CCG | GAG | GAA | GTG | AGG | CTT | 96 |
|-----|-----|-----|-----|-----|-----|-----|-----|-----|-----|-----|-----|-----|-----|-----|-----|-----|
| Glu | Val | Pro | Glu | His | Val | Leu | Arg | Gly | Leu | Pro | Glu | Glu | Val | Arg | Leu |  |
|     |     |     | 20  |     |     |     |     | 25  |     |     |     |     | 30  |     |     |  |

| TTC | CCT | TCT | GCT | GTT | GAC | AAG | ACC | CGG | ATT | GGT | GTC | TGG | GCC | ACT | AAA | 144 |
|-----|-----|-----|-----|-----|-----|-----|-----|-----|-----|-----|-----|-----|-----|-----|-----|-----|
| Phe | Pro | Ser | Ala | Val | Asp | Lys | Thr | Arg | Ile | Gly | Val | Trp | Ala | Thr | Lys |  |
|     |     |     | 35  |     |     |     |     | 40  |     |     |     |     | 45  |     |     |  |

| CCA | ATT | TTA | AAA | GGG | AAA | AAA | TTT | GGG | CCA | TTT | GTT | GGT | GAT | AAG | AAA | 192 |
|-----|-----|-----|-----|-----|-----|-----|-----|-----|-----|-----|-----|-----|-----|-----|-----|-----|
| Pro | Ile | Leu | Lys | Gly | Lys | Lys | Phe | Gly | Pro | Phe | Val | Gly | Asp | Lys | Lys |  |
|     |     | 50  |     |     |     |     | 55  |     |     |     |     | 60  |     |     |     |  |

| AAA | AGA | TCT | CAG | GTT | AAG | AAT | AAT | GTA | TAC | ATG | TGG | GAG | GTG | TAT | TAC | 240 |
|-----|-----|-----|-----|-----|-----|-----|-----|-----|-----|-----|-----|-----|-----|-----|-----|-----|
| Lys | Arg | Ser | Gln | Val | Lys | Asn | Asn | Val | Tyr | Met | Trp | Glu | Val | Tyr | Tyr |  |
| 65  |     |     |     |     | 70  |     |     |     |     | 75  |     |     |     |     | 80  |  |

| CCA | AAT | TTG | GGA | TGG | ATG | TGC | ATT | GAT | GCC | ACT | GAT | CCA | GAG | AAG | GGA | 288 |
|-----|-----|-----|-----|-----|-----|-----|-----|-----|-----|-----|-----|-----|-----|-----|-----|-----|
| Pro | Asn | Leu | Gly | Trp | Met | Cys | Ile | Asp | Ala | Thr | Asp | Pro | Glu | Lys | Gly |  |
|     |     |     |     | 85  |     |     |     |     | 90  |     |     |     |     | 95  |     |  |

| AAC | TGG | CTG | CGA | TAT | GTG | AAT | TGG | GCT | TGC | TCA | GGA | GAA | GAG | CAA | AAT | 336 |
|-----|-----|-----|-----|-----|-----|-----|-----|-----|-----|-----|-----|-----|-----|-----|-----|-----|
| Asn | Trp | Leu | Arg | Tyr | Val | Asn | Trp | Ala | Cys | Ser | Gly | Glu | Glu | Gln | Asn |  |
|     |     |     | 100 |     |     |     |     | 105 |     |     |     |     | 110 |     |     |  |

| TTA | TTC | CCA | CTG | GAA | ATC | AAC | AGA | GCC | ATT | TAC | TAT | AAA | ACT | TTA | AAG | 384 |
|-----|-----|-----|-----|-----|-----|-----|-----|-----|-----|-----|-----|-----|-----|-----|-----|-----|
| Leu | Phe | Pro | Leu | Glu | Ile | Asn | Arg | Ala | Ile | Tyr | Tyr | Lys | Thr | Leu | Lys |  |
|     |     |     | 115 |     |     |     |     | 120 |     |     |     |     | 125 |     |     |  |

| CCA | ATC | GCG | CCG | GGC | GAG | GAG | CTC | CTG | GTC | TGG | TAC | AAT | GGG | GAA | GAC | 432 |
|-----|-----|-----|-----|-----|-----|-----|-----|-----|-----|-----|-----|-----|-----|-----|-----|-----|
| Pro | Ile | Ala | Pro | Gly | Glu | Glu | Leu | Leu | Val | Trp | Tyr | Asn | Gly | Glu | Asp |  |
|     |     |     | 130 |     |     |     |     | 135 |     |     |     |     | 140 |     |     |  |

| AAC | CCT | GAG | ATA | GCA | GCT | GCG | ATT | GAG | GAA | GAG | CGA | GCC | AGC | GCC | CGG | 480 |
|-----|-----|-----|-----|-----|-----|-----|-----|-----|-----|-----|-----|-----|-----|-----|-----|-----|
| Asn | Pro | Glu | Ile | Ala | Ala | Ala | Ile | Glu | Glu | Glu | Arg | Ala | Ser | Ala | Arg |  |
| 145 |     |     |     |     | 150 |     |     |     |     | 155 |     |     |     |     | 160 |  |

| AGC | AAG | CGG | AGC | TCC | CCC | AAG | AGC | CGG | AAA | GGG | AAG | AAA | AAA | TCC | CAG | 528 |
|-----|-----|-----|-----|-----|-----|-----|-----|-----|-----|-----|-----|-----|-----|-----|-----|-----|
| Ser | Lys | Arg | Ser | Ser | Pro | Lys | Ser | Arg | Lys | Gly | Lys | Lys | Lys | Ser | Gln |  |
|     |     |     |     | 165 |     |     |     |     | 170 |     |     |     |     | 175 |     |  |

| | | | | | | | | | | | | | | | | |
|---|---|---|---|---|---|---|---|---|---|---|---|---|---|---|---|---|
| GAA | AAT | AAA | AAC | AAA | GGA | AAC | AAA | ATC | CAA | GAC | ATA | CAA | CTG | AAG | ACA | 576 |
| Glu | Asn | Lys | Asn | Lys | Gly | Asn | Lys | Ile | Gln | Asp | Ile | Gln | Leu | Lys | Thr | |
| | | | 180 | | | | 185 | | | | | 190 | | | | |
| AGT | GAG | CCA | GAT | TTC | ACC | TCT | GCA | AAT | ATG | AGA | GAT | TCT | GCA | GAA | GGT | 624 |
| Ser | Glu | Pro | Asp | Phe | Thr | Ser | Ala | Asn | Met | Arg | Asp | Ser | Ala | Glu | Gly | |
| | | 195 | | | | | 200 | | | | | 205 | | | | |
| CCT | AAA | GAA | GAC | GAA | GAG | AAG | CCT | TCA | GCC | TCA | GCA | CTT | GAG | CAG | CCG | 672 |
| Pro | Lys | Glu | Asp | Glu | Glu | Lys | Pro | Ser | Ala | Ser | Ala | Leu | Glu | Gln | Pro | |
| | 210 | | | | | 215 | | | | | 220 | | | | | |
| GCC | ACC | CTC | CAG | GAG | GTG | GCC | AGT | CAG | GAG | GTG | CCT | CCA | GAA | CTA | GCA | 720 |
| Ala | Thr | Leu | Gln | Glu | Val | Ala | Ser | Gln | Glu | Val | Pro | Pro | Glu | Leu | Ala | |
| 225 | | | | | 230 | | | | | 235 | | | | | 240 | |
| ACC | CCT | GCC | CCT | GCC | TGG | GAG | CCA | CAG | CCA | GAA | CCA | GAC | GAG | CGA | TTA | 768 |
| Thr | Pro | Ala | Pro | Ala | Trp | Glu | Pro | Gln | Pro | Glu | Pro | Asp | Glu | Arg | Leu | |
| | | | | 245 | | | | 250 | | | | | 255 | | | |
| GAA | GCG | GCA | GCT | TGT | GAG | GTG | AAT | GAT | TTG | GGG | GAA | GAG | GAG | GAG | GAG | 816 |
| Glu | Ala | Ala | Ala | Cys | Glu | Val | Asn | Asp | Leu | Gly | Glu | Glu | Glu | Glu | Glu | |
| | | | 260 | | | | | 265 | | | | | 270 | | | |
| GAA | GAG | GAG | GAG | GAT | GAA | GAA | GAA | GAA | GAA | GAT | GAT | GAT | GAT | GAT | GAG | 864 |
| Glu | Glu | Glu | Glu | Asp | Glu | Glu | Glu | Glu | Glu | Asp | Asp | Asp | Asp | Asp | Glu | |
| | | 275 | | | | | 280 | | | | | 285 | | | | |
| TTG | GAA | GAC | GAG | GGG | GAA | GAA | GAA | GCC | AGC | ATG | CCA | AAT | GAA | AAT | TCT | 912 |
| Leu | Glu | Asp | Glu | Gly | Glu | Glu | Glu | Ala | Ser | Met | Pro | Asn | Glu | Asn | Ser | |
| | 290 | | | | | 295 | | | | | 300 | | | | | |
| GTG | AAA | GAG | CCA | GAA | ATA | CGG | TGT | GAT | GAG | AAG | CCA | GAA | GAT | TTA | TTA | 960 |
| Val | Lys | Glu | Pro | Glu | Ile | Arg | Cys | Asp | Glu | Lys | Pro | Glu | Asp | Leu | Leu | |
| 305 | | | | | 310 | | | | | 315 | | | | | 320 | |
| GAG | GAA | CCA | AAA | ACA | ACT | TCA | GAA | GAA | ACT | CTT | GAA | GAC | TGC | TCA | GAG | 1008 |
| Glu | Glu | Pro | Lys | Thr | Thr | Ser | Glu | Glu | Thr | Leu | Glu | Asp | Cys | Ser | Glu | |
| | | | | 325 | | | | | 330 | | | | | 335 | | |
| GTA | ACA | CCT | GCC | ATG | CAA | ATC | CCC | AGA | ACT | AAA | GAA | GAG | GCC | AAT | GGT | 1056 |
| Val | Thr | Pro | Ala | Met | Gln | Ile | Pro | Arg | Thr | Lys | Glu | Glu | Ala | Asn | Gly | |
| | | | 340 | | | | | 345 | | | | | 350 | | | |
| GAT | GTA | TTT | GAA | ACG | TTT | ATG | TTT | CCG | TGT | CAA | CAT | TGT | GAA | AGG | AAG | 1104 |
| Asp | Val | Phe | Glu | Thr | Phe | Met | Phe | Pro | Cys | Gln | His | Cys | Glu | Arg | Lys | |
| | | 355 | | | | | 360 | | | | | 365 | | | | |
| TTT | ACA | ACC | AAA | CAG | GGG | CTT | GAG | CGT | CAC | ATG | CAT | ATC | CAT | ATA | TCC | 1152 |
| Phe | Thr | Thr | Lys | Gln | Gly | Leu | Glu | Arg | His | Met | His | Ile | His | Ile | Ser | |
| | 370 | | | | | 375 | | | | | 380 | | | | | |
| ACC | GTC | AAT | CAT | GCT | TTC | AAA | TGC | AAG | TAC | TGT | GGG | AAA | GCC | TTT | GGC | 1200 |
| Thr | Val | Asn | His | Ala | Phe | Lys | Cys | Lys | Tyr | Cys | Gly | Lys | Ala | Phe | Gly | |
| 385 | | | | | 390 | | | | | 395 | | | | | 400 | |
| ACA | CAG | ATT | AAC | CGG | CGG | CGA | CAT | GAG | CGG | CGC | CAT | GAA | GCA | GGG | TTA | 1248 |
| Thr | Gln | Ile | Asn | Arg | Arg | Arg | His | Glu | Arg | Arg | His | Glu | Ala | Gly | Leu | |
| | | | | 405 | | | | | 410 | | | | | 415 | | |
| AAG | CGG | AAA | CCC | AGC | CAA | ACA | CTA | CAG | CCG | TCA | GAG | GAT | CTG | GCT | GAT | 1296 |
| Lys | Arg | Lys | Pro | Ser | Gln | Thr | Leu | Gln | Pro | Ser | Glu | Asp | Leu | Ala | Asp | |
| | | | 420 | | | | | 425 | | | | | 430 | | | |
| GGC | AAA | GCA | TCT | GGA | GAA | AAC | GTT | GCT | TCA | AAA | GAT | GAT | TCG | AGT | CCT | 1344 |
| Gly | Lys | Ala | Ser | Gly | Glu | Asn | Val | Ala | Ser | Lys | Asp | Asp | Ser | Ser | Pro | |
| | | 435 | | | | | 440 | | | | | 445 | | | | |
| CCC | AGT | CTT | GGG | CCA | GAC | TGT | CTG | ATC | ATG | AAT | TCA | GAG | AAG | GCT | TCC | 1392 |
| Pro | Ser | Leu | Gly | Pro | Asp | Cys | Leu | Ile | Met | Asn | Ser | Glu | Lys | Ala | Ser | |
| | 450 | | | | | 455 | | | | | 460 | | | | | |
| CAA | GAC | ACA | ATA | AAT | TCT | TCT | GTC | GTA | GAA | GAG | AAT | GGG | GAA | GTT | AAA | 1440 |
| Gln | Asp | Thr | Ile | Asn | Ser | Ser | Val | Val | Glu | Glu | Asn | Gly | Glu | Val | Lys | |
| 465 | | | | | 470 | | | | | 475 | | | | | 480 | |
| GAA | CTT | CAT | CCG | TGC | AAA | TAT | TGT | AAA | AAG | GTT | TTT | GGA | ACT | CAT | ACT | 1488 |
| Glu | Leu | His | Pro | Cys | Lys | Tyr | Cys | Lys | Lys | Val | Phe | Gly | Thr | His | Thr | |
| | | | | 485 | | | | | 490 | | | | | 495 | | |

| | | | | | | | | | | | | | | | | |
|---|---|---|---|---|---|---|---|---|---|---|---|---|---|---|---|---|
| AAT | ATG | AGA | CGG | CAT | CAG | CGT | AGA | GTT | CAC | GAA | CGT | CAT | CTG | ATT | CCC | 1536 |
| Asn | Met | Arg | Arg | His | Gln | Arg | Arg | Val | His | Glu | Arg | His | Leu | Ile | Pro | |
| | | | 500 | | | | 505 | | | | | 510 | | | | |
| AAA | GGT | GTA | CGG | CGA | AAA | GGA | GGC | CTT | GAA | GAG | CCC | CAG | CCT | CCA | GCA | 1584 |
| Lys | Gly | Val | Arg | Arg | Lys | Gly | Gly | Leu | Glu | Glu | Pro | Gln | Pro | Pro | Ala | |
| | | 515 | | | | 520 | | | | | 525 | | | | | |
| GAA | CAG | GCC | CAG | GCC | ACC | CAG | AAC | GTG | TAT | GTA | CCA | AGC | ACA | GAG | CCG | 1632 |
| Glu | Gln | Ala | Gln | Ala | Thr | Gln | Asn | Val | Tyr | Val | Pro | Ser | Thr | Glu | Pro | |
| 530 | | | | | 535 | | | | | 540 | | | | | | |
| GAG | GAG | GAA | GGG | GAA | GCA | GAT | GAT | GTG | TAC | ATC | ATG | GAC | ATT | TCT | AGC | 1680 |
| Glu | Glu | Glu | Gly | Glu | Ala | Asp | Asp | Val | Tyr | Ile | Met | Asp | Ile | Ser | Ser | |
| 545 | | | | 550 | | | | | 555 | | | | | 560 | | |
| AAT | ATC | TCT | GAA | AAC | TTA | AAT | TAC | TAT | ATT | GAT | GGT | AAA | ATT | CAA | ACT | 1728 |
| Asn | Ile | Ser | Glu | Asn | Leu | Asn | Tyr | Tyr | Ile | Asp | Gly | Lys | Ile | Gln | Thr | |
| | | | | 565 | | | | | 570 | | | | | 575 | | |
| AAT | AAC | AAC | ACT | AGT | AAC | TGT | GAT | GTG | ATT | GAG | ATG | GAG | TCT | GCT | TCG | 1776 |
| Asn | Asn | Asn | Thr | Ser | Asn | Cys | Asp | Val | Ile | Glu | Met | Glu | Ser | Ala | Ser | |
| | | | 580 | | | | | 585 | | | | | 590 | | | |
| GCA | GAT | TTG | TAT | GGT | ATA | AAT | TGT | CTG | CTC | ACT | CCA | GTT | ACA | GTG | GAA | 1824 |
| Ala | Asp | Leu | Tyr | Gly | Ile | Asn | Cys | Leu | Leu | Thr | Pro | Val | Thr | Val | Glu | |
| | | 595 | | | | | 600 | | | | | 605 | | | | |
| ATT | ACT | CAA | AAT | ATA | AAG | ACC | ACA | CAG | GTC | CCT | GTA | ACA | GAA | GAT | CTT | 1872 |
| Ile | Thr | Gln | Asn | Ile | Lys | Thr | Thr | Gln | Val | Pro | Val | Thr | Glu | Asp | Leu | |
| | 610 | | | | | 615 | | | | | 620 | | | | | |
| CCT | AAA | GAG | CCT | TTG | GGC | AGC | ACA | AAT | AGT | GAG | GCC | AAG | AAG | CGG | AGA | 1920 |
| Pro | Lys | Glu | Pro | Leu | Gly | Ser | Thr | Asn | Ser | Glu | Ala | Lys | Lys | Arg | Arg | |
| 625 | | | | | 630 | | | | | 635 | | | | | 640 | |
| ACT | GCG | AGC | CCA | CCT | GCA | CTG | CCC | AAA | ATT | AAG | GCC | GAA | ACA | GAC | TCT | 1968 |
| Thr | Ala | Ser | Pro | Pro | Ala | Leu | Pro | Lys | Ile | Lys | Ala | Glu | Thr | Asp | Ser | |
| | | | | 645 | | | | | 650 | | | | | 655 | | |
| GAC | CCC | ATG | GTC | CCC | TCT | TGC | TCT | TTA | AGT | CTT | CCT | CTT | AGC | ATA | TCA | 2016 |
| Asp | Pro | Met | Val | Pro | Ser | Cys | Ser | Leu | Ser | Leu | Pro | Leu | Ser | Ile | Ser | |
| | | | 660 | | | | | 665 | | | | | 670 | | | |
| ACA | ACA | GAG | GCA | GTG | TCT | TTC | CAC | AAA | GAG | AAA | AGT | GTT | TAT | TTG | TCA | 2064 |
| Thr | Thr | Glu | Ala | Val | Ser | Phe | His | Lys | Glu | Lys | Ser | Val | Tyr | Leu | Ser | |
| | | | 675 | | | | | 680 | | | | | 685 | | | |
| TCA | AAG | CTC | AAA | CAA | CTT | CTT | CAA | ACC | CAA | GAT | AAA | CTA | ACT | CCT | CCT | 2112 |
| Ser | Lys | Leu | Lys | Gln | Leu | Leu | Gln | Thr | Gln | Asp | Lys | Leu | Thr | Pro | Pro | |
| | 690 | | | | | 695 | | | | | 700 | | | | | |
| GCA | GGG | ATT | TCA | GCA | ACT | GAA | ATA | GCT | AAA | TTA | GGT | CCT | GTT | TGT | GTG | 2160 |
| Ala | Gly | Ile | Ser | Ala | Thr | Glu | Ile | Ala | Lys | Leu | Gly | Pro | Val | Cys | Val | |
| 705 | | | | | 710 | | | | | 715 | | | | | 720 | |
| TCT | GCT | CCT | GCA | TCA | ATG | TTG | CCT | GTG | ACC | TCA | AGT | AGG | TTT | AAG | AGG | 2208 |
| Ser | Ala | Pro | Ala | Ser | Met | Leu | Pro | Val | Thr | Ser | Ser | Arg | Phe | Lys | Arg | |
| | | | | 725 | | | | | 730 | | | | | 735 | | |
| CGG | ACC | AGC | TCT | CCT | CCC | AGT | TCT | CCA | CAG | CAC | AGT | CCT | GCC | CTT | CGA | 2256 |
| Arg | Thr | Ser | Ser | Pro | Pro | Ser | Ser | Pro | Gln | His | Ser | Pro | Ala | Leu | Arg | |
| | | | 740 | | | | | 745 | | | | | 750 | | | |
| GAC | TTT | GGA | AAG | CCA | AGT | GAT | GGG | AAA | GCA | GCA | TGG | ACC | GAT | GCC | GGG | 2304 |
| Asp | Phe | Gly | Lys | Pro | Ser | Asp | Gly | Lys | Ala | Ala | Trp | Thr | Asp | Ala | Gly | |
| | | 755 | | | | | 760 | | | | | 765 | | | | |
| CTG | ACT | TCC | AAA | AAA | TCC | AAA | TTA | GAA | AGT | CAC | AGC | GAC | TCA | CCA | GCA | 2352 |
| Leu | Thr | Ser | Lys | Lys | Ser | Lys | Leu | Glu | Ser | His | Ser | Asp | Ser | Pro | Ala | |
| | 770 | | | | | 775 | | | | | 780 | | | | | |
| TGG | AGT | TTG | TCT | GGG | AGA | GAT | GAG | AGA | GAA | ACT | GTG | AGC | CCT | CCA | TGC | 2400 |
| Trp | Ser | Leu | Ser | Gly | Arg | Asp | Glu | Arg | Glu | Thr | Val | Ser | Pro | Pro | Cys | |
| 785 | | | | | 790 | | | | | 795 | | | | | 800 | |
| TTT | GAT | GAA | TAT | AAA | ATG | TCT | AAA | GAG | TGG | ACA | GCT | AGT | TCT | GCT | TTT | 2448 |
| Phe | Asp | Glu | Tyr | Lys | Met | Ser | Lys | Glu | Trp | Thr | Ala | Ser | Ser | Ala | Phe | |
| | | | | 805 | | | | | 810 | | | | | 815 | | |

| | | | | | | | | | | | | | | | | |
|---|---|---|---|---|---|---|---|---|---|---|---|---|---|---|---|---|
| AGC | AGT | GTG | TGC | AAC | CAG | CAG | CCA | CTG | GAT | TTA | TCC | AGC | GGT | GTC | AAA | 2496 |
| Ser | Ser | Val | Cys | Asn | Gln | Gln | Pro | Leu | Asp | Leu | Ser | Ser | Gly | Val | Lys | |
| | | | 820 | | | | 825 | | | | | | 830 | | | |
| CAG | AAG | GCT | GAG | GGT | ACA | GGC | AAG | ACT | CCA | GTC | CAG | TGG | GAA | TCT | GTC | 2544 |
| Gln | Lys | Ala | Glu | Gly | Thr | Gly | Lys | Thr | Pro | Val | Gln | Trp | Glu | Ser | Val | |
| | | | 835 | | | | | 840 | | | | | 845 | | | |
| TTA | GAT | CTC | AGT | GTG | CAT | AAA | AAG | CAT | TGT | AGT | GAC | TCT | GAA | GGC | AAG | 2592 |
| Leu | Asp | Leu | Ser | Val | His | Lys | Lys | His | Cys | Ser | Asp | Ser | Glu | Gly | Lys | |
| | 850 | | | | | 855 | | | | | 860 | | | | | |
| GAA | TTC | AAA | GAA | AGT | CAT | TCA | GTG | CAG | CCT | ACG | TGT | AGT | GCT | GTA | AAG | 2640 |
| Glu | Phe | Lys | Glu | Ser | His | Ser | Val | Gln | Pro | Thr | Cys | Ser | Ala | Val | Lys | |
| 865 | | | | | 870 | | | | | 875 | | | | | 880 | |
| AAA | AGG | AAA | CCA | ACC | ACC | TGC | ATG | CTG | CAG | AAG | GTT | CTT | CTC | AAT | GAA | 2688 |
| Lys | Arg | Lys | Pro | Thr | Thr | Cys | Met | Leu | Gln | Lys | Val | Leu | Leu | Asn | Glu | |
| | | | | 885 | | | | | 890 | | | | | 895 | | |
| TAT | AAT | GGC | ATC | GAT | TTA | CCT | GTA | GAA | AAC | CCT | GCA | GAT | GGG | ACC | AGG | 2736 |
| Tyr | Asn | Gly | Ile | Asp | Leu | Pro | Val | Glu | Asn | Pro | Ala | Asp | Gly | Thr | Arg | |
| | | | 900 | | | | | 905 | | | | | 910 | | | |
| AGC | CCA | AGT | CCT | TGT | AAA | TCC | CTA | GAA | GCT | CAG | CCA | GAT | CCT | GAC | CTC | 2784 |
| Ser | Pro | Ser | Pro | Cys | Lys | Ser | Leu | Glu | Ala | Gln | Pro | Asp | Pro | Asp | Leu | |
| | | | 915 | | | | 920 | | | | | 925 | | | | |
| GGT | CCG | GGC | TCT | GGT | TTC | CCT | GCC | CCT | ACT | GTT | GAG | TCC | ACA | CCT | GAT | 2832 |
| Gly | Pro | Gly | Ser | Gly | Phe | Pro | Ala | Pro | Thr | Val | Glu | Ser | Thr | Pro | Asp | |
| | | 930 | | | | 935 | | | | | 940 | | | | | |
| GTT | TGT | CCT | TCA | TCA | CCT | GCC | CTG | CAG | ACA | CCC | TCC | CTT | TCA | TCC | GGT | 2880 |
| Val | Cys | Pro | Ser | Ser | Pro | Ala | Leu | Gln | Thr | Pro | Ser | Leu | Ser | Ser | Gly | |
| 945 | | | | | 950 | | | | | 955 | | | | | 960 | |
| CAG | CTG | CCT | CCT | CTC | TTG | ATC | CCC | ACA | GAT | CCC | TCT | TCC | CCT | CCA | CCC | 2928 |
| Gln | Leu | Pro | Pro | Leu | Leu | Ile | Pro | Thr | Asp | Pro | Ser | Ser | Pro | Pro | Pro | |
| | | | | 965 | | | | | 970 | | | | | 975 | | |
| TGT | CCC | CCG | GTA | TTA | ACT | GTT | GCC | ACT | CCG | CCC | CCT | CCC | CTC | CTT | CCT | 2976 |
| Cys | Pro | Pro | Val | Leu | Thr | Val | Ala | Thr | Pro | Pro | Pro | Pro | Leu | Leu | Pro | |
| | | | 980 | | | | | 985 | | | | | 990 | | | |
| ACC | GTA | CCT | CTT | CCA | GCC | CCC | TCT | TCC | AGT | GCA | TCT | CCA | CAC | CCA | TGC | 3024 |
| Thr | Val | Pro | Leu | Pro | Ala | Pro | Ser | Ser | Ser | Ala | Ser | Pro | His | Pro | Cys | |
| | | 995 | | | | | 1000 | | | | | 1005 | | | | |
| CCC | TCT | CCA | CTC | TCA | AAT | GCC | ACC | GCA | CAG | TCC | CCA | CTT | CCA | ATT | CTG | 3072 |
| Pro | Ser | Pro | Leu | Ser | Asn | Ala | Thr | Ala | Gln | Ser | Pro | Leu | Pro | Ile | Leu | |
| | | 1010 | | | | | 1015 | | | | | 1020 | | | | |
| TCC | CCA | ACA | GTG | TCC | CCC | TCT | CCC | TCT | CCC | ATT | CCT | CCC | GTG | GAG | CCC | 3120 |
| Ser | Pro | Thr | Val | Ser | Pro | Ser | Pro | Ser | Pro | Ile | Pro | Pro | Val | Glu | Pro | |
| 1025 | | | | | 1030 | | | | | 1035 | | | | | 1040 | |
| CTG | ATG | TCT | GCC | GCC | TCA | CCC | GGG | CCT | CCA | ACA | CTT | TCT | TCT | TCC | TCC | 3168 |
| Leu | Met | Ser | Ala | Ala | Ser | Pro | Gly | Pro | Pro | Thr | Leu | Ser | Ser | Ser | Ser | |
| | | | | 1045 | | | | | 1050 | | | | | 1055 | | |
| TCT | TCA | TCT | TCC | TCC | TCC | TCG | TTT | TCT | TCT | TCA | TCT | TCC | TCC | TCT | 3216 |
| Ser | Ser | Ser | Ser | Ser | Ser | Ser | Phe | Ser | Ser | Ser | Ser | Ser | Ser | Ser | | |
| | | | 1060 | | | | | 1065 | | | | | 1070 | | | |
| TCT | CCT | TCT | CCA | CCT | CCT | CTC | TCC | GCA | ATA | TCA | TCT | GTT | GTT | TCC | TCT | 3264 |
| Ser | Pro | Ser | Pro | Pro | Pro | Leu | Ser | Ala | Ile | Ser | Ser | Val | Val | Ser | Ser | |
| | | | 1075 | | | | | 1080 | | | | | 1085 | | | |
| GGT | GAT | AAT | CTG | GAG | GCT | TCT | CTC | CCC | ATG | ATA | TCT | TTC | AAA | CAG | GAG | 3312 |
| Gly | Asp | Asn | Leu | Glu | Ala | Ser | Leu | Pro | Met | Ile | Ser | Phe | Lys | Gln | Glu | |
| | | | 1090 | | | | | 1095 | | | | | 1100 | | | |
| GAA | TTA | GAG | AAT | GAA | GGT | CTG | AAA | CCC | AGG | GAA | GAG | CCC | CAG | TCT | GCT | 3360 |
| Glu | Leu | Glu | Asn | Glu | Gly | Leu | Lys | Pro | Arg | Glu | Glu | Pro | Gln | Ser | Ala | |
| 1105 | | | | | 1110 | | | | | 1115 | | | | | 1120 | |
| GCT | GAA | CAG | GAT | GTT | GTT | GTT | CAG | GAA | ACA | TTC | AAC | AAA | AAC | TTT | GTT | 3408 |
| Ala | Glu | Gln | Asp | Val | Val | Val | Gln | Glu | Thr | Phe | Asn | Lys | Asn | Phe | Val | |
| | | | | 1125 | | | | | 1130 | | | | | 1135 | | |

| | | | | | | | | | | | | | | | | |
|---|---|---|---|---|---|---|---|---|---|---|---|---|---|---|---|---|
| TGC | AAC | GTC | TGT | GAA | TCA | CCT | TTT | CTT | TCC | ATT | AAA | GAT | CTA | ACC | AAA | 3456 |
| Cys | Asn | Val | Cys | Glu | Ser | Pro | Phe | Leu | Ser | Ile | Lys | Asp | Leu | Thr | Lys | |
| | | | 1140 | | | | 1145 | | | | | 1150 | | | | |
| CAT | TTA | TCT | ATT | CAT | GCT | GAA | GAA | TGG | CCC | TTC | AAA | TGT | GAA | TTT | TGT | 3504 |
| His | Leu | Ser | Ile | His | Ala | Glu | Glu | Trp | Pro | Phe | Lys | Cys | Glu | Phe | Cys | |
| | | 1155 | | | | 1160 | | | | | 1165 | | | | | |
| GTG | CAG | CTT | TTT | AAG | GAT | AAA | ACG | GAC | TTG | TCA | GAA | CAT | CGC | TTT | TTG | 3552 |
| Val | Gln | Leu | Phe | Lys | Asp | Lys | Thr | Asp | Leu | Ser | Glu | His | Arg | Phe | Leu | |
| | 1170 | | | | | 1175 | | | | | 1180 | | | | | |
| CTT | CAT | GGA | GTT | GGG | AAT | ATC | TTT | GTG | TGT | TCT | GTT | TGT | AAA | AAA | GAA | 3600 |
| Leu | His | Gly | Val | Gly | Asn | Ile | Phe | Val | Cys | Ser | Val | Cys | Lys | Lys | Glu | |
| 1185 | | | | | 1190 | | | | | 1195 | | | | | 1200 | |
| TTT | GCT | TTT | TTG | TGC | AAT | TTG | CAG | CAG | CAC | CAG | CGA | GAT | CTC | CAC | CCA | 3648 |
| Phe | Ala | Phe | Leu | Cys | Asn | Leu | Gln | Gln | His | Gln | Arg | Asp | Leu | His | Pro | |
| | | | 1205 | | | | 1210 | | | | | 1215 | | | | |
| GAT | AAG | GTG | TGC | ACA | CAT | CAC | GAG | TTT | GAA | AGC | GGG | ACT | CTG | AGG | CCC | 3696 |
| Asp | Lys | Val | Cys | Thr | His | His | Glu | Phe | Glu | Ser | Gly | Thr | Leu | Arg | Pro | |
| | | | 1220 | | | | 1225 | | | | | 1230 | | | | |
| CAG | AAC | TTT | ACA | GAT | CCC | AGC | AAG | GCC | CAT | GTA | GAG | CAT | ATG | CAG | AGC | 3744 |
| Gln | Asn | Phe | Thr | Asp | Pro | Ser | Lys | Ala | His | Val | Glu | His | Met | Gln | Ser | |
| | | | 1235 | | | | 1240 | | | | | 1245 | | | | |
| TTG | CCA | GAA | GAT | CCT | TTA | GAA | ACT | TCT | AAA | GAA | GAA | GAG | GAG | TTA | AAT | 3792 |
| Leu | Pro | Glu | Asp | Pro | Leu | Glu | Thr | Ser | Lys | Glu | Glu | Glu | Glu | Leu | Asn | |
| | 1250 | | | | | 1255 | | | | | 1260 | | | | | |
| GAT | TCC | TCT | GAA | GAG | CTT | TAC | ACG | ACT | ATA | AAA | ATA | ATG | GCT | TCT | GGA | 3840 |
| Asp | Ser | Ser | Glu | Glu | Leu | Tyr | Thr | Thr | Ile | Lys | Ile | Met | Ala | Ser | Gly | |
| 1265 | | | | | 1270 | | | | | 1275 | | | | | 1280 | |
| ATA | AAG | ACA | AAA | GAT | CCA | GAT | GTT | CGA | TTG | GGC | CTC | AAT | CAG | CAT | TAC | 3888 |
| Ile | Lys | Thr | Lys | Asp | Pro | Asp | Val | Arg | Leu | Gly | Leu | Asn | Gln | His | Tyr | |
| | | | | 1285 | | | | | 1290 | | | | | 1295 | | |
| CCA | AGC | TTT | AAA | CCA | CCT | CCA | TTT | CAG | TAC | CAT | CAC | CGT | AAC | CCC | ATG | 3936 |
| Pro | Ser | Phe | Lys | Pro | Pro | Pro | Phe | Gln | Tyr | His | His | Arg | Asn | Pro | Met | |
| | | | 1300 | | | | 1305 | | | | | 1310 | | | | |
| GGG | ATT | GGT | GTG | ACA | GCC | ACA | AAT | TTC | ACT | ACA | CAC | AAT | ATT | CCA | CAG | 3984 |
| Gly | Ile | Gly | Val | Thr | Ala | Thr | Asn | Phe | Thr | Thr | His | Asn | Ile | Pro | Gln | |
| | | | 1315 | | | | 1320 | | | | | 1325 | | | | |
| ACT | TTC | ACT | ACC | GCC | ATT | CGC | TGC | ACA | AAG | TGT | GGA | AAA | GGT | GTC | GAC | 4032 |
| Thr | Phe | Thr | Thr | Ala | Ile | Arg | Cys | Thr | Lys | Cys | Gly | Lys | Gly | Val | Asp | |
| | 1330 | | | | | 1335 | | | | | 1340 | | | | | |
| AAT | ATG | CCG | GAG | TTG | CAC | AAA | CAT | ATC | CTG | GCT | TGT | GCT | TCT | GCA | AGT | 4080 |
| Asn | Met | Pro | Glu | Leu | His | Lys | His | Ile | Leu | Ala | Cys | Ala | Ser | Ala | Ser | |
| 1345 | | | | | 1350 | | | | | 1355 | | | | | 1360 | |
| GAC | AAG | AAG | AGG | TAC | ACG | CCT | AAG | AAA | AAC | CCA | GTA | CCA | TTA | AAA | CAA | 4128 |
| Asp | Lys | Lys | Arg | Tyr | Thr | Pro | Lys | Lys | Asn | Pro | Val | Pro | Leu | Lys | Gln | |
| | | | | 1365 | | | | | 1370 | | | | | 1375 | | |
| ACT | GTG | CAA | CCC | AAA | AAT | GGC | GTG | GTG | GTT | TTA | GAT | AAC | TCT | GGG | AAA | 4176 |
| Thr | Val | Gln | Pro | Lys | Asn | Gly | Val | Val | Val | Leu | Asp | Asn | Ser | Gly | Lys | |
| | | | 1380 | | | | 1385 | | | | | 1390 | | | | |
| AAT | GCC | TTC | CGA | CGA | ATG | GGA | CAG | CCC | AAA | AGG | CTT | AAC | TTT | AGT | GTT | 4224 |
| Asn | Ala | Phe | Arg | Arg | Met | Gly | Gln | Pro | Lys | Arg | Leu | Asn | Phe | Ser | Val | |
| | | 1395 | | | | 1400 | | | | | 1405 | | | | | |
| GAG | CTC | AGC | AAA | ATG | TCG | TCG | AAT | AAG | CTC | AAA | TTA | AAT | GCA | TTG | AAG | 4272 |
| Glu | Leu | Ser | Lys | Met | Ser | Ser | Asn | Lys | Leu | Lys | Leu | Asn | Ala | Leu | Lys | |
| | | 1410 | | | | 1415 | | | | | 1420 | | | | | |
| AAA | AAA | AAT | CAG | CTA | GTA | CAG | AAA | GCA | ATT | CTT | CAG | AAA | AAC | AAA | TCT | 4320 |
| Lys | Lys | Asn | Gln | Leu | Val | Gln | Lys | Ala | Ile | Leu | Gln | Lys | Asn | Lys | Ser | |
| 1425 | | | | | 1430 | | | | | 1435 | | | | | 1440 | |
| GCA | AAG | CAG | AAG | GCC | GAC | TTG | AAA | AAT | GCT | TGT | GAG | TCA | TCC | TCT | CAC | 4368 |
| Ala | Lys | Gln | Lys | Ala | Asp | Leu | Lys | Asn | Ala | Cys | Glu | Ser | Ser | Ser | His | |
| | | | | 1445 | | | | | 1450 | | | | | 1455 | | |

| | | | | | | | | | | | | | | | | |
|---|---|---|---|---|---|---|---|---|---|---|---|---|---|---|---|---|
| ATC | TGC | CCT | TAC | TGT | AAT | CGA | GAG | TTC | ACT | TAC | ATT | GGA | AGC | CTG | AAT | 4416 |
| Ile | Cys | Pro | Tyr | Cys | Asn | Arg | Glu | Phe | Thr | Tyr | Ile | Gly | Ser | Leu | Asn | |
| | | | 1460 | | | | 1465 | | | | | 1470 | | | | |
| AAA | CAC | GCC | GCC | TTC | AGC | TGT | CCC | AAA | AAA | CCC | CTT | TCT | CCT | CCC | AAA | 4464 |
| Lys | His | Ala | Ala | Phe | Ser | Cys | Pro | Lys | Lys | Pro | Leu | Ser | Pro | Pro | Lys | |
| | | 1475 | | | | | 1480 | | | | | 1485 | | | | |
| AAA | AAA | GTT | TCT | CAT | TCA | TCT | AAG | AAA | GGT | GGA | CAC | TCA | TCA | CCT | GCA | 4512 |
| Lys | Lys | Val | Ser | His | Ser | Ser | Lys | Lys | Gly | Gly | His | Ser | Ser | Pro | Ala | |
| | 1490 | | | | | 1495 | | | | | 1500 | | | | | |
| AGT | AGT | GAC | AAA | AAC | AGT | AAC | AGC | AAC | CAC | CGC | AGA | CGG | ACA | GCG | GAT | 4560 |
| Ser | Ser | Asp | Lys | Asn | Ser | Asn | Ser | Asn | His | Arg | Arg | Arg | Thr | Ala | Asp | |
| 1505 | | | | | 1510 | | | | | 1515 | | | | | 1520 | |
| GCG | GAG | ATT | AAA | ATG | CAA | AGC | ATG | CAG | ACT | CCG | TTG | GGC | AAG | ACC | AGA | 4608 |
| Ala | Glu | Ile | Lys | Met | Gln | Ser | Met | Gln | Thr | Pro | Leu | Gly | Lys | Thr | Arg | |
| | | | | 1525 | | | | | 1530 | | | | | 1535 | | |
| GCC | CGC | AGC | TCA | GGC | CCC | ACC | CAA | GTC | CCA | CTT | CCC | TCC | TCA | TCC | TTC | 4656 |
| Ala | Arg | Ser | Ser | Gly | Pro | Thr | Gln | Val | Pro | Leu | Pro | Ser | Ser | Ser | Phe | |
| | | | | 1540 | | | | | 1545 | | | | | 1550 | | |
| AGG | TCC | AAG | CAG | AAC | GTC | AAG | TTT | GCA | GCT | TCG | GTG | AAA | TCC | AAA | AAA | 4704 |
| Arg | Ser | Lys | Gln | Asn | Val | Lys | Phe | Ala | Ala | Ser | Val | Lys | Ser | Lys | Lys | |
| | | | 1555 | | | | 1560 | | | | | 1565 | | | | |
| CCA | AGC | TCC | TCC | TCT | TTA | AGG | AAC | TCC | AGC | CCG | ATA | AGA | ATG | GCC | AAA | 4752 |
| Pro | Ser | Ser | Ser | Ser | Leu | Arg | Asn | Ser | Ser | Pro | Ile | Arg | Met | Ala | Lys | |
| | | | 1570 | | | | 1575 | | | | | 1580 | | | | |
| ATA | ACT | CAT | GTT | GAG | GGG | AAA | AAA | CCT | AAA | GCT | GTG | GCC | AAG | AAT | CAT | 4800 |
| Ile | Thr | His | Val | Glu | Gly | Lys | Lys | Pro | Lys | Ala | Val | Ala | Lys | Asn | His | |
| 1585 | | | | | 1590 | | | | | 1595 | | | | | 1600 | |
| TCT | GCT | CAG | CTT | TCC | AGC | AAA | ACA | TCG | CGG | AGC | CTG | CAC | GTG | AGG | GTA | 4848 |
| Ser | Ala | Gln | Leu | Ser | Ser | Lys | Thr | Ser | Arg | Ser | Leu | His | Val | Arg | Val | |
| | | | | 1605 | | | | | 1610 | | | | | 1615 | | |
| CAG | AAA | AGC | AAA | GCT | GTT | TTA | CAA | AGC | AAA | TCC | ACC | TTG | GCG | AGT | AAG | 4896 |
| Gln | Lys | Ser | Lys | Ala | Val | Leu | Gln | Ser | Lys | Ser | Thr | Leu | Ala | Ser | Lys | |
| | | | 1620 | | | | | 1625 | | | | | 1630 | | | |
| AAA | AGA | ACA | GAC | CGG | TTC | AAT | ATA | AAA | TCT | AGA | GAG | CGG | AGT | GGG | GGG | 4944 |
| Lys | Arg | Thr | Asp | Arg | Phe | Asn | Ile | Lys | Ser | Arg | Glu | Arg | Ser | Gly | Gly | |
| | | | 1635 | | | | 1640 | | | | | 1645 | | | | |
| CCA | GTC | ACC | CGG | AGC | CTT | CAG | CTG | GCA | GCT | GCT | GCT | GAC | TTG | AGT | GAG | 4992 |
| Pro | Val | Thr | Arg | Ser | Leu | Gln | Leu | Ala | Ala | Ala | Ala | Asp | Leu | Ser | Glu | |
| | | | 1650 | | | | | 1655 | | | | | 1660 | | | |
| AAC | AAG | AGA | GAG | GAC | GGC | AGC | GCC | AAG | CAG | GAG | CTG | AAG | GAC | TTC | AGC | 5040 |
| Asn | Lys | Arg | Glu | Asp | Gly | Ser | Ala | Lys | Gln | Glu | Leu | Lys | Asp | Phe | Ser | |
| 1665 | | | | | 1670 | | | | | 1675 | | | | | 1680 | |
| TAC | AGC | CTC | CGC | TTG | GCG | TCC | CGA | TGC | TCT | CCA | CCA | GCC | GCC | TCT | TAC | 5088 |
| Tyr | Ser | Leu | Arg | Leu | Ala | Ser | Arg | Cys | Ser | Pro | Pro | Ala | Ala | Ser | Tyr | |
| | | | | 1685 | | | | | 1690 | | | | | 1695 | | |
| ATC | ACC | AGG | CAG | TAT | AGG | AAG | GTC | AAA | GCT | CCG | GCT | GCA | GCC | CAG | TTC | 5136 |
| Ile | Thr | Arg | Gln | Tyr | Arg | Lys | Val | Lys | Ala | Pro | Ala | Ala | Ala | Gln | Phe | |
| | | | | 1700 | | | | | 1705 | | | | | 1710 | | |
| CAG | GGA | CCA | TTC | TTC | AAA | GAG | T | AGACACTCTG | GCTGCTCCCT | GACAG | | | | | | 5183 |
| Gln | Gly | Pro | Phe | Phe | Lys | Glu | | | | | | | | | | |
| | | | | 1715 | | | | | | | | | | | | |

( 2 ) INFORMATION FOR SEQ ID NO:4:

( i ) SEQUENCE CHARACTERISTICS:
        ( A ) LENGTH: 1719 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Asn | Gln | Asn | Thr | Thr | Glu | Pro | Val | Ala | Ala | Thr | Glu | Thr | Leu | Ala |
|---|---|---|---|---|---|---|---|---|---|---|---|---|---|---|---|
| 1 | | | | 5 | | | | | 10 | | | | | 15 | |

| Glu | Val | Pro | Glu | His | Val | Leu | Arg | Gly | Leu | Pro | Glu | Glu | Val | Arg | Leu |
|---|---|---|---|---|---|---|---|---|---|---|---|---|---|---|---|
| | | | 20 | | | | 25 | | | | | 30 | | | |

| Phe | Pro | Ser | Ala | Val | Asp | Lys | Thr | Arg | Ile | Gly | Val | Trp | Ala | Thr | Lys |
|---|---|---|---|---|---|---|---|---|---|---|---|---|---|---|---|
| | | 35 | | | | | 40 | | | | | 45 | | | |

| Pro | Ile | Leu | Lys | Gly | Lys | Lys | Phe | Gly | Pro | Phe | Val | Gly | Asp | Lys | Lys |
|---|---|---|---|---|---|---|---|---|---|---|---|---|---|---|---|
| | | 50 | | | | 55 | | | | | 60 | | | | |

| Lys | Arg | Ser | Gln | Val | Lys | Asn | Asn | Val | Tyr | Met | Trp | Glu | Val | Tyr | Tyr |
|---|---|---|---|---|---|---|---|---|---|---|---|---|---|---|---|
| 65 | | | | | 70 | | | | | 75 | | | | | 80 |

| Pro | Asn | Leu | Gly | Trp | Met | Cys | Ile | Asp | Ala | Thr | Asp | Pro | Glu | Lys | Gly |
|---|---|---|---|---|---|---|---|---|---|---|---|---|---|---|---|
| | | | | 85 | | | | | 90 | | | | | 95 | |

| Asn | Trp | Leu | Arg | Tyr | Val | Asn | Trp | Ala | Cys | Ser | Gly | Glu | Glu | Gln | Asn |
|---|---|---|---|---|---|---|---|---|---|---|---|---|---|---|---|
| | | | 100 | | | | | 105 | | | | | 110 | | |

| Leu | Phe | Pro | Leu | Glu | Ile | Asn | Arg | Ala | Ile | Tyr | Tyr | Lys | Thr | Leu | Lys |
|---|---|---|---|---|---|---|---|---|---|---|---|---|---|---|---|
| | | 115 | | | | | 120 | | | | | 125 | | | |

| Pro | Ile | Ala | Pro | Gly | Glu | Glu | Leu | Leu | Val | Trp | Tyr | Asn | Gly | Glu | Asp |
|---|---|---|---|---|---|---|---|---|---|---|---|---|---|---|---|
| | | 130 | | | | 135 | | | | | 140 | | | | |

| Asn | Pro | Glu | Ile | Ala | Ala | Ile | Glu | Glu | Glu | Arg | Ala | Ser | Ala | Arg | |
|---|---|---|---|---|---|---|---|---|---|---|---|---|---|---|---|
| 145 | | | | | 150 | | | | | 155 | | | | | 160 |

| Ser | Lys | Arg | Ser | Ser | Pro | Lys | Ser | Arg | Lys | Gly | Lys | Lys | Lys | Ser | Gln |
|---|---|---|---|---|---|---|---|---|---|---|---|---|---|---|---|
| | | | | 165 | | | | | 170 | | | | | 175 | |

| Glu | Asn | Lys | Asn | Lys | Gly | Asn | Lys | Ile | Gln | Asp | Ile | Gln | Leu | Lys | Thr |
|---|---|---|---|---|---|---|---|---|---|---|---|---|---|---|---|
| | | | 180 | | | | | 185 | | | | | 190 | | |

| Ser | Glu | Pro | Asp | Phe | Thr | Ser | Ala | Asn | Met | Arg | Asp | Ser | Ala | Glu | Gly |
|---|---|---|---|---|---|---|---|---|---|---|---|---|---|---|---|
| | | 195 | | | | | 200 | | | | | 205 | | | |

| Pro | Lys | Glu | Asp | Glu | Glu | Lys | Pro | Ser | Ala | Ser | Ala | Leu | Glu | Gln | Pro |
|---|---|---|---|---|---|---|---|---|---|---|---|---|---|---|---|
| | 210 | | | | | 215 | | | | | 220 | | | | |

| Ala | Thr | Leu | Gln | Glu | Val | Ala | Ser | Gln | Glu | Val | Pro | Pro | Glu | Leu | Ala |
|---|---|---|---|---|---|---|---|---|---|---|---|---|---|---|---|
| 225 | | | | | 230 | | | | | 235 | | | | | 240 |

| Thr | Pro | Ala | Pro | Ala | Trp | Glu | Pro | Gln | Pro | Glu | Pro | Asp | Glu | Arg | Leu |
|---|---|---|---|---|---|---|---|---|---|---|---|---|---|---|---|
| | | | | 245 | | | | 250 | | | | | 255 | | |

| Glu | Ala | Ala | Ala | Cys | Glu | Val | Asn | Asp | Leu | Gly | Glu | Glu | Glu | Glu | Glu |
|---|---|---|---|---|---|---|---|---|---|---|---|---|---|---|---|
| | | | 260 | | | | | 265 | | | | | 270 | | |

| Glu | Glu | Glu | Glu | Asp | Glu | Glu | Glu | Glu | Glu | Asp | Asp | Asp | Asp | Asp | Glu |
|---|---|---|---|---|---|---|---|---|---|---|---|---|---|---|---|
| | | 275 | | | | | 280 | | | | | 285 | | | |

| Leu | Glu | Asp | Glu | Gly | Glu | Glu | Glu | Ala | Ser | Met | Pro | Asn | Glu | Asn | Ser |
|---|---|---|---|---|---|---|---|---|---|---|---|---|---|---|---|
| | 290 | | | | | 295 | | | | | 300 | | | | |

| Val | Lys | Glu | Pro | Glu | Ile | Arg | Cys | Asp | Glu | Lys | Pro | Glu | Asp | Leu | Leu |
|---|---|---|---|---|---|---|---|---|---|---|---|---|---|---|---|
| 305 | | | | | 310 | | | | | 315 | | | | | 320 |

| Glu | Glu | Pro | Lys | Thr | Thr | Ser | Glu | Glu | Thr | Leu | Glu | Asp | Cys | Ser | Glu |
|---|---|---|---|---|---|---|---|---|---|---|---|---|---|---|---|
| | | | | 325 | | | | | 330 | | | | | 335 | |

| Val | Thr | Pro | Ala | Met | Gln | Ile | Pro | Arg | Thr | Lys | Glu | Glu | Ala | Asn | Gly |
|---|---|---|---|---|---|---|---|---|---|---|---|---|---|---|---|
| | | | 340 | | | | | 345 | | | | | 350 | | |

| Asp | Val | Phe | Glu | Thr | Phe | Met | Phe | Pro | Cys | Gln | His | Cys | Glu | Arg | Lys |
|---|---|---|---|---|---|---|---|---|---|---|---|---|---|---|---|
| | | 355 | | | | | 360 | | | | | 365 | | | |

| Phe | Thr | Thr | Lys | Gln | Gly | Leu | Glu | Arg | His | Met | His | Ile | His | Ile | Ser |
|---|---|---|---|---|---|---|---|---|---|---|---|---|---|---|---|
| | | 370 | | | | | 375 | | | | | 380 | | | |

| Thr | Val | Asn | His | Ala | Phe | Lys | Cys | Lys | Tyr | Cys | Gly | Lys | Ala | Phe | Gly |
|---|---|---|---|---|---|---|---|---|---|---|---|---|---|---|---|
| 385 | | | | | 390 | | | | | 395 | | | | | 400 |

| Thr | Gln | Ile | Asn | Arg | Arg | Arg | His | Glu | Arg | Arg | His | Glu | Ala | Gly | Leu |
|---|---|---|---|---|---|---|---|---|---|---|---|---|---|---|---|
| | | | | 405 | | | | | 410 | | | | | 415 | |

| Lys | Arg | Lys | Pro | Ser | Gln | Thr | Leu | Gln | Pro | Ser | Glu | Asp | Leu | Ala | Asp |
|---|---|---|---|---|---|---|---|---|---|---|---|---|---|---|---|
| | | | 420 | | | | | 425 | | | | | 430 | | |

```
Gly Lys Ala Ser Gly Glu Asn Val Ala Ser Lys Asp Asp Ser Ser Pro
            435                 440                 445
Pro Ser Leu Gly Pro Asp Cys Leu Ile Met Asn Ser Glu Lys Ala Ser
    450                 455                 460
Gln Asp Thr Ile Asn Ser Ser Val Val Glu Glu Asn Gly Glu Val Lys
465                 470                 475                 480
Glu Leu His Pro Cys Lys Tyr Cys Lys Lys Val Phe Gly Thr His Thr
                485                 490                 495
Asn Met Arg Arg His Gln Arg Arg Val His Glu Arg His Leu Ile Pro
            500                 505                 510
Lys Gly Val Arg Arg Lys Gly Gly Leu Glu Glu Pro Gln Pro Pro Ala
            515                 520                 525
Glu Gln Ala Gln Ala Thr Gln Asn Val Tyr Val Pro Ser Thr Glu Pro
            530                 535                 540
Glu Glu Glu Gly Glu Ala Asp Asp Val Tyr Ile Met Asp Ile Ser Ser
545                 550                 555                 560
Asn Ile Ser Glu Asn Leu Asn Tyr Tyr Ile Asp Gly Lys Ile Gln Thr
                565                 570                 575
Asn Asn Asn Thr Ser Asn Cys Asp Val Ile Glu Met Glu Ser Ala Ser
            580                 585                 590
Ala Asp Leu Tyr Gly Ile Asn Cys Leu Leu Thr Pro Val Thr Val Glu
            595                 600                 605
Ile Thr Gln Asn Ile Lys Thr Thr Gln Val Pro Val Thr Glu Asp Leu
            610                 615                 620
Pro Lys Glu Pro Leu Gly Ser Thr Asn Ser Glu Ala Lys Lys Arg Arg
625                 630                 635                 640
Thr Ala Ser Pro Pro Ala Leu Pro Lys Ile Lys Ala Glu Thr Asp Ser
                645                 650                 655
Asp Pro Met Val Pro Ser Cys Ser Leu Ser Leu Pro Leu Ser Ile Ser
            660                 665                 670
Thr Thr Glu Ala Val Ser Phe His Lys Glu Lys Ser Val Tyr Leu Ser
            675                 680                 685
Ser Lys Leu Lys Gln Leu Leu Gln Thr Gln Asp Lys Leu Thr Pro Pro
    690                 695                 700
Ala Gly Ile Ser Ala Thr Glu Ile Ala Lys Leu Gly Pro Val Cys Val
705                 710                 715                 720
Ser Ala Pro Ala Ser Met Leu Pro Val Thr Ser Ser Arg Phe Lys Arg
                725                 730                 735
Arg Thr Ser Ser Pro Pro Ser Ser Pro Gln His Ser Pro Ala Leu Arg
            740                 745                 750
Asp Phe Gly Lys Pro Ser Asp Gly Lys Ala Ala Trp Thr Asp Ala Gly
            755                 760                 765
Leu Thr Ser Lys Lys Ser Lys Leu Glu Ser His Ser Asp Ser Pro Ala
    770                 775                 780
Trp Ser Leu Ser Gly Arg Asp Glu Arg Glu Thr Val Ser Pro Pro Cys
785                 790                 795                 800
Phe Asp Glu Tyr Lys Met Ser Lys Glu Trp Thr Ala Ser Ser Ala Phe
                805                 810                 815
Ser Ser Val Cys Asn Gln Gln Pro Leu Asp Leu Ser Ser Gly Val Lys
            820                 825                 830
Gln Lys Ala Glu Gly Thr Gly Lys Thr Pro Val Gln Trp Glu Ser Val
            835                 840                 845
Leu Asp Leu Ser Val His Lys Lys His Cys Ser Asp Ser Glu Gly Lys
```

-continued

|     |     |     | 850 |     |     |     |     | 855 |     |     |     |     | 860 |     |
| --- | --- | --- | --- | --- | --- | --- | --- | --- | --- | --- | --- | --- | --- | --- |

Glu Phe Lys Glu Ser His Ser Val Gln Pro Thr Cys Ser Ala Val Lys
865 870 875 880

Lys Arg Lys Pro Thr Thr Cys Met Leu Gln Lys Val Leu Leu Asn Glu
885 890 895

Tyr Asn Gly Ile Asp Leu Pro Val Glu Asn Pro Ala Asp Gly Thr Arg
900 905 910

Ser Pro Ser Pro Cys Lys Ser Leu Glu Ala Gln Pro Asp Pro Asp Leu
915 920 925

Gly Pro Gly Ser Gly Phe Pro Ala Pro Thr Val Glu Ser Thr Pro Asp
930 935 940

Val Cys Pro Ser Ser Pro Ala Leu Gln Thr Pro Ser Leu Ser Ser Gly
945 950 955 960

Gln Leu Pro Pro Leu Leu Ile Pro Thr Asp Pro Ser Ser Pro Pro Pro
965 970 975

Cys Pro Pro Val Leu Thr Val Ala Thr Pro Pro Pro Pro Leu Leu Pro
980 985 990

Thr Val Pro Leu Pro Ala Pro Ser Ser Ser Ala Ser Pro His Pro Cys
995 1000 1005

Pro Ser Pro Leu Ser Asn Ala Thr Ala Gln Ser Pro Leu Pro Ile Leu
1010 1015 1020

Ser Pro Thr Val Ser Pro Ser Pro Ser Pro Ile Pro Pro Val Glu Pro
1025 1030 1035 1040

Leu Met Ser Ala Ala Ser Pro Gly Pro Pro Thr Leu Ser Ser Ser Ser
1045 1050 1055

Ser Ser Ser Ser Ser Ser Ser Ser Phe Ser Ser Ser Ser Ser Ser Ser
1060 1065 1070

Ser Pro Ser Pro Pro Pro Leu Ser Ala Ile Ser Ser Val Val Ser Ser
1075 1080 1085

Gly Asp Asn Leu Glu Ala Ser Leu Pro Met Ile Ser Phe Lys Gln Glu
1090 1095 1100

Glu Leu Glu Asn Glu Gly Leu Lys Pro Arg Glu Glu Pro Gln Ser Ala
1105 1110 1115 1120

Ala Glu Gln Asp Val Val Val Gln Glu Thr Phe Asn Lys Asn Phe Val
1125 1130 1135

Cys Asn Val Cys Glu Ser Pro Phe Leu Ser Ile Lys Asp Leu Thr Lys
1140 1145 1150

His Leu Ser Ile His Ala Glu Glu Trp Pro Phe Lys Cys Glu Phe Cys
1155 1160 1165

Val Gln Leu Phe Lys Asp Lys Thr Asp Leu Ser Glu His Arg Phe Leu
1170 1175 1180

Leu His Gly Val Gly Asn Ile Phe Val Cys Ser Val Cys Lys Lys Glu
1185 1190 1195 1200

Phe Ala Phe Leu Cys Asn Leu Gln Gln His Gln Arg Asp Leu His Pro
1205 1210 1215

Asp Lys Val Cys Thr His His Glu Phe Glu Ser Gly Thr Leu Arg Pro
1220 1225 1230

Gln Asn Phe Thr Asp Pro Ser Lys Ala His Val Glu His Met Gln Ser
1235 1240 1245

Leu Pro Glu Asp Pro Leu Glu Thr Ser Lys Glu Glu Glu Glu Leu Asn
1250 1255 1260

Asp Ser Ser Glu Glu Leu Tyr Thr Thr Ile Lys Ile Met Ala Ser Gly
1265 1270 1275 1280

-continued

```
Ile  Lys  Thr  Lys  Asp  Pro  Asp  Val  Arg  Leu  Gly  Leu  Asn  Gln  His  Tyr
               1285                1290                     1295

Pro  Ser  Phe  Lys  Pro  Pro  Pro  Phe  Gln  Tyr  His  His  Arg  Asn  Pro  Met
               1300                1305                     1310

Gly  Ile  Gly  Val  Thr  Ala  Thr  Asn  Phe  Thr  Thr  His  Asn  Ile  Pro  Gln
               1315                1320                     1325

Thr  Phe  Thr  Thr  Ala  Ile  Arg  Cys  Thr  Lys  Cys  Gly  Lys  Gly  Val  Asp
          1330                1335                     1340

Asn  Met  Pro  Glu  Leu  His  Lys  His  Ile  Leu  Ala  Cys  Ala  Ser  Ala  Ser
1345                     1350                     1355                     1360

Asp  Lys  Lys  Arg  Tyr  Thr  Pro  Lys  Lys  Asn  Pro  Val  Pro  Leu  Lys  Gln
               1365                1370                     1375

Thr  Val  Gln  Pro  Lys  Asn  Gly  Val  Val  Val  Leu  Asp  Asn  Ser  Gly  Lys
               1380                1385                     1390

Asn  Ala  Phe  Arg  Arg  Met  Gly  Gln  Pro  Lys  Arg  Leu  Asn  Phe  Ser  Val
               1395                1400                     1405

Glu  Leu  Ser  Lys  Met  Ser  Ser  Asn  Lys  Leu  Lys  Leu  Asn  Ala  Leu  Lys
               1410                1415                     1420

Lys  Lys  Asn  Gln  Leu  Val  Gln  Lys  Ala  Ile  Leu  Gln  Lys  Asn  Lys  Ser
1425                     1430                     1435                     1440

Ala  Lys  Gln  Lys  Ala  Asp  Leu  Lys  Asn  Ala  Cys  Glu  Ser  Ser  Ser  His
               1445                1450                     1455

Ile  Cys  Pro  Tyr  Cys  Asn  Arg  Glu  Phe  Thr  Tyr  Ile  Gly  Ser  Leu  Asn
               1460                1465                     1470

Lys  His  Ala  Ala  Phe  Ser  Cys  Pro  Lys  Lys  Pro  Leu  Ser  Pro  Pro  Lys
               1475                1480                     1485

Lys  Lys  Val  Ser  His  Ser  Ser  Lys  Lys  Gly  Gly  His  Ser  Ser  Pro  Ala
               1490                1495                     1500

Ser  Ser  Asp  Lys  Asn  Ser  Asn  Ser  Asn  His  Arg  Arg  Arg  Thr  Ala  Asp
1505                     1510                     1515                     1520

Ala  Glu  Ile  Lys  Met  Gln  Ser  Met  Gln  Thr  Pro  Leu  Gly  Lys  Thr  Arg
               1525                1530                     1535

Ala  Arg  Ser  Ser  Gly  Pro  Thr  Gln  Val  Pro  Leu  Pro  Ser  Ser  Ser  Phe
               1540                1545                     1550

Arg  Ser  Lys  Gln  Asn  Val  Lys  Phe  Ala  Ala  Ser  Val  Lys  Ser  Lys  Lys
               1555                1560                     1565

Pro  Ser  Ser  Ser  Ser  Leu  Arg  Asn  Ser  Ser  Pro  Ile  Arg  Met  Ala  Lys
               1570                1575                     1580

Ile  Thr  His  Val  Glu  Gly  Lys  Lys  Pro  Lys  Ala  Val  Ala  Lys  Asn  His
1585                     1590                     1595                     1600

Ser  Ala  Gln  Leu  Ser  Ser  Lys  Thr  Ser  Arg  Ser  Leu  His  Val  Arg  Val
               1605                1610                     1615

Gln  Lys  Ser  Lys  Ala  Val  Leu  Gln  Ser  Lys  Ser  Thr  Leu  Ala  Ser  Lys
               1620                1625                     1630

Lys  Arg  Thr  Asp  Arg  Phe  Asn  Ile  Lys  Ser  Arg  Glu  Arg  Ser  Gly  Gly
               1635                1640                     1645

Pro  Val  Thr  Arg  Ser  Leu  Gln  Leu  Ala  Ala  Ala  Ala  Asp  Leu  Ser  Glu
               1650                1655                     1660

Asn  Lys  Arg  Glu  Asp  Gly  Ser  Ala  Lys  Gln  Glu  Leu  Lys  Asp  Phe  Ser
1665                     1670                     1675                     1680

Tyr  Ser  Leu  Arg  Leu  Ala  Ser  Arg  Cys  Ser  Pro  Pro  Ala  Ala  Ser  Tyr
               1685                1690                     1695

Ile  Thr  Arg  Gln  Tyr  Arg  Lys  Val  Lys  Ala  Pro  Ala  Ala  Ala  Gln  Phe
               1700                1705                     1710
```

Gln Gly Pro Phe Phe Lys Glu
        1715

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:5:

Leu  Xaa  Cys  Xaa  Glu
1                   5

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( D ) TOPOLOGY: linear ( x i ) SEQUENCE DESCRIPTION: SEQ ID NO:6:

Glu  Ile  Arg  Cys  Glu  Glu  Lys  Pro  Glu  Asp  Leu
1                   5                        10

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( D ) TOPOLOGY: linear ( x i ) SEQUENCE DESCRIPTION: SEQ ID NO:7:

Lys  Pro  Glu  Asp  Leu  Leu  Glu  Glu  Pro  Gln  Ser
1                   5                        10

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:8:

Glu  Glu  Glu  Glu  Tyr  Met  Pro  Met  Glu
1                   5

( 2 ) INFORMATION FOR SEQ ID NO:9:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

AATCGATGAA  GAAGAAGAAT  ATATGCCTAT  GGAACA                                     36

( 2 ) INFORMATION FOR SEQ ID NO:10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TTCCATAGGC ATATATTCTT CTTCTTCATC GATTTG                                36

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CCGGAGATCC GGGCTGAAGA AAAGCCA                                           27

( 2 ) INFORMATION FOR SEQ ID NO:12:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TTCACACCGG ATCCCCGGCT CTTTCGC                                           27

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

TGGCTCTTCT AATAAGTC                                                     18

( 2 ) INFORMATION FOR SEQ ID NO:14:

( i ) SEQUENCE CHARACTERISTICS:
        ( A ) LENGTH: 15 amino acids
        ( B ) TYPE: amino acid
        ( D ) TOPOLOGY: linear ( i x ) FEATURE:
        ( A ) NAME/KEY: Peptide
        ( B ) LOCATION: 15
        ( D ) OTHER INFORMATION: /note= "Xaa = (I/V)"

( x i ) SEQUENCE DESCRIPTION: SEQ ID NO:14:

Gly Xaa Xaa Xaa Xaa Gly Lys Xaa Xaa Xaa Xaa Xaa Xaa Xaa Xaa
1               5                   10                  15

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

TCTCCACAGC ACAGCCCT                                                     18

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GGATAAGGAG GCTGTCTG                                                                                                    18

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GTGGTCCAAG AAACATTC                                                                                                    18

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

TCGTGTAAAG CTCTTCAG                                                                                                    18

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GATACATTCC ACAGCCTG                                                                                                    18

( 2 ) INFORMATION FOR SEQ ID NO:20:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:20:

Glu Asp Leu Leu Glu Glu
    1                    5

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:21:

Glu Asp Leu Leu Asn Glu
    1                    5

( 2 ) INFORMATION FOR SEQ ID NO:22:

( i ) SEQUENCE CHARACTERISTICS:
        ( A ) LENGTH: 8 amino acids
        ( B ) TYPE: amino acid
        ( D ) TOPOLOGY: linear ( i x ) FEATURE:
        ( A ) NAME/KEY: Peptide ( B ) LOCATION: 8
            ( D ) OTHER INFORMATION: /note= "Xaa = S or T"

( x i ) SEQUENCE DESCRIPTION: SEQ ID NO:22:

Gly  Xaa  Xaa  Xaa  Xaa  Gly  Lys  Xaa
    1                        5

( 2 ) INFORMATION FOR SEQ ID NO:23:

( i ) SEQUENCE CHARACTERISTICS:
            ( A ) LENGTH: 4 amino acids
            ( B ) TYPE: amino acid
            ( D ) TOPOLOGY: linear ( x i ) SEQUENCE DESCRIPTION: SEQ ID NO:23:

Asp  Xaa  Xaa  Gly
    1

( 2 ) INFORMATION FOR SEQ ID NO:24:

( i ) SEQUENCE CHARACTERISTICS:
            ( A ) LENGTH: 4 amino acids
            ( B ) TYPE: amino acid
            ( D ) TOPOLOGY: linear ( i x ) FEATURE:
            ( A ) NAME/KEY: Protein
            ( B ) LOCATION: 1
            ( D ) OTHER INFORMATION: /note= "Xaa = N or T"

( i x ) FEATURE:
            ( A ) NAME/KEY: Protein
            ( B ) LOCATION: 2
            ( D ) OTHER INFORMATION: /note= "Xaa = K or Q"

( x i ) SEQUENCE DESCRIPTION: SEQ ID NO:24:

Xaa  Xaa  Xaa  Asp
    1

( 2 ) INFORMATION FOR SEQ ID NO:25:

( i ) SEQUENCE CHARACTERISTICS:
            ( A ) LENGTH: 8 amino acids
            ( B ) TYPE: amino acid
            ( D ) TOPOLOGY: linear ( x i ) SEQUENCE DESCRIPTION: SEQ ID NO:25:

Gly  Gly  Thr  Gly  Thr  Gly  Ala  Ala
    1                        5

( 2 ) INFORMATION FOR SEQ ID NO:26:

( i ) SEQUENCE CHARACTERISTICS:
            ( A ) LENGTH: 6 amino acids
            ( B ) TYPE: amino acid
            ( D ) TOPOLOGY: linear ( x i ) SEQUENCE DESCRIPTION: SEQ ID NO:26:

Asp  Leu  Gly  Ile  Leu  Thr
    1                        5

( 2 ) INFORMATION FOR SEQ ID NO:27:

( i ) SEQUENCE CHARACTERISTICS:
            ( A ) LENGTH: 5 amino acids
            ( B ) TYPE: amino acid
            ( D ) TOPOLOGY: linear ( x i ) SEQUENCE DESCRIPTION: SEQ ID NO:27:

Asp Ser Leu Ile Thr
1               5

(2) INFORMATION FOR SEQ ID NO:28:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:28:

Asp Val Arg Thr
1

(2) INFORMATION FOR SEQ ID NO:29:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:29:

Asp Ala Phe Gly
1

(2) INFORMATION FOR SEQ ID NO:30:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:30:

Asp Leu Ser Gly
1

(2) INFORMATION FOR SEQ ID NO:31:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:31:

Thr Ser Leu Asp
1

(2) INFORMATION FOR SEQ ID NO:32:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:32:

Gly Asp Gly Ala Val Gly Lys Thr
1               5

(2) INFORMATION FOR SEQ ID NO:33:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:33:

Tyr Val Pro Thr
1

( 2 ) INFORMATION FOR SEQ ID NO:34:

( i ) SEQUENCE CHARACTERISTICS:
       ( A ) LENGTH: 4 amino acids
       ( B ) TYPE: amino acid
       ( D ) TOPOLOGY: linear ( x i ) SEQUENCE DESCRIPTION: SEQ ID NO:34:

Asp Thr Ala Gly
   1

( 2 ) INFORMATION FOR SEQ ID NO:35:

( i ) SEQUENCE CHARACTERISTICS:
       ( A ) LENGTH: 4 amino acids
       ( B ) TYPE: amino acid
       ( D ) TOPOLOGY: linear ( x i ) SEQUENCE DESCRIPTION: SEQ ID NO:35:

Thr Gln Ile Asp
   1

( 2 ) INFORMATION FOR SEQ ID NO:36:

( i ) SEQUENCE CHARACTERISTICS:
       ( A ) LENGTH: 8 amino acids
       ( B ) TYPE: amino acid
       ( D ) TOPOLOGY: linear ( x i ) SEQUENCE DESCRIPTION: SEQ ID NO:36:

Gly Val Asn Gly Val Gly Lys Ser
   1               5

( 2 ) INFORMATION FOR SEQ ID NO:37:

( i ) SEQUENCE CHARACTERISTICS:
       ( A ) LENGTH: 4 amino acids
       ( B ) TYPE: amino acid
       ( D ) TOPOLOGY: linear ( x i ) SEQUENCE DESCRIPTION: SEQ ID NO:37:

Thr Lys Phe Asp
   1

( 2 ) INFORMATION FOR SEQ ID NO:38:

( i ) SEQUENCE CHARACTERISTICS:
       ( A ) LENGTH: 8 amino acids
       ( B ) TYPE: amino acid
       ( D ) TOPOLOGY: linear ( x i ) SEQUENCE DESCRIPTION: SEQ ID NO:38:

Gly His Val Asp His Gly Lys Thr
   1               5

( 2 ) INFORMATION FOR SEQ ID NO:39:

( i ) SEQUENCE CHARACTERISTICS:
       ( A ) LENGTH: 12 amino acids
       ( B ) TYPE: amino acid
       ( D ) TOPOLOGY: linear ( x i ) SEQUENCE DESCRIPTION: SEQ ID NO:39:

Asp Xaa Xaa Xaa Xaa Xaa Xaa Xaa Xaa Xaa Xaa Thr
   1               5                   1 0

( 2 ) INFORMATION FOR SEQ ID NO:40:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:40:

Asp Cys Pro Gly
    1

( 2 ) INFORMATION FOR SEQ ID NO:41:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:41:

Asn Lys Cys Asp
    1

( 2 ) INFORMATION FOR SEQ ID NO:42:

( i ) SEQUENCE CHARACTERISTICS:
        ( A ) LENGTH: 8 amino acids
        ( B ) TYPE: amino acid
        ( D ) TOPOLOGY: linear ( x i ) SEQUENCE DESCRIPTION: SEQ ID NO:42:

Gly Ala Gly Gly Val Gly Lys Ser
    1                   5

( 2 ) INFORMATION FOR SEQ ID NO:43:

( i ) SEQUENCE CHARACTERISTICS:
        ( A ) LENGTH: 3 amino acids
        ( B ) TYPE: amino acid
        ( D ) TOPOLOGY: linear ( x i ) SEQUENCE DESCRIPTION: SEQ ID NO:43:

Asp Pro Thr
    1

( 2 ) INFORMATION FOR SEQ ID NO:44:

( i ) SEQUENCE CHARACTERISTICS:
        ( A ) LENGTH: 29 amino acids
        ( B ) TYPE: amino acid
        ( D ) TOPOLOGY: linear ( x i ) SEQUENCE DESCRIPTION: SEQ ID NO:44:

Thr Ala Pro Glu Asp Pro Asn Glu Glu Ala Val Ser Gln Ile Phe Pro
    1              5                            10                   15

Asp Ser Val Met Leu Ala Val Gln Glu Gly Ile Asp Leu
                  20                          25

( 2 ) INFORMATION FOR SEQ ID NO:45:

( i ) SEQUENCE CHARACTERISTICS:
        ( A ) LENGTH: 29 amino acids
        ( B ) TYPE: amino acid
        ( D ) TOPOLOGY: linear ( x i ) SEQUENCE DESCRIPTION: SEQ ID NO:45:

Thr Ala Pro Glu Asp Pro Asn Glu Glu Ala Val Ser Gln Ile Phe Pro
    1              5                            10                   15

Asp Ser Val Met Leu Ala Val Gln Glu Gly Ile Asp Leu
                20                  25

( 2 ) INFORMATION FOR SEQ ID NO:46:

( i ) SEQUENCE CHARACTERISTICS:
        ( A ) LENGTH: 29 amino acids
        ( B ) TYPE: amino acid
        ( D ) TOPOLOGY: linear ( x i ) SEQUENCE DESCRIPTION: SEQ ID NO:46:

Asp Gly Pro Glu Asp Pro Asn Glu Gly Ala Val Asn Gly Phe Phe Thr
1               5                   10                  15

Asp Ser Met Leu Leu Ala Ala Asp Glu Gly Leu Asp Ile
                20                  25

( 2 ) INFORMATION FOR SEQ ID NO:47:

( i ) SEQUENCE CHARACTERISTICS:
        ( A ) LENGTH: 29 amino acids
        ( B ) TYPE: amino acid
        ( D ) TOPOLOGY: linear ( x i ) SEQUENCE DESCRIPTION: SEQ ID NO:47:

Ser Ala Gly Glu Asp Asn Asn Glu Gln Ala Val Asn Glu Phe Phe Pro
1               5                   10                  15

Glu Ser Leu Ile Leu Ala Ala Ser Glu Gly Leu Phe Leu
                20                  25

( 2 ) INFORMATION FOR SEQ ID NO:48:

( i ) SEQUENCE CHARACTERISTICS:
        ( A ) LENGTH: 29 amino acids
        ( B ) TYPE: amino acid
        ( D ) TOPOLOGY: linear ( x i ) SEQUENCE DESCRIPTION: SEQ ID NO:48:

Thr Gly Gln Glu Asp Glu Asn Glu Glu Ala Val Asp Gly Val Phe Ser
1               5                   10                  15

Asp Ala Met Leu Leu Ala Ala Glu Glu Gly Ile Glu Met
                20                  25

( 2 ) INFORMATION FOR SEQ ID NO:49:

( i ) SEQUENCE CHARACTERISTICS:
        ( A ) LENGTH: 30 amino acids
        ( B ) TYPE: amino acid
        ( D ) TOPOLOGY: linear ( x i ) SEQUENCE DESCRIPTION: SEQ ID NO:49:

Asp Gly Phe Glu Glu Asp Ala Asn Gln Glu Ala Val Asp Gly Met Phe
1               5                   10                  15

Pro Glu Arg Leu Leu Ser Glu Ala Glu Ser Ala Ala Glu Ser
                20                  25                  30

( 2 ) INFORMATION FOR SEQ ID NO:50:

( i ) SEQUENCE CHARACTERISTICS:
        ( A ) LENGTH: 50 amino acids
        ( B ) TYPE: amino acid
        ( D ) TOPOLOGY: linear ( x i ) SEQUENCE DESCRIPTION: SEQ ID NO:50:

Ala Lys Tyr Asp Phe Lys Ala Thr Ala Asp Asp Glu Leu Ser Phe Lys
1               5                   10                  15

```
Arg Gly Asp Ile Leu Lys Tyr Leu Asn Glu Glu Cys Asp Gln Asn Trp
         20                  25                      30

Tyr Lys Ala Glu Leu Asn Gly Lys Asp Gly Phe Ile Pro Lys Asn Tyr
         35                  40                  45

Ile Glu
    50
```

( 2 ) INFORMATION FOR SEQ ID NO:51:

( i ) SEQUENCE CHARACTERISTICS:
      ( A ) LENGTH: 49 amino acids
      ( B ) TYPE: amino acid
      ( D ) TOPOLOGY: linear ( x i ) SEQUENCE DESCRIPTION: SEQ ID NO:51:

```
Ala Leu Phe Asp Phe Asp Pro Gln Glu Asp Gly Glu Leu Gly Phe Arg
1               5                   10                      15

Arg Gly Asp Phe Ile His Val Met Asp Asn Ser Asp Pro Asn Trp Trp
            20              25                      30

Lys Gly Ala Cys His Gly Gln Thr Gly Met Phe Pro Arg Asn Tyr Val
            35              40              45

Thr
```

( 2 ) INFORMATION FOR SEQ ID NO:52:

( i ) SEQUENCE CHARACTERISTICS:
      ( A ) LENGTH: 66 amino acids
      ( B ) TYPE: amino acid
      ( D ) TOPOLOGY: linear ( x i ) SEQUENCE DESCRIPTION: SEQ ID NO:52:

```
Ala Leu Tyr Asp Tyr Lys Lys Glu Arg Glu Glu Asp Ile Asp Leu His
1               5                   10                      15

Leu Gly Asp Ile Leu Thr Val Asn Lys Gly Ser Leu Val Ala Leu Gly
            20                  25                      30

Phe Ser Asp Gly Gln Glu Ala Arg Pro Glu Glu Ile Gly Trp Leu Asn
            35                  40                  45

Gly Tyr Asn Glu Thr Thr Gly Glu Arg Gly Asp Phe Pro Gly Thr Tyr
        50              55                  60

Val Glu
65
```

( 2 ) INFORMATION FOR SEQ ID NO:53:

( i ) SEQUENCE CHARACTERISTICS:
      ( A ) LENGTH: 49 amino acids
      ( B ) TYPE: amino acid
      ( D ) TOPOLOGY: linear ( x i ) SEQUENCE DESCRIPTION: SEQ ID NO:53:

```
Ala Leu Tyr Asp Phe Val Ala Ser Gly Asp Asn Thr Leu Ser Ile Thr
1               5                   10                      15

Lys Gly Glu Lys Leu Arg Val Leu Tyr Asn His Asn Gly Glu Trp Cys
            20                  25                      30

Glu Ala Gln Thr Lys Asn Gly Gln Gly Trp Val Pro Ser Asn Tyr Ile
            35                  40                  45

Thr
```

( 2 ) INFORMATION FOR SEQ ID NO:54:

( i ) SEQUENCE CHARACTERISTICS:

(A) LENGTH: 51 amino acids
(B) TYPE: amino acid
(D) TOPOLOGY: linear (xi) SEQUENCE DESCRIPTION: SEQ ID NO:54:

| Ala | Leu | Tyr | Asp | Tyr | Glu | Ser | Arg | Thr | Glu | Thr | Asp | Leu | Ala | Phe | Lys |
| 1 | | | | 5 | | | | | 10 | | | | | 15 | |

| Lys | Gly | Glu | Arg | Leu | Gln | Ile | Val | Met | Asn | Thr | Glu | Gly | Asp | Trp | Trp |
| | | | 20 | | | | | 25 | | | | | 30 | | |

| Leu | Ala | His | Ser | Leu | Thr | Thr | Gly | Gln | Thr | Gly | Tyr | Ile | Pro | Ser | Asn |
| | | 35 | | | | | 40 | | | | | 45 | | | |

| Tyr | Val | Ala |
| | | 50 |

(2) INFORMATION FOR SEQ ID NO:55:

(i) SEQUENCE CHARACTERISTICS:
(A) LENGTH: 52 amino acids
(B) TYPE: amino acid
(D) TOPOLOGY: linear (xi) SEQUENCE DESCRIPTION: SEQ ID NO:55:

| Ala | Ile | Leu | Pro | Tyr | Thr | Lys | Val | Pro | Asp | Thr | Asp | Glu | Ile | Ser | Phe |
| 1 | | | | 5 | | | | | 10 | | | | | 15 | |

| Leu | Lys | Gly | Asp | Met | Phe | Ile | Val | His | Asn | Glu | Leu | Glu | Asp | Gly | Trp |
| | | | 20 | | | | | 25 | | | | | 30 | | |

| Met | Trp | Val | Thr | Asn | Leu | Arg | Thr | Asp | Glu | Gln | Gly | Leu | Ile | Val | Glu |
| | | 35 | | | | | 40 | | | | | 45 | | | |

| Asp | Leu | Val | Glu |
| | | 50 | |

(2) INFORMATION FOR SEQ ID NO:56:

(i) SEQUENCE CHARACTERISTICS:
(A) LENGTH: 50 amino acids
(B) TYPE: amino acid
(D) TOPOLOGY: linear (xi) SEQUENCE DESCRIPTION: SEQ ID NO:56:

| Ala | Leu | Phe | Asp | Tyr | Lys | Ala | Gln | Arg | Glu | Asp | Glu | Leu | Thr | Phe | Thr |
| 1 | | | | 5 | | | | | 10 | | | | | 15 | |

| Lys | Ser | Ala | Ile | Ile | Gln | Asn | Val | Glu | Lys | Gln | Glu | Gly | Gly | Trp | Trp |
| | | | 20 | | | | | 25 | | | | | 30 | | |

| Arg | Gly | Asp | Tyr | Gly | Gly | Lys | Lys | Gln | Leu | Trp | Phe | Pro | Ser | Asn | Tyr |
| | | | 35 | | | | | 40 | | | | | 45 | | | |

| Val | Glu |
| | |
| | 50 |

(2) INFORMATION FOR SEQ ID NO:57:

(i) SEQUENCE CHARACTERISTICS:
(A) LENGTH: 50 amino acids
(B) TYPE: amino acid
(D) TOPOLOGY: linear (xi) SEQUENCE DESCRIPTION: SEQ ID NO:57:

| Ala | Leu | Phe | Asp | Phe | Lys | Gly | Asn | Asp | Glu | Asp | Leu | Pro | Phe | Lys |
| 1 | | | | 5 | | | | | 10 | | | | | 15 |

| Lys | Gly | Asp | Ile | Leu | Lys | Ile | Arg | Asp | Lys | Pro | Glu | Glu | Gln | Trp | Trp |
| | | | 20 | | | | | 25 | | | | | 30 | | |

| Asn | Ala | Glu | Asp | Met | Asp | Gly | Lys | Arg | Gly | Met | Ile | Pro | Val | Pro | Tyr |
| | | | 35 | | | | | 40 | | | | | 45 | | | |

Val Glu
    50

(2) INFORMATION FOR SEQ ID NO:58:

(i) SEQUENCE CHARACTERISTICS:
　　　　(A) LENGTH: 28 amino acids
　　　　(B) TYPE: amino acid
　　　　(D) TOPOLOGY: linear (xi) SEQUENCE DESCRIPTION: SEQ ID NO:58:

Ala Pro Pro Thr Pro Pro Pro Leu Pro Pro Pro Leu Ile Pro Pro
1                5                   10                  15

Pro Pro Leu Pro Pro Gly Leu Gly Pro Leu Pro Pro
            20              25

(2) INFORMATION FOR SEQ ID NO:59:

(i) SEQUENCE CHARACTERISTICS:
　　　　(A) LENGTH: 21 amino acids
　　　　(B) TYPE: amino acid
　　　　(D) TOPOLOGY: linear (xi) SEQUENCE DESCRIPTION: SEQ ID NO:59:

Ala Pro Thr Met Pro Pro Pro Leu Pro Pro Val Pro Pro Gln Pro Ala
1                5                   10                  15

Arg Arg Gln Ser Arg
            20

(2) INFORMATION FOR SEQ ID NO:60:

(i) SEQUENCE CHARACTERISTICS:
　　　　(A) LENGTH: 40 amino acids
　　　　(B) TYPE: amino acid
　　　　(D) TOPOLOGY: linear (xi) SEQUENCE DESCRIPTION: SEQ ID NO:60:

Pro Pro Ala Tyr Pro Pro Pro Pro Val Pro Val Pro Arg Lys Pro Ala
1                5                   10                  15

Phe Ser Asp Leu Pro Arg Ala His Ser Phe Thr Ser Lys Ser Pro Ser
            20              25                  30

Pro Leu Leu Pro Pro Pro Pro Pro
            35              40

(2) INFORMATION FOR SEQ ID NO:61:

(i) SEQUENCE CHARACTERISTICS:
　　　　(A) LENGTH: 12 amino acids
　　　　(B) TYPE: amino acid
　　　　(D) TOPOLOGY: linear (xi) SEQUENCE DESCRIPTION: SEQ ID NO:61:

Pro Pro Ala Leu Pro Pro Pro Pro Arg Pro Val Pro
1                5                   10

(2) INFORMATION FOR SEQ ID NO:62:

(i) SEQUENCE CHARACTERISTICS:
　　　　(A) LENGTH: 84 amino acids
　　　　(B) TYPE: amino acid
　　　　(D) TOPOLOGY: linear (xi) SEQUENCE DESCRIPTION: SEQ ID NO:62:

Cys Asn Val Cys Ala Lys Thr Phe Gly Gln Leu Ser Asn Leu Lys Val
1                5                   10                  15

-continued

```
   His    Leu    Arg    Val    His    Ser    Gly    Glu    Arg    Pro    Phe    Lys    Cys    Gln    Thr    Cys
                        20                                 25                                 30

Asn    Lys    Gly    Phe    Thr    Gln    Leu    Ala    His    Leu    Gln    Lys    His    Tyr    Leu    Val
                 35                                 40                                 45

His    Thr    Gly    Glu    Lys    Pro    His    Glu    Cys    Gln    Val    Cys    His    Lys    Arg    Phe
          50                                 55                                 60

Ser    Ser    Thr    Ser    Asn    Leu    Lys    Thr    His    Leu    Arg    Leu    His    Ser    Gly    Glu
   65                                 70                                 75                                 80

Lys    Pro    Tyr    Gln
```

( 2 ) INFORMATION FOR SEQ ID NO:63:

( i ) SEQUENCE CHARACTERISTICS:
( A ) LENGTH: 80 amino acids
( B ) TYPE: amino acid
( D ) TOPOLOGY: linear ( x i ) SEQUENCE DESCRIPTION: SEQ ID NO:63:

```
   Glu    Val    Ile    Gly    Val    Met    Ser    Lys    Glu    Tyr    Ile    Pro    Lys    Gly    Thr    Arg
   1                           5                                 10                                15

Phe    Gly    Pro    Leu    Ile    Gly    Glu    Ile    Tyr    Thr    Asn    Asp    Thr    Val    Pro    Lys
                        20                                 25                                 30

Asn    Ala    Asn    Arg    Lys    Tyr    Phe    Trp    Arg    Ile    Tyr    Ser    Arg    Gly    Glu    Leu
                 35                                 40                                 45

His    His    Phe    Ile    Asp    Gly    Phe    Asn    Glu    Glu    Lys    Ser    Asn    Trp    Met    Arg
          50                                 55                                 60

Tyr    Val    Asn    Pro    Ala    His    Ser    Pro    Arg    Glu    Gln    Asn    Leu    Ala    Ala    Cys
   65                                 70                                 75                                 80
```

( 2 ) INFORMATION FOR SEQ ID NO:64:

( i ) SEQUENCE CHARACTERISTICS:
( A ) LENGTH: 30 amino acids
( B ) TYPE: amino acid
( D ) TOPOLOGY: linear ( x i ) SEQUENCE DESCRIPTION: SEQ ID NO:64:

```
   Gln    Asn    Gly    Met    Asn    Ile    Tyr    Phe    Tyr    Thr    Ile    Lys    Pro    Ile    Pro    Ala
   1                           5                                 10                                15

Asn    Gln    Glu    Leu    Leu    Val    Trp    Tyr    Cys    Arg    Asp    Phe    Ala    Glu
                        20                                 25                                 30
```

( 2 ) INFORMATION FOR SEQ ID NO:65:

( i ) SEQUENCE CHARACTERISTICS:
( A ) LENGTH: 23 amino acids
( B ) TYPE: amino acid
( D ) TOPOLOGY: linear ( x i ) SEQUENCE DESCRIPTION: SEQ ID NO:65:

```
   Val    Glu    Glu    Ala    Asp    Met    Pro    Asn    Glu    Ser    Ser    Ala    Lys    Glu    Pro    Glu
   1                           5                                 10                                15

Ile    Arg    Cys    Glu    Glu    Lys    Pro
                        20
```

( 2 ) INFORMATION FOR SEQ ID NO:66:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:66:

Leu Gly Pro Val Ser Met Pro Asn Leu Val Pro Glu Val Ile Asp Leu
1               5                   10                  15

Thr Cys His Glu Ala Gly
            20

( 2 ) INFORMATION FOR SEQ ID NO:67:

( i ) SEQUENCE CHARACTERISTICS:
      ( A ) LENGTH: 22 amino acids
      ( B ) TYPE: amino acid
      ( D ) TOPOLOGY: linear ( x i ) SEQUENCE DESCRIPTION: SEQ ID NO:67:

Leu Gly Pro Val Ser Met Pro Asn Leu Val Pro Glu Val Ile Asp Leu
1               5                   10                  15

Thr Cys His Glu Ala Gly
            20

( 2 ) INFORMATION FOR SEQ ID NO:68:

( i ) SEQUENCE CHARACTERISTICS:
      ( A ) LENGTH: 14 amino acids
      ( B ) TYPE: amino acid
      ( D ) TOPOLOGY: linear ( x i ) SEQUENCE DESCRIPTION: SEQ ID NO:68:

Leu Gly Ala Ala Glu Met Asp Leu Arg Cys Tyr Glu Glu Gly
1               5                   10

( 2 ) INFORMATION FOR SEQ ID NO:69:

( i ) SEQUENCE CHARACTERISTICS:
      ( A ) LENGTH: 14 amino acids
      ( B ) TYPE: amino acid
      ( D ) TOPOLOGY: linear ( x i ) SEQUENCE DESCRIPTION: SEQ ID NO:69:

Leu His Pro Glu Asp Met Asp Leu Leu Cys Tyr Glu Met Gly
1               5                   10

( 2 ) INFORMATION FOR SEQ ID NO:70:

( i ) SEQUENCE CHARACTERISTICS:
      ( A ) LENGTH: 22 amino acids
      ( B ) TYPE: amino acid
      ( D ) TOPOLOGY: linear ( x i ) SEQUENCE DESCRIPTION: SEQ ID NO:70:

Val Gly Gly Gly Glu Met Pro Glu Leu Gln Pro Glu Glu Asp Leu
1               5                   10                  15

Phe Cys Tyr Glu Asp Gly
            20

( 2 ) INFORMATION FOR SEQ ID NO:71:

( i ) SEQUENCE CHARACTERISTICS:
      ( A ) LENGTH: 18 amino acids
      ( B ) TYPE: amino acid
      ( D ) TOPOLOGY: linear ( x i ) SEQUENCE DESCRIPTION: SEQ ID NO:71:

Val Gly Glu Glu Leu Leu Pro Val Asp Leu Asp Leu Lys Cys Tyr Glu
1               5                   10                  15

Asp Gly ( 2 ) INFORMATION FOR SEQ ID NO:72:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:72:

```
Glu  Asp  Leu  Leu  Glu  Glu  Pro  Gln  Ser
1                   5
```

( 2 ) INFORMATION FOR SEQ ID NO:73:

( i ) SEQUENCE CHARACTERISTICS:
        ( A ) LENGTH: 10 amino acids
        ( B ) TYPE: amino acid
        ( D ) TOPOLOGY: linear ( x i ) SEQUENCE DESCRIPTION: SEQ ID NO:73:

```
Glu  Asp  Leu  Leu  Asn  Glu  Ser  Gly  Gln  Pro
1                   5                        10
```

( 2 ) INFORMATION FOR SEQ ID NO:74:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:74:

```
Glu  Asp  Leu  Leu  Asn  Glu  Pro  Gly  Gln
1                   5
```

( 2 ) INFORMATION FOR SEQ ID NO:75:

( i ) SEQUENCE CHARACTERISTICS:
        ( A ) LENGTH: 8 amino acids
        ( B ) TYPE: amino acid
        ( D ) TOPOLOGY: linear ( x i ) SEQUENCE DESCRIPTION: SEQ ID NO:75:

```
Glu  Asp  Leu  Leu  Glu  Gly  Gly  Asp
1                   5
```

( 2 ) INFORMATION FOR SEQ ID NO:76:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:76:

```
Leu  Asp  Leu  Ile  Gln  Glu  Glu  Glu  Arg
1                   5
```

( 2 ) INFORMATION FOR SEQ ID NO:77:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:77:

```
His  Asp  Leu  Ile  Glu  Glu  Val  Glu  Gln
1                   5
```

( 2 ) INFORMATION FOR SEQ ID NO:78:

( i ) SEQUENCE CHARACTERISTICS:
      ( A ) LENGTH: 9 amino acids
      ( B ) TYPE: amino acid
      ( D ) TOPOLOGY: linear ( x i ) SEQUENCE DESCRIPTION: SEQ ID NO:78:

```
Glu Asp Leu Leu Glu Glu Asp Pro Thr
1               5
```

( 2 ) INFORMATION FOR SEQ ID NO:79:

( i ) SEQUENCE CHARACTERISTICS:
      ( A ) LENGTH: 50 amino acids
      ( B ) TYPE: amino acid
      ( D ) TOPOLOGY: linear ( x i ) SEQUENCE DESCRIPTION: SEQ ID NO:79:

```
Ser Ala Pro Glu Gln Pro Ala Pro Leu Pro Glu Val Gly Asn Gln Asp
1               5                   10                  15
Ala Val Pro Gln Val Ala Ile Pro Leu Pro Ala Cys Glu Pro Gln Pro
                20                  25                  30
Glu Val Asp Gly Lys Gln Glu Val Thr Asp Cys Glu Val Asn Asp Val
            35                  40                  45
Glu Glu
    50
```

( 2 ) INFORMATION FOR SEQ ID NO:80:

( i ) SEQUENCE CHARACTERISTICS:
      ( A ) LENGTH: 55 amino acids
      ( B ) TYPE: amino acid
      ( D ) TOPOLOGY: linear ( x i ) SEQUENCE DESCRIPTION: SEQ ID NO:80:

```
Ala Leu Arg Asp Phe Gly Lys Pro Asn Asp Gly Lys Ala Ala Trp Thr
1               5                   10                  15
Asp Thr Val Leu Thr Ser Lys Lys Pro Lys Leu Glu Ser Arg Ser Asp
                20                  25                  30
Ser Pro Ala Trp Ser Leu Ser Gly Arg Asp Glu Pro Glu Thr Gly Ser
            35                  40                  45
Pro Pro Cys Phe Asp Glu Tyr
    50                  55
```

( 2 ) INFORMATION FOR SEQ ID NO:81:

( i ) SEQUENCE CHARACTERISTICS:
      ( A ) LENGTH: 92 amino acids
      ( B ) TYPE: amino acid
      ( D ) TOPOLOGY: linear ( x i ) SEQUENCE DESCRIPTION: SEQ ID NO:81:

```
Leu Pro Pro Leu Leu Thr Pro Thr Glu Pro Ser Ser Pro Pro Pro Cys
1               5                   10                  15
Pro Pro Val Leu Thr Val Ala Thr Pro Pro Pro Leu Leu Pro Thr
                20                  25                  30
Val Pro Leu Ser His Pro Ser Ser Asp Ala Ser Pro Gln Gln Cys Pro
            35                  40                  45
Ser Pro Phe Ser Asn Thr Thr Ala Gln Ser Pro Leu Pro Ile Leu Ser
    50                  55                  60
Pro Thr Val Ser Pro Ser Pro Ser Pro Ile Pro Pro Val Glu Pro Leu
65                  70                  75                  80
```

```
            Met  Ser  Ala  Ala  Ser  Pro  Gly  Pro  Pro  Thr  Leu  Ser
                                 85                      90
```

( 2 ) INFORMATION FOR SEQ ID NO:82:

( i ) SEQUENCE CHARACTERISTICS:
        ( A ) LENGTH: 86 amino acids
        ( B ) TYPE: amino acid
        ( D ) TOPOLOGY: linear ( x i ) SEQUENCE DESCRIPTION: SEQ ID NO:82:

```
Cys  Asn  Val  Cys  Glu  Ser  Pro  Phe  Leu  Ser  Ile  Lys  Asp  Leu  Thr  Lys
 1              5                        10                       15

His  Leu  Ser  Val  His  Ala  Glu  Glu  Trp  Pro  Phe  Lys  Cys  Glu  Phe  Cys
               20                       25                       30

Val  Gln  Leu  Phe  Lys  Val  Lys  Thr  Asp  Leu  Ser  Glu  His  Arg  Phe  Leu
               35                       40                  45

Leu  His  Gly  Val  Gly  Asn  Ile  Phe  Val  Cys  Ser  Val  Cys  Lys  Lys  Glu
          50                       55                  60

Phe  Ala  Phe  Leu  Cys  Asn  Leu  Gln  Gln  His  Gln  Arg  Asp  Leu  His  Pro
 65                       70                       75                       80

Asp  Glu  Val  Cys  Thr  His
                    85
```

( 2 ) INFORMATION FOR SEQ ID NO:83:

( i ) SEQUENCE CHARACTERISTICS:
        ( A ) LENGTH: 77 amino acids
        ( B ) TYPE: amino acid
        ( D ) TOPOLOGY: linear ( x i ) SEQUENCE DESCRIPTION: SEQ ID NO:83:

```
Thr  Arg  Ile  Gly  Val  Trp  Ala  Thr  Lys  Pro  Ile  Leu  Lys  Gly  Lys  Lys
 1              5                        10                       15

Phe  Gly  Pro  Phe  Val  Gly  Asp  Lys  Lys  Lys  Arg  Ser  Gln  Val  Arg  Asn
               20                       25                       30

Asn  Val  Tyr  Met  Trp  Glu  Val  Tyr  Tyr  Pro  Asn  Leu  Gly  Trp  Met  Cys
               35                       40                  45

Ile  Asp  Ala  Thr  Asp  Pro  Glu  Lys  Gly  Asn  Trp  Leu  Arg  Tyr  Val  Asn
          50                       55                  60

Trp  Ala  Cys  Ser  Gly  Glu  Glu  Gln  Asn  Leu  Phe  Pro  Leu
 65                       70                       75
```

( 2 ) INFORMATION FOR SEQ ID NO:84:

( i ) SEQUENCE CHARACTERISTICS:
        ( A ) LENGTH: 30 amino acids
        ( B ) TYPE: amino acid
        ( D ) TOPOLOGY: linear ( x i ) SEQUENCE DESCRIPTION: SEQ ID NO:84:

```
Glu  Ile  Asn  Arg  Ala  Ile  Tyr  Tyr  Lys  Thr  Leu  Lys  Pro  Ile  Ala  Pro
 1              5                        10                       15

Gly  Glu  Glu  Leu  Leu  Val  Trp  Tyr  Asn  Gly  Glu  Asp  Asn  Pro
               20                       25                  30
```

( 2 ) INFORMATION FOR SEQ ID NO:85:

( i ) SEQUENCE CHARACTERISTICS:
        ( A ) LENGTH: 8 amino acids
        ( B ) TYPE: amino acid
        ( D ) TOPOLOGY: linear ( x i ) SEQUENCE DESCRIPTION: SEQ ID NO:85:

Gly Lys Pro Asn Asp Gly Lys Ala
1               5

( 2 ) INFORMATION FOR SEQ ID NO:86:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:86:

Asp Glu Arg Glu Thr
1               5

( 2 ) INFORMATION FOR SEQ ID NO:87:

( i ) SEQUENCE CHARACTERISTICS:
( A ) LENGTH: 14 amino acids
( B ) TYPE: amino acid
( D ) TOPOLOGY: linear ( x i ) SEQUENCE DESCRIPTION: SEQ ID NO:87:

Asp Xaa Xaa Xaa Xaa Xaa Xaa Xaa Xaa Xaa Xaa Xaa Xaa Thr
1               5                           10

( 2 ) INFORMATION FOR SEQ ID NO:88:

( i ) SEQUENCE CHARACTERISTICS:
( A ) LENGTH: 13 amino acids
( B ) TYPE: amino acid
( D ) TOPOLOGY: linear ( x i ) SEQUENCE DESCRIPTION: SEQ ID NO:88:

Asp Xaa Xaa Xaa Xaa Xaa Xaa Xaa Xaa Xaa Xaa Xaa Thr
1               5                           10

( 2 ) INFORMATION FOR SEQ ID NO:89:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:89:

Asp Ser Glu Gly
1

( 2 ) INFORMATION FOR SEQ ID NO:90:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:90:

Thr Gln Pro Asp
1

( 2 ) INFORMATION FOR SEQ ID NO:91:

( i ) SEQUENCE CHARACTERISTICS:
( A ) LENGTH: 11 amino acids
( B ) TYPE: amino acid
( D ) TOPOLOGY: linear ( x i ) SEQUENCE DESCRIPTION: SEQ ID NO:91:

```
        Glu  Ile  Arg  Cys  Asp  Glu  Lys  Pro  Glu  Asp  Leu
        1              5                        1 0
```

(2) INFORMATION FOR SEQ ID NO:92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:92:

CCAGAACCAG ACGAGCGATT      20

(2) INFORMATION FOR SEQ ID NO:93:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:93:

AGTTCTGGGG ATTTGCATG      19